United States Patent [19]
Van Leeuwen et al.

[11] Patent Number: 5,958,684
[45] Date of Patent: Sep. 28, 1999

[54] DIAGNOSIS OF NEURODEGENERATIVE DISEASE

[76] Inventors: Frederik Willem Van Leeuwen, Kerweg 37, 3063CL Maarssen, Netherlands; Johannes Peter Henri Burbach, Koperslagershoek 9, 3981 SB Bunnik, Netherlands; Franklin G. Grosveld, 9, Jacubus van Vessemsingel, 3065 NH Rotterdam, Netherlands

[21] Appl. No.: 08/726,306

[22] Filed: Oct. 2, 1996

Related U.S. Application Data

[60] Provisional application No. 60/009,832, Jan. 1, 1996.

[30] Foreign Application Priority Data

Oct. 2, 1995 [GB] United Kingdom ............... 9520080

[51] Int. Cl.⁶ .............. C12Q 1/68; C07H 21/04; G01N 33/53
[52] U.S. Cl. ................ 435/6; 435/7.1; 435/91.2; 536/23.1; 536/23.5; 536/24.3; 536/24.33; 530/350; 530/387.1
[58] Field of Search ............... 435/6, 7.1, 91.2; 935/6, 77, 78; 536/23.1, 24.3, 24.33, 23.5; 530/389.1, 350

[56] References Cited

U.S. PATENT DOCUMENTS

| | | | |
|---|---|---|---|
| 4,666,829 | 5/1987 | Glenner et al. | 435/6 |
| 4,727,041 | 2/1988 | Aroonsakul | 424/288 |
| 4,816,416 | 3/1989 | Averback | 436/166 |
| 4,933,159 | 6/1990 | Nowack et al. | 423/245.1 |
| 5,015,570 | 5/1991 | Scangos et al. | 435/6 |
| 5,220,013 | 6/1993 | Ponte et al. | 536/23.5 |
| 5,352,775 | 10/1994 | Albertsen et al. | 536/23.1 |
| 5,654,138 | 8/1997 | Lerman et al. | 435/6 |

FOREIGN PATENT DOCUMENTS

| | | |
|---|---|---|
| 0 341 491 A3 | 11/1989 | European Pat. Off. . |
| 0 451 700 A1 | 10/1991 | European Pat. Off. . |
| WO 9532731 | 7/1995 | United Kingdom . |
| WO 94/02851 | 2/1994 | WIPO . |
| WO 95/05604 | 2/1995 | WIPO . |

OTHER PUBLICATIONS

Allen and Burns, 1995, *J. Psychopharm.* 9: 43–56.
Bush et al., 1990, *J. Biol. Chem.* 265: 15977–15983.
Sherrington et al., 1995, *Nature* 375: 254–260.
Sullenger and Cech, 1994, Ribozyme–mediated repair of defective mRNA by targeted trans–splicing, *Nature* 371: 619–622.
Evans et al., *PNAS* 91: 6059–6063 (1994).
International Search Report PCT/IB96/01106.
Antequeva et al 8:114 Nature Genetics, Oct. 1991.
Caskey. Science 236:1223–1229, Jun. 1987.
Kelloff et al J. Cell. Biochem 166:15–21, 1992.

*Primary Examiner*—Carla J. Myers
*Attorney, Agent, or Firm*—Kathleen M. Williams; Banner & Witcoff, Ltd.

[57] ABSTRACT

The invention encompasses methods and reagents for the diagnosis of a disease caused by or associated with a gene having a somatic mutation giving rise to a frameshift mutation. The methods include the steps of providing a body fluid or tissue sample from a patient; and analyzing the sample for the presence of a gene having a frameshift mutation or a protein encoded thereby, wherein the presence of the mutated gene or encoded protein is indicative of the disease.

12 Claims, 25 Drawing Sheets

FIG. 2A

147
ATGCTGCCCGGTTTGGCACTGCTCCTGCTGGCCGCCTGGACGGCTCGGGCGCTGGAGGTA

```
  C   C   P   V   W   H   C   S   C   W   P   P   G   R   L   G   R   W   R   Y
    A   A   R   F   G   T   A   P   A   G   R   L   D   G   S   G   A   G   G   T
M   L   P   G   L   A   L   L   L   L   A   A   W   T   A   R   A   L   E   V
```

CCCACTGATGGTAATGCTGGCCTGCTGGCTGAACCCCAGATTGCCATGTTCTGTGGCAGA

```
  P   L   M   V   M   L   A   C   W   L   N   P   R   L   P   C   S   V   A   D
    H   *   W   *   C   W   P   A   G   *   T   P   D   C   H   V   L   W   Q   T
P   T   D   G   N   A   G   L   L   A   E   P   Q   I   A   M   F   C   G   R
```

CTGAACATGCACATGAATGTCCAGAATGGGAAGTGGGATTCAGATCCATCAGGGACCAAA

```
  *   T   C   T   *   M   S   R   M   G   S   G   I   Q   I   H   Q   G   P   K
    E   H   A   H   E   C   P   E   W   E   V   G   F   R   S   I   R   D   Q   N
L   N   M   H   M   N   V   Q   N   G   K   W   D   S   D   P   S   G   T   K
```

ACCTGCATTGATACCAAGGAAGGCATCCTGCAGTATTGCCAAGAAGTCTACCCTGAACTG

```
  P   A   L   I   P   R   K   A   S   C   S   I   A   K   K   S   T   L   N   C
    L   H   *   Y   Q   G   R   H   P   A   V   L   P   R   S   L   P   *   T   A
T   C   I   D   T   K   E   G   I   L   Q   Y   C   Q   E   V   Y   P   E   L
```

CAGATCACCAATGTGGTAGAAGCCAACCAACCAGTGACCATCCAGAACTGGTGCAAGCGG

```
  R   S   P   M   W   *   K   P   T   N   Q   *   P   S   R   T   G   A   S   G
    D   H   Q   C   G   R   S   Q   P   T   S   D   H   P   E   L   V   Q   A   G
Q   I   T   N   V   V   E   A   N   Q   P   V   T   I   Q   N   W   C   K   R
```

GGCCGCAAGCAGTGCAAGACCCATCCCCACTTTGTGATTCCCTACCGCTGCTTAGTTGGT

```
  A   A   S   S   A   R   P   I   P   T   L   *   F   P   T   A   A   *   L   V
    P   Q   A   V   Q   D   P   S   P   L   C   D   S   L   P   L   L   S   W   *
G   R   K   Q   C   K   T   H   P   H   F   V   I   P   Y   R   C   L   V   G
```

566
GAGTTTGTAAGTGATGCCCTTCTCGTTCCTGACAAGTGCAAATTCTTACACCAG[GAGAG]G

1047
GACAAGTATCTCGAGACACCTGGGGATGAGAATGAACATGCCCATTTCCAGAAAGCCAAA

```
 T  S  I  S  R  H  L  G  M  R  M  N  M  P  I  S  R  K  P  K
   Q  V  S  R  D  T  W  G  *  E  *  T  C  P  F  P  E  S  Q  R
 D  K  Y  L  E  T  P  G  D  E  N  E  H  A  H  F  Q  K  A  K
```

GAGAGGCTTGAGGCCAAGCACCGAGAGAGAATGTCCCAGGTCATGAGAGAATGGGAAGAG

```
 R  G  L  R  P  S  T  E  R  E  C  P  R  S  *  E  N  G  K  R
   E  A  *  G  Q  A  P  R  E  N  V  P  G  H  E  R  M  G  R  G
 E  R  L  E  A  K  H  R  E  R  M  S  Q  V  M  R  E  W  E  E
```

GCAGAACGTCAAGCAAAGAACTTGCCTAAAGCTGATAAGAAGGCAGTTATCCAGCATTTC

```
 Q  N  V  K  Q  R  T  C  L  K  L  I  R  R  Q  L  S  S  I  S
   R  T  S  S  K  E  L  A  *  S  *  *  E  G  S  Y  P  A  F  P
 A  E  R  Q  A  K  N  L  P  K  A  D  K  K  A  V  I  Q  H  F
```

CAGGAGAAAGTGGAATCTTTGGAACAGGAAGCAGCCAACGAGAGACAGCAGCTGGTGGAG

```
 R  R  K  W  N  L  W  N  R  K  Q  P  T  R  D  S  S  W  W  R
   G  E  S  G  I  F  G  T  G  S  S  Q  R  E  T  A  A  G  G  D
 Q  E  K  V  E  S  L  E  Q  E  A  A  N  E  R  Q  Q  L  V  E
```

ACACACATGGCCAGAGTGGAAGCCATGCTCAATGACCGCCGCCGCCTGGCCCTGGAGAAC

```
 H  T  W  P  E  W  K  P  C  S  M  T  A  A  A  W  P  W  R  T
   T  H  G  Q  S  G  S  H  A  Q  *  P  P  P  P  G  P  G  E  L
 T  H  M  A  R  V  E  A  M  L  N  D  R  R  R  L  A  L  E  N
```

TACATCACCGCTCTGCAGGCTGTTCCTCCTCGGCCTCGTCACGTGTTCAATATGCTAAAG

```
 T  S  P  L  C  R  L  F  L  L  G  L  V  T  C  S  I  C  *  R
   H  H  R  S  A  G  C  S  S  S  A  S  S  R  V  Q  Y  A  K  E
 Y  I  T  A  L  Q  A  V  P  P  R  P  R  H  V  F  N  M  L  K
```

AAGTATGTCCGCGCAGAACAGAAGGACAGACAGCACACCCTAAAGCATTTCGAGCATGTG

```
 S  M  S  A  Q  N  R  R  T  D  S  T  P  *  S  I  S  S  M  C
   V  C  P  R  R  T  E  G  Q  T  A  H  P  K  A  F  R  A  C  A
 K  Y  V  R  A  E  Q  K  D  R  Q  H  T  L  K  H  F  E  H  V
```

CGCATGGTGGATCCCAAGAAAGCCGCTCAGATCCGGTCCCAGGTTATGACACACCTCCGT

A  W  W  I  P  R  K  P  L  R  S  G  P  R  L  *  H  T  S  V
 H  G  G  S  Q  E  S  R  S  D  P  V  P  G  Y  D  T  P  P  C
R  M  V  D  P  K  K  A  A  Q  I  R  S  Q  V  M  T  H  L  R

1586
GTGATTTATGAGCGCATGAATCAGTCTCTCTCCCTGCTCTACAACGTGCCTGCAGTGGCC

```
ATGGCTGAGCCCCGCCAGGAGTTCGAAGTGATGGAAGATCACGCTGGGACGTACGGGTTG

G * A P P G V R S D G R S R W D V R V G
M A E P R Q E F E V M E D H A G T Y G L
 W L S P A R S S K * W K I T L G R T G W

GGGGACAGGAAAGATCAGGGGGGCTACACCATGCACCAAGACCAAGAGGGTGACACGGAC

G Q E R S G G L H H A P R P R G * H G R
 G D R K D Q G G Y T M H Q D Q E G D T D
  G T G K I R G A T P C T K T K R V T R T

GCTGGCCTGAAAGCTGAAGAAGCAGGCATTGGAGACACCCCCAGCCTGGAAGACGAAGCT

W P E S * R S R H W R H P Q P G R R S C
 A G L K A E E A G I G D T P S L E D E A
  L A * K L K K Q A L E T P P A W K T K L

GCTGGTCACGTGACCCAAGCTCGCATGGTCAGTAAAAGCAAAGACGGGACTGGAAGCGAT

W S R D P S S H G Q * K Q R R D W K R *
 A G H V T Q A R M V S K S K D G T G S D
  L V T * P K L A W S V K A K T G L E A M

GACAAAAAAGCCAAGGGGGCTGATGGTAAAACGAAGATCGCCACACCGCGGGGAGCAGCC

Q K S Q G G * W * N E D R H T A G S S P
 D K K A K G A D G K T K I A T P R G A A
  T K K P R G L M V K R R S P H R G E Q P

CCTCCAGGCCAGAAGGGCCAGGCCAACGCCACCAGGATTCCAGCAAAAACCCCGCCCGCT

S R P E G P G Q R H Q D S S K N P A R S
 P P G Q K G Q A N A T R I P A K T P P A
  L Q A R R A R P T P P G F Q Q K P R P L

CCAAAGACACCACCCAGCTCTGGTGAACCTCCAAAATCAGGGGATCGCAGCGGCTACAGC

```
AGCCCCGGCTCCCCAGGCACTCCCGGCAGCCGCTCCCGCACCCCGTCCCTTCCAACCCCA

P  R  L  P  R  H  S  R  Q  P  L  P  H  P  V  P  S  N  P  T
 S  P  G  S  P  G  T  P  G  S  R  S  R  T  P  S  L  P  T  P
  A  P  A  P  Q  A  L  P  A  A  A  P  A  P  R  P  F  Q  P  H

CCCACCCGGGAGCCCAAGAAGGTGGCAGTGGTCCGTACTCCACCCAAGTCGCCGTCTTCC

H  P  G  A  Q  E  G  G  S  G  P  Y  S  T  Q  V  A  V  F  R
 P  T  R  E  P  K  K  V  A  V  V  R  T  P  P  K  S  P  S  S
  P  P  G  S  P  R  R  W  Q  W  S  V  L  H  P  S  R  R  L  P

GCCAAGAGCCGCCTGCAGACAGCCCCCGTGCCCATGCCAGACCTGAAGAATGTCAAGTCC

Q  E  P  P  A  D  S  P  R  A  H  A  R  P  E  E  C  Q  V  Q
 A  K  S  R  L  Q  T  A  P  V  P  M  P  D  L  K  N  V  K  S
  P  R  A  A  C  R  Q  P  P  C  P  C  Q  T  *  R  M  S  S  P

AAGATCGGCTCCACT[GAGA]ACCTGAAGCACCAGCCGGGAGGCGGGAAGGTGCAAATAGTC

D  R  L  H  *  E  P  E  A  P  A  G  R  R  E  G  A  N  S  L
 K  I  G  S  T  E  N  L  K  H  Q [P  G  G  G] K  V  Q  I  V
  R  S  A  P  L  R  T  *  S  T  S  R  E  A  G  R  C  K  *  S

TACAAACCAGTTGACCTGAGCAAGGTGACCTCCAAGTGTGGCTCATTAGGCAACATCCAT

Q  T  S  *  P  E  Q  G  D  L  Q  V  W  L  I  R  Q  H  P  S
 Y  K  P  V  D  L  S  K  V  T  S  K  C  G  S  L  G  N  I  H
  T  N  Q  L  T  *  A  R  *  P  P  S  V  A  H  *  A  T  S  I

CATAAACCAGGAGGTGGCCAGGTGGAAGTAAAATCT[GAGA]AGCTTGACTTCAAGGACAGA

*  T  R  R  W  P  G  G  S  K  I  *  E  A  *  L  Q  G  Q  S
 H  K [P  G  G  G] Q  V  E  V  K  S  E  K  L  D  F  K  D  R
  I  N  Q  E  V  A  R  W  K  *  N  L  R  S  L  T  S  R  T  E

GTCCAGTCGAAGATTGGGTCCCTGGACAATATCACCCACGTCCCTGGCGGAGGAAATAAA

P  V  E  D  W  V  P  G  Q  Y  H  P  R  P  W  R  R  K  *  K
 V  Q  S  K  I  G  S  L  D  N  I  T  H  V [P  G  G  G] N  K
  S  S  R  R  L  G  P  W  T  I  S  P  T  S  L  A  E  E  I  K
```

```
AAGATTGAAACCCACAAGCTGACCTTCCGCGAGAACGCCAAAGCCAAGACAGACCACGGG

D  *  N  P  Q  A  D  L  P  R  E  R  Q  S  Q  D  R  P  R  G
   K  I  E  T  H  K  L  T  F  R  E  N  A  K  A  K  T  D  H  G
   R  L  K  P  T  S  *  P  S  A  R  T  P  K  P  R  Q  T  T  G

GCGGAGATCGTGTACAAGTCGCCAGTGGTGTCTGGGGACACGTCTCCACGGCATCTCAGC

G  D  R  V  Q  V  A  S  G  V  W  G  H  V  S  T  A  S  Q  Q
   A  E  I  V  Y  K  S  P  V  V  S  G  D  T  S  P  R  H  L  S
   R  R  S  C  T  S  R  Q  W  C  L  G  T  R  L  H  G  I  S  A

AATGTCTCCTCCACCGGCAGCATCGACATGGTAGACTCGCCCCAGCTCGCCACGCTAGCT

C  L  L  H  R  Q  H  R  H  G  R  L  A  P  A  R  H  A  S  *
   N  V  S  S  T  G  S  I  D  M  V  D  S  P  Q  L  A  T  L  A
   M  S  P  P  P  A  A  S  T  W  *  T  R  P  S  S  P  R  *  L

GACGAGGTGTCTGCCTCCCTGGCCAAGCAGGGTTTGTGA

```
ATGCAGATCTTCGTGAAAACCCTTACCGGCAAGACCATCACCCTTGAGGTGGAGCCCAGT

A  D  L  R  E  N  P  Y  R  Q  D  H  H  P  *  G  G  A  Q  *
M Q  I  F  V  K  T  L  T  G  K  T  I  T  L  E  V  E  P  S
 C  R  S  S  *  K  P  L  P  A  R  P  S  P  L  R  W  S  P  V

GACACCATCGAAAATGTGAAGGCCAAGATCCAGGATAAGGAAGGCATTCCCCCCGACCAG

H  H  R  K  C  E  G  Q  D  P  G  *  G  R  H  S  P  R  P  A
 D  T  I  E  N  V  K  A  K  I  Q  D  K  E  G  I  P  P  D  Q
  T  P  S  K  M  *  R  P  R  S  R  I  R  K  A  F  P  P  T  S

CAGAGGCTCATCTTTGCAGGCAAGCAGCTGGAAGATGGCCGTACTCTTTCTGACTACAAC

E  A  H  L  C  R  Q  A  A  G  R  W  P  Y  S  F  *  L  Q  H
 Q  R  L  I  F  A  G  K  Q  L  E  D  G  R  T  L  S  D  Y  N
  R  G  S  S  L  Q  A  S  S  W  K  M  A  V  L  F  L  T  T  T

ATCCAGAAGGAGTCGACCCTGCACCTGGTCCTGCGTCT[GAGAG]GTGGTATGCAGATCTTC

P  E  G  V  D  P  A  P  G  P  A  S  E  R  W [Y  A  D  L  R
  I  Q  K  E  S  T  L  H  L  V  L  R  L  R  G  G| M  Q  I  F
   S  R  R  S  R  P  C  T  W  S  C  V  *  E  V  V  C  R  S  S

GTGAAGACCCTGACCGGCAAGACCATCACCCTGGAAGTGGAGCCCAGTGACACCATCGAA

E  D  P  D [R  Q] D  H  H  P  G  S  G  A  Q] *  H  H  R  K
 V  K  T  L  T  G  K  T  I  T  L  E  V  E  P  S  D  T  I  E
  *  R  P  *  P  A  R  P  S  P  W  K  W  S  P  V  T  P  S  K

AATGTGAAGGCCAAGATCCAGGATAAAGAAGGCATCCCTCCCGACCAGCAGAGGCTCATC

C  E  G  Q  D  P  G  *  R  R  H  P  S  R  P  A  E  A  H  L
  N  V  K  A  K  I  Q  D  K  E  G  I  P  P  D  Q  Q  R  L  I
   M  *  R  P  R  S  R  I  K  K  A  S  L  P  T  S  R  G  S  S

TTTGCAGGCAAGCAGCTGGAAGATGGCCGCACTCTTTCTGACTACAACATCCAGAAGGAG

C  R  Q  A  A  G  R  W  P  H  S  F  *  L  Q  H  P  E  G  V
  F  A  G  K  Q  L  E  D  G  R  T  L  S  D  Y  N  I  Q  K  E
   L  Q  A  S  S  W  K  M  A  A  L  F  L  T  T  T  S  R  R  S
```

```
TCGACCCTGCACCTGGTCCTGCGTCTGAGAGGTGGTATGCAGATCTTCGTGAAGACCCTG

D  P  A  P  G  P  A  S  E  R  W  Y  A  D  L  R  E  D  P  D
S  T  L  H  L  V  L  R  L  R  G  G |M  Q  I  F  V  K  T  L
 R  P  C  T  W  S  C  V  *  E  V  V  C  R  S  S  *  R  P  *

ACCGGCAAGACCATCACTCTGGAAGTGGAGCCCAGTGACACCATCGAAAATGTGAAGGCC

R  Q  D  H  H  S  G  S  G  A  Q  *  H  H  R  K  C  E  G  Q
 T  G  K  T  I  T  L  E  V  E  P  S  D  T  I  E  N  V  K  A
  P  A  R  P  S  L  W  K  W  S  P  V  T  P  S  K  M  *  R  P

AAGATCCAAGATAAAGAAGGCATCCCTCCCGACCAGCAGAGGCTCATCTTTGCAGGCAAG

D  P  R  *  R  R  H  P  S  R  P  A  E  A  H  L  C  R  Q  A
 K  I  Q  D  K  E  G  I  P  P  D  Q  Q  R  L  I  F  A  G  K
  R  S  K  I  K  K  A  S  L  P  T  S  R  G  S  S  L  Q  A  S

CAGCTGGAAGATGGCCGCACTCTTTCTGACTACAACATCCAGAAGGAGTCGACCCTGCAC

A  G  R  W  P  H  S  F  *  L  Q  H  P  E  G  V  D  P  A  P
  Q  L  E  D  G  R  T  L  S  D  Y  N  I  Q  K  E  S  T  L  H
   S  W  K  M  A  A  L  F  L  T  T  T  S  R  R  S  R  P  C  T

CTGGTCCTGCGCCTGAGGGGTGGCTGTTAATTCTTCAGTCATGGCAT

```
CCCCAGCGGAGGTGAAGGACGTCCTTCCCCAGGAGCCGACTGGCCAATCACAGGCAGGAA

P  Q  R  R  *  R  T  S  F  P  R  S  R  L  A  N  H  R  Q  E
 P  S  G  G  E  G  R  P  S  P  G  A  D  W  P  I  T  G  R  K
  P  A  E  V  K  D  V  L  P  Q  E  P  T  G  Q  S  Q  A  G  R

GATGAAGGTTCTGTGGGCTGCGTTGCTGGTCACATTCCTGGCAGGATGCCAGGCCAAGGT

D  E  G  S  V  G  C  V  A  G  H  I  P  G  R  M  P  G  Q  G
  M  K  V  L  W  A  A  L  L  V  T  F  L  A  G  C  Q  A  K  V
*  R  F  C  G  L  R  C  W  S  H  S  W  Q  D  A  R  P  R  W

GGAGCAAGCGGTG|GAGAC|AGAGCCGGAGCCCGAGCTGCGCCAGCAGACCGAGTGGCAGAG

G  A  S  G  G  D  R  A  G  A  R  A  A  P  A  D  R  V  A  E
  E  Q  A  V  E  T  E  P  E  P  E  L  R  Q  Q  T  E  W  Q  S
   S  K  R  W  R  Q  S  R  S  P  S  C  A  S  R  P  S  G  R  A

CGGCCAGCGCTGGGAACTGGCACTGGGTCGCTTTTGGGATTACCTGCGCTGGGTGCAGAC

R  P  A  L  G  T  G  T  G  S  L  L |G  L  P  A  L  G  A  D
  G  Q  R  W  E  L  A  L  G  R  F  W  D  Y  L  R  W  V  Q  T
   A  S  A  G  N  W  H  W  V  A  F  G  I  T  C  A  G  C  R  H

ACTGTCTGAGCAGGTGCAGGAGGAGCTGCTCAGCTCCCAAGTCACCCAAGAACTGAGGGC

|T  V| *  A  G  A  G  G  A  A  Q  L  P  S  H  P  R  T  E  G
  L  S  E  Q  V  Q  E  E  L  L  S  S  Q  V  T  Q  E  L  R  A
   C  L  S  R  C  R  R  S  C  S  A  P  K  S  P  K  N  *  G  R

GCTGATGGAC|GAGAC|CATGAAGGAGTTGAAGGCCTACAAATCGGAACTGGAGGAACAACT

A  D  G  R  D  H  E  G  V  E  G  L  Q  I  G  T  G  G  T  T
  L  M  D  E  T  M  K  E  L  K  A  Y  K  S  E  L  E  E  Q  L
   *  W  T  R  P  *  R  S  *  R  P  T  N  R  N  W  R  N  N  *

GACCCCGGTAGCGGAGGAGACGCGGGCACGGCTGTCCAAGGAGCTGCAGACGGCGCAGGC

D  P  G  S  G  G  D  A  G  T  A  V  Q  G  A  A  D  G  A  G
  T  P  V  A  E  E  T  R  A  R  L  S  K  E  L  Q  T  A  Q  A
   P  R  *  R  R  R  R  G  H  G  C  P  R  S  C  R  R  R  R  P
```

```
CCGGCTGGGCGCGGACATGGAGGACGTGTGCGGCCGCCTGGTGCAGTACCGCGGCGAGGT

P  A  G  R  G  H  G  G  R  V  R  P  P  G  A  V  P  R  R  G
 R  L  G  A  D  M  E  D  V  C  G  R  L  V  Q  Y  R  G  E  V
  G  W  A  R  T  W  R  T  C  A  A  A  W  C  S  T  A  A  R  C

GCAGGCCATGCTCGGCCAGAGCACCGAGGAGCTGCGGGTGCGCCTCGCCTCCCACCTGCG

A  G  H  A  R  P  E  H  R  G  A  A │G  A  P  R  L  P  P  A│
 Q  A  M  L  G  Q  S  T  E  E  L  R  V  R  L  A  S  H  L  R
  R  P  C  S  A  R  A  P  R  S  C  G  C  A  S  P  P  T  C  A

CAAGCTGCGTAAGCGGCTCCTCCGCGATCCCGATGACCTGCAGAAGCGCCTGGCAGTGTA

│Q  A  A│ *  A  A  P  P  R  S  R  *  P  A  E  A  P  G  S  V
 K  L  R  K  R  L  L  R  D  P  D  D  L  Q  K  R  L  A  V  Y
  S  C  V  S  G  S  S  A  I  P  M  T  C  R  S  A  W  Q  C  T

CCAGGCCGGGGCCCGCGAGGGCGCCGAGCGCGGCCTCAGCGCCATCCGCGAGCGCCTGGG

```
GCAGGGAAGAGTGGTACCTCAACACCCACTACCCCTGGGTCTACTGCCATCACTCCTGGC

A  G  K  S  G  T  S  T  P  T  T  P  G  S  T  A  I  T  P  G
  Q  G  R  V  V  P  Q  H  P  L  P  L  G  L  L  P  S  L  L  A
   R  E  E  W  Y  L  N  T  H  Y  P  W  V  Y  C  H  H  S  W  H

ACCCCACCAAGTTATTCTTCACGCACACCAGGCACTCCTGGAACCCCTAGCTATCCCAGG

T  P  P  S  Y  S  S  R  T  P  G  T  P  G  T  P  S  Y  P  R
  P  H  Q  V  I  L  H  A  H  Q  A  L  L  E  P  L  A  I  P  G
   P  T  K  L  F  F  T  H  T  R  H  S  W  N  P  *  L  S  Q  D

ACCCCTCACACACCAGGAACCCCCAAGTCTGCCATCTTGGTGCCGAGTGAGAAGAAGGTC

T  P  H  T  P  G  T  P  K  S  A  I  L  V  P  S  E  K  K  V
  P  L  T  H  Q  E  P  P  S  L  P  S  W  C  R  V  R  R  R  S
   P  S  H  T  R  N  P  Q  V  C  H  L  G  A  E  *  E  E  G  R

GCCATCATACGTACTCCTCCAAAATCTCCTGGACTGACTCCCAAGCAGCTTCGGCTTATT

A  I  I  R  T  P  P  K  S  P  G  L  T  P  K  Q  L  R  L  I
  P  S  Y  V  L  L  Q  N  L  L  D  *  L  P  S  S  F  G  L  L
   H  H  T  Y  S  S  K  I  S  W  T  D  S  Q  A  A  S  A  Y  *

AACCAACCACTGCCAGACCTGAAGAATGTCAAATCCAAAATCGGATCAACAGACAACATC

N  Q  P  L  P  D  L  K  N |V  K  S  K  I  G  S  T  D  N  I
  T  N  H  C  Q  T  *  R  M  S  N  P  K  S  D  Q  Q  T  T  S
   P  T  T  A  R  P  E  E  C  Q  I  Q  N  R  I  N  R  Q  H  Q

AAATACCAGCCTAAAGGGGGGCAGGTACAAATTGTTACCAAGAAGATAGACCTAAGCCAT

|K  Y  Q  P  K  G  G| Q  V  Q  I  V  T  K  K  I  D  L  S  H
 N  T  S  L  K  G  G  R  Y  K  L  L  P  R  R  *  T  *  A  M
  I  P  A  *  R  G  A  G  T  N  C  Y  Q  E  D  R  P  K  P  C

GTGACATCCAAATGTGGCTCTCTGAAGAACATCCGCCACAGGCCAGGTGGCGGACGTGTG

|V  T  S  K  C  G  S  L  K  N  I  R  H  R  P  G  G| G  R  V
 *  H  P  N  V  A  L  *  R  T  S  A  T  G  Q  V  A  D  V  *
  D  I  Q  M  W  L  S  E  E  H  P  P  Q  A  R  W  R  T  C  E
```

AAAATT`GAGAG`TGTAAAACTAGATTTCAAAGAAAAGGCCCAAGCTAAAGTTGGTTCTCTT

1
GCAGCTCCTCGGGCCGTAGCTCGACCCCGCCTTCCCTTTT

```
  Q   L   L   G   P   *   L   D   P   A   F   P   F
    E   S   S   G   R   S   S   T   P   P   S   L   F
  A   A   P   R   A   V   A   R   P   R   L   P   F   S
```

CCGCAGAATCCTCGCCTTGGCTGCAGCAGCGCGCTGCCCCCACTGGCCGGCGTGCCGTGA

```
  P   Q   N   P   R   L   G   C   S   S   A   L   P   P   L   A   G   V   P   *
    R   R   I   L   A   L   A   A   A   A   R   C   P   H   W   P   A   C   R   D
      A   E   S   S   P   W   L   Q   Q   R   A   A   P   T   G   R   R   A   V   I
```

TCGATCGCAGGCTGCGTCAGGACCTCCCGGCGTATAAATAGGGGTGGCAGAACGGCGCCG

```
  S   I   A   G   C   V   R   T   S   R   R   I   N   R   G   G   R   T   A   P
    R   S   Q   A   A   S   G   P   P   G   V   *   I   G   V   A   E   R   R   R
      D   R   R   L   R   Q   D   L   P   A   Y   K   *   G   W   Q   N   G   A   E
```

AGCCGCACACAGCCATCCATCCTCCCCCTTCCCTCTCTCCCCTGTCCTCTCTCTCCGGGC

```
  S   R   T   Q   P   S   I   L   P   L   P   S   L   P   C   P   L   S   P   G
    A   A   H   S   H   P   S   S   P   F   P   L   S   P   V   L   S   L   R   A
      P   H   T   A   I   H   P   P   P   S   L   S   P   L   S   S   L   S   G   L
```

TCCCACCGCCGCCGGGGAGCACCGGCCGCCAACCAATGAGTTCCTTCAGCTACGAGCCGT

```
  S   H   R   R   R   G   A   P   A   A   N   Q   *   V   P   S   A   T   S   R
    P   T   A   A   G   E   H   R   P   P   T   N   E   F   L   Q   L   R   A   V
      P   P   P   P   G   S   T   G   R   Q   P   M   S   S   F   S   Y   E   P   Y
```

ACTACTCGACCTCCTACAAGCGGCGCTACGTGGAGACGCCCCGGGTGCATATCAGCGTGC

```
GCAGCGGCTACAGCACCGCACGCTCAGCTTACTCAAGCTACTCGGCGCCGGTGTCTTCCT

A  A  A  T  A  P  H
 Q  R  L  Q  H  R  T
  S  G  Y  S  T  A  R  S  A  Y  S  S  Y  S  A  P  V  S  S  S

420
CGCTGTCCGTGCGCCGCAGC
-
-
  L  S  V  R  R  S

901
AGCTTGATGGACGAAATCTCTTTTCTGAAGAAAGTGCACG

A  *  W  T  K  S  L  F  *  R  K  C  T
 L  D  G  R  N  L  F  S  E  E  S  A  R
S  L  M  D  E  I  S  F  L  K  K  V  H  E

AAGAGGAGATCGCCGAACTGCAGGCGCAGATCCAGTACGCGCAGATCTCCGTGGAGATGG

K  R  R  S  P  N  C  R  R  R  S  S  T  R  R  S  P  W  R  W
 R  G  D  R  R  T  A  G  A  D  P  V  R  A  D  L  R  G  D  G
  E  E  I  A  E  L  Q  A  Q  I  Q  Y  A  Q  I  S  V  E  M  D

ACGTGACCAAGCCCGACCTTTCCGCCGCGCTCAAGGACATCCGCGCGCAGTACGAGAAGC

T  *  P  S  P  T  F  P  P  R  S  R  T  S  A  R  S  T  R  S
 R  D  Q  A  R  P  F  R  R  A  Q  G  H  P  R  A  V  R  E  A
  V  T  K  P  D  L  S  A  A  L  K  D  I  R  A  Q  Y  E  K  L

TGGCCGCCAAGAACATGCAGAACGCTGAGGAATGGTTCAAGAGCCGCTTCACGGTGCTGA

W  P  P  R  T  C  R  T  L  R  N  G  S  R  A  A  S  R  C  *
 G  R  Q  E  H  A  E  R  *  G  M  V  Q  E  P  L  H  G  A  D
  A  A  K  N  M  Q  N  A  E  E  W  F  K  S  R  F  T  V  L  T

CCGAGAGCGCCGCCAAGAACACCGACGCCGTGCGCGCCGCCAAGGACGAGGTGTCGGAGA

P  R  A  P  P  R  T  P  T  P  C  A  P  P  R  T  R  C  R  R
 R  E  R  R  Q  E  H  R  R  R  A  R  R  Q  G  R  G  V  G  E
  E  S  A  A  K  N  T  D  A  V  R  A  A  K  D  E  V  S  E  S
```

```
GCCGTCGTCTGCTCAAGGCCAAGACCCTGGAAATCGAAGCATGCCGGGGCATGAATGAAG
```

```
A  V  V  C  S  R  P  R  P  W  K  S  K  H  A  G  A  *  M  K
 P  S  S  A  Q  G  Q  D  P  G  N  R  S  M  P  G  H  E  *  S
  R  R  L  L  K  A  K  T  L  E  I  E  A  C  R  G  M  N  E  A
```

```
CGCTGGAGAAGCAGCTGCAGGAGCTGGAGGACAAGCAGAACGCCGACATCAGCGCTATGC
```

```
R  W  R  S  S  C  R  S  W  R  T  S  R  T  P  T  S  A  L  C
 A  G  E  A  A  A  G  A  G  G  Q  A  E  R  R  H  Q  R  Y  A
  L  E  K  Q  L  Q  E  L  E  D  K  Q  N  A  D  I  S  A  M  Q
```

```
AGGTGCGGCACGGCCAGAAACACAGGGGGGCGGGGAACTCGAGCAAGGGGGGGAGTTGGT
```

```
R  C  G  T  A  R  N  T  G  G  R  G  T  R  A  R  G  G  V  G
 G  A  A  R  P  E  T  Q  G  G  G  E  L  E  Q  G  G  E  L  V
  V  R  H  G  Q  K  H  R  G  A  G  N  S  S  K  G  G  S  W  C
```

```
GCGCCCAGAAAGCGAAACCA
```

```
A  P  R  K  R  N  Q
 R  P  E  S  E  T  R
  A  Q  K  A  K  P
```

```
                                                         1440
GGGGTGGTGCGGCTGCCCAGCTCTTAGGGATAGGGCTTGGCTCCTTGGCCACTGTGTGGA
```

```
1
CAGCTGCTTTAAGACAAGGGGTGGGGGAAGGGGAGGGAGGCAAGAAAAGATGAGGGTGGG

Q  L  L  *  D  K  G  W  G  K  G  R  E  A  R  K  D  E  G  G
   S  C  F  K  T  R  G  G  G  R  G  G  R  Q  E  K  M  R  V  G
    A  A  L  R  Q  G  V  G  E  G  E  G  G  K  K  R  *  G  W  G

GGAGGGGAAAAGAGGGAATGCAAGGGGAAGGAGGGAGGAGACGGGGAGAAGGAAAGATTG

G  G  E  K  R  E  C  K  G  K  E  G  G  D  G  E  K  E  R  L
   E  G  K  R  G  N  A  R  G  R  R  E  E  T  G  R  R  K  D  W
    R  G  K  E  G  M  Q  G  E  G  G  R  R  R  G  E  G  K  I  G

GAAGAAAAGGATCTCCGAGGAAGGGGCTGAGAGAAGGGCAGGGTGAACTGGACTAAAGGC

E  E  K  D  L  R  G  R  G  *  E  K  G  R  V  N  W  T  K  G
   K  K  R  I  S  E  E  G  A  E  R  R  A  G  *  T  G  L  K  A
    R  K  G  S  P  R  K  G  L  R  E  G  Q  G  E  L  D  *  R  P

CAGAGTAGGAAGGAGAAGAGGGGCCAAAAAAGAAGGGGATGAAATTAAGCACAGAAGATG

Q  S  R  K  E  K  R  G  Q  K  R  R  G  *  N  *  A  Q  K  M
   R  V  G  R  R  R  G  A  K  K  E  G  D  E  I  K  H  R  R  W
    E  *  E  G  E  E  G  P  K  K  K  G  M  K  L  S  T  E  D  G

GGTAAAGAAAAAGTATCAGGGAAAGGGCAAAATAAGAGAAAGCCTTGAGGATAAGAGGG

G  K  E  K  S  I  R  E  R  A  K  *  E  K  A  L  R  I  R  G
   V  K  K  K  V  S  G  K  G  Q  N  K  R  K  P  *  G  *  E  G
    *  R  K  K  Y  Q  G  K  G  K  I  R  E  S  L  E  D  K  R  V

TAGAAGGCTAAAGAACAAGGGGACCACGGGGTCGGGGAAGCGCTGCCTGAACGGCGGGAC

*  K  A  K  E  Q  G  D  H  G  V  G  E  A  L  P  E  R  R  D
   R  R  L  K  N  K  G  T  T  G  S  G  K  R  C  L  N  G  G  T
    E  G  *  R  T  R  G  P  R  G  R  G  S  A  A  *  T  A  G  Q

420
AGTGACAAAAGAAAGGGCGCTGGCGATATTCCGACCAAGGGAAACGCAATCGGGAGGTGA

4381
GGAGGAAGAAGAAGGCCAGGAAGAAGAGGAGGAAGAAGATGAGGGAGCTAAGTCAGACCA

```
G  G  R  R  R  P  G  R  R  G  G  R  R  *  G  S  *  V  R  P
E  E  E  E  G  Q  E  E  E  E  E  E  E  D  E  G  A  K  S  D  Q
 R  K  K  K  A  R  K  K  K  R  R  K  K  M  R  E  L  S  Q  T  K
```

AGCCGAAGAGGGAGGATCCGAGAAGGAAGGCTCTAGTGAAAAGAGGAAGGTGAGCAGGA

```
S  R  R  G  R  I  R  E  G  R  L  *  *  K  R  G  R  *  A  G
 A  E  E  G  G  S  E  K  E  G  S  S  E  K  E  E  G  E  Q  E
  P  K  R  E  D  P  R  R  K  A  L  V  K  K  R  K  V  S  R  K
```

AGAAGGAGAAACAGAAGCTGAAGCTGAAGGAGAGGAAGCCGAAGCTAAAGAGGAAAAGAA

```
R  R  R  N  R  S  *  S  *  R  R  G  S  R  S  *  R  G  K  E
 E  G  E  T  E  A  E  A  E  G  E  E  A  E  A  K  E  E  K  K
  K  E  K  Q  K  L  K  L  K  E  R  K  P  K  L  K  R  K  R  K
```

AGTGGAGGAAAAGAGTGAGGAAGTGGCTACCAAGGAGGAGCTGGTGGCAGATGCCAAGGT

```
S  G  G  K  E  *  G  S  G  Y  Q  G  G  A  G  G  R  C  Q  G
V  E  E  K  S  E  E  V  A  T  K  E  E  L  V  A  D  A  K  V
 W  R  K  R  V  R  K  W  L  P  R  R  S  W  W  Q  M  P  R  W
```

GGAAAAGCCAGAAAAAGCCAAGTCTCCTGTGCCAAAATCACCAGTGGAAGAGAAAGGCAA

```
G  K  A  R  K  S  Q  V  S  C  A  K  I  T  S  G  R  E  R  Q
 E  K  P  E  K  A  K  S  P  V  P  K  S  P  V  E  E  K  G  K
  K  S  Q  K  K  P  S  L  L  C  Q  N  H  Q  W  K  R  K  A  S
```

GTCTCCTGTGCCCAAGTCACCAGTGGAAGAGAAAGGCAAGTCTCCTGTGCCCAAGTCACC

```
V  S  C  A  Q  V  T  S  G  R  E  R  Q  V  S  C  A  Q  V  T
  S  P  V  P  K  S  P  V  E  E  K  G  K  S  P  V  P  K  S  P
   L  L  C  P  S  H  Q  W  K  R  K  A  S  L  L  C  P  S  H  Q
```

```
AGTGGAAGAGAAAGGCAAGTCTCCTGTGCCGAAATCACCAGTGGAAGAGAAAGGCAAGTC
  S   G   R   E   R   Q   V   S   C   A   E   I   T   S   G   R   E   R   Q   V
    V   E   E   K   G   K   S   P   V   P   K   S   P   V   E   E   K   G   K   S
      W   K   R   K   A   S   L   L   C   R   N   H   Q   W   K   R   K   A   S   L
                                                                              4860
TCCTGTGTCAAAATCACCAGTGGAAGAGAAAGCCAAATCTCCTGTGCCAAAATCACCAGT
  S   C   V   K   I   T   S   G   R   E   S   Q   I   S   C   A   K   I   T   S
    P   V   S   K   S   P   V   E   E   K   A   K   S   P   V   P   K   S   P   V
      L   C   Q   N   H   Q   W   K   R   K   P   N   L   L   C   Q   N   H   Q   W
```

```
CCACTCCGGAGTCCTCTGCCCGCTTCCCGACCTCGAGGGTCTCCTCTGACGCGCAGCGTC
```

```
 P  L  R  S  P  L  P  A  S  R  P  R  G  S  P  L  T  R  S  V
  H  S  G  V  L  C  P  L  P  D  L  E  G  L  L  *  R  A  A  S
   T  P  E  S  S  A  R  F  P  T  S  R  V  S  S  D  A  Q  R  R
```

```
GATTCCCCTTCCCTCCTCGGTCCCCTGCCCCGCCCCTCTCACTGCGCGGAGCCGGTCGCC
```

```
 D  S  P  S  L  L  G  P  L  P  R  P  S  H  C  A  E  P  V  A
  I  P  L  P  S  S  V  P  C  P  A  P  L  T  A  R  S  R  S  P
   F  P  F  P  P  R  S  P  A  P  P  L  S  L  R  G  A  G  R  R
```

```
GGGGGGCCGCAGGGGAGGAGGCGGAGAGGCGGGGCCCTCCTCCCCACCCTCTCACTGCCA
```

```
 G  G  P  Q  G  R  R  R  R  G  G  A  L  L  P  T  L  S  L  P
  G  G  R  R  G  G  G  G  E  A  G  P  S  S  P  P  S  H  C  Q
   G  A  A  G  E  E  A  E  R  R  G  P  P  P  H  P  L  T  A  K
```

```
AGGGGTTGGACCCGGCCGCGGCGGCTATAAAAGGGCCGGCGCCCTGGTCGTGCCGCAGTG
```

```
 R  G  W  T  R  P  R  R  L  *  K  G  R  R  P  G  R  A  A  V
  G  V  G  P  G  R  G  G  Y  K  R  A  G  A  L  V  V  P  Q  C
   G  L  D  P  A  A  A  A  I  K  G  P  A  P  W  S  C  R  S  A
```

```
CCTCCCGCCCCGTCCCGGCCTCGCGCACCTGCTCAGGCCATGATGAGCTTCGGCGGCGCG
```

```
 P  P  A  P  S  R  P  R  A  P  A  Q  A  M  M  S  F  G  G  A
  L  P  P  R  P  G  L  A  H  L  L  R  P  *  *  A  S  A  A  R
   S  R  P  V  P  A  S  R  T  C  S  G  H  D  E  L  R  R  R  G
```

```
GACGCGCTGCTGGGCGCCCCGTTCGCGCCGCTGCATGGCGGCGGCAGCCTCCACTACGCG
```

```
 D  A  L  L  G  A  P  F  A  P  L  H  G  G  G  S  L  H  Y  A
  T  R  C  W  A  P  R  S  R  R  C  M  A  A  A  A  S  T  T  R
   R  A  A  G  R  P  V  R  A  A  A  W  R  R  Q  P  P  L  R  A
```

```
CTAGCCCGAAAGGGTGGCGCAGGCGGGACGCGCTCCGCCGCTGGCTCCTCCAGCGGCTTC
```

```
CACTCGTGGACACGGACGTCCGTGAGCTCCGTGTCCGCCTCGCCCAGCCGCTTCCGTGGC

H  S  W  T  R  T  S  V  S  S  V  S  A  S  P  S  R  F  R  G
 T  R  G  H  G  R  P  *  A  P  C  P  P  R  P  A  A  S  V  A
  L  V  D  T  D  V  R  E  L  R  V  R  L  A  Q  P  L  P  W  R

GCAGGCGCCGCCTCAAGCACCGACTCGCTGGACACGCTGAGCAACGGGCCGGAGGGCTGC

A  G  A  A  S  S  T  D  S  L  D  T  L  S  N  G  P  E  G  C
 Q  A  P  P  Q  A  P  T  R  W  T  R  *  A  T  G  R  R  A  A
  R  R  R  L  K  H  R  L  A  G  H  A  E  Q  R  A  G  G  L  H

ATGGTGGCGGTGGCCACCTCACGCAGTGAGAAGGAGCAGCTGCAGGCGCTGAACGACCGC

M  V  A  V  A  T  S  R  S  E  K  E  Q  L  Q  A  L  N  D  R
 W  W  R  W  P  P  H  A  V  R  R  S  S  C  R  R  *  T  T  A
  G  G  G  G  H  L  T  Q  *  E  G  A  A  A  G  A  E  R  P  L

TTCGCCGGGTACATCGACAAGGTGCGGCAGCTGGAGGCGCACAACCGCAGCCTGGAGGGC

F  A  G  Y  I  D  K  V  R  Q  L  E  A  H  N  R  S  L  E  G
 S  P  G  T  S  T  R  C  G  S  W  R  R  T  T  A  A  W  R  A
  R  R  V  H  R  Q  G  A  A  A  G  G  A  Q  P  Q  P  G  G  R

GAGGCTGCGGCGCTGCGGCAGCAGCAGGCGGGCCGCTCCGCTATGGGCGAGCTGTACGAG

E  A  A  A  L  R  Q  Q  Q  A  G  R  S  A  M  G  E  L  Y  E
 R  L  R  R  C  G  S  S  R  R  A  A  P  L  W  A  S  C  T  S
  G  C  G  A  A  A  A  A  G  G  P  L  R  Y  G  R  A  V  R  A

CGCGAGGTCCGCGAGATGCGCGGCGCGGTGCTGCGCCTGGGCGCGGCGCGCGGTCAGCTA

R  E  V  R  E  M  R  G  A  V  L  R  L  G  A  A  R  G  Q  L
 A  R  S  A  R  C  A  A  R  C  C  A  W  A  R  R  A  V  S  Y
  R  G  P  R  D  A  R  R  G  A  A  P  G  R  G  A  R  S  A  T

CGCCTGGAGCAGGAGCACCTGCTCGAGGACATCGCGCACGTGCGCCAGCGCCTAGACGAC

R  L  E  Q  E  H  L  L  E  D  I  A  H  V  R  Q  R  L  D  D
 A  W  S  R  S  T  C  S  R  T  S  R  T  C  A  S  A  *  T  T
  P  G  A  G  A  P  A  R  G  H  R  A  R  A  P  A  P  R  R  R
```

```
GAGGCCCGGCAGCGAGAGGAGGCCGAGGCGGCGGCCCGCGCGCTGGCGCGCTTCGCGCAG

E   A   R   Q   R   E   E   A   E   A   A   A   R   A   L   A   R   F   A   Q
  R   P   G   S   E   R   R   P   R   R   R   P   A   R   W   R   A   S   R   R
   G   P   A   A   R   G   G   R   G   G   G   P   R   A   G   A   L   R   A   G

GAGGCCGAGGCGGCGCGCGTGGACCTGCAGAAGAAGGCGCAGGCGCTGCAGGAGGAGTGC

E   A   E   A   A   R   V   D   L   Q   K   K   A   Q   A   L   Q   E   E   C
  R   P   R   R   R   A   W   T   C   R   R   R   R   R   C   R   R   S   A
   G   R   G   G   A   R   G   P   A   E   E   G   A   G   A   A   G   G   V   R

GGCTACCTGCGGCGCCACCACCAGGAAGAGGTGGGCGAGCTGCTCGGCCAGATCCAGGGC

G   Y   L   R   R   H   H   Q   E   E   V   G   E   L   L   G   Q   I   Q   G
  A   T   C   G   A   T   T   R   K   R   W   A   S   C   S   A   R   S   R   A
   L   P   A   A   P   P   P   G   R   G   G   R   A   A   R   P   D   P   G   L

TCCGGCGCCGCGCAGGCGCAGATGCAGGCCGAGACGCGCGACGCCCTGAAGTGCGACGTG

S   G   A   A   Q   A   Q   M   Q   A   E   T   R   D   A   L   K   C   D   V
  P   A   P   R   R   R   R   C   R   P   R   R   A   T   P   *   S   A   T   *
   R   R   R   A   G   A   D   A   G   R   D   A   R   R   P   E   V   R   R   D

ACGTCGGCGCTGCGCGAGATTCGCGCGCAGCTTGAAGGCCACGCGGTGCAGAGCACGCTG

T   S   A   L   R   E   I   R   A   Q   L   E   G   H   A   V   Q   S   T   L
  R   R   R   C   A   R   F   A   R   S   L   K   A   T   R   C   R   A   R   C
   V   G   A   A   R   D   S   R   A   A   *   R   P   R   G   A   E   H   A   A

CAGTCCGAGGAGTGGTTCCGAG

Partial nucleotide of mRNA and amino acid sequences of various human neuronal proteins expressed in the wild-type and +1 reading frame. The bold-printed nucleotides represent GAGA(G) motifs. The bold-printed peptides were used for immunization. Against ubiquitin[+1] two antibodies were raised (Y-Q and R-Q, both 11 mer).

β amyloid precursor protein (exons 9 and 10):

GAGAGGCTTGAGGCCAAGCACCGAGAGAGAATGTCCCAGGTCATGAGAGAGAATGGGAAGAGGCAGAACGTCAAGCAAAGAACTTGCCTAAA

E  R  L  E  A  K  H  R  E  R  M  S  Q  V  M  R  E  W  E  E  A  E  R  Q  A  K  N  L  P  K    wt

E  A  *  G  Q  A  P  R  E  N  V  P  G  H  E  R  M  G  R  G  R  T  S  S  K  E  L  A  *    +1

Tau (exon 13):

GGGAGATCGTGTACAAGTCGCCAGTGGTCTCGGGGACACGTCTCCACGGCATCTCAGC

G  D  R  V  Q  V  A  S  G  V  W  G  H  V  S  T  A  S  Q  Q

E  I  V  Y  K  S  P  V  V  S  G  D  T  S  P  R  H  L  S

AATGTCTCCTCCACCGGCAGCATGGACATGGTAGACTCGCCCCAGCTCGCCACGCTAGCTGAC

Ubiquitin B (exon 2):

TCTGAGAGTGGTATGCAGATCTTCGTGAAGACCCTGACCGGCAAGACCATCACCCTGGAAGTGGAGCCCAGTGA

L R L R G G M Q V K T L T G K T I T L E V E P S D wt

E R W Y A D L R E D P D R Q * +1

R Q Q D H H P G S G A Q * +1 ubi B 1 ─┴─ ubi B 2

Ubi B 2: antibody used for tables. Ubi B1 also gives rise to staining of tangles. However, its titer is much lower than that of Ubi B 2.

*FIG. 10B*

SEQUENCE LISTING (1) GENERAL INFORMATION:

(iii) NUMBER OF SEQUENCES: 189

(2) INFORMATION FOR SEQ ID NO: 1:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 1:

```
Arg Gly Arg Thr Ser Ser Lys Glu Leu Ala
1               5                   10
```

(2) INFORMATION FOR SEQ ID NO: 2:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 2:

```
His Gly Arg Leu Ala Pro Ala Arg His Ala Ser
1               5                   10
```

(2) INFORMATION FOR SEQ ID NO: 3:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 3:

```
Tyr Ala Asp Leu Arg Glu Asp Pro Asp Arg Gln
1               5                   10
```

(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 4:

```
Arg Gln Asp His His Pro Gly Ser Gly Ala Gln
1               5                   10
```

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 5:

```
Gly Ala Pro Arg Leu Pro Pro Ala Gln Ala Ala
1               5                   10
```

(2) INFORMATION FOR SEQ ID NO: 6:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 6:

```
Lys Thr Arg Phe Gln Arg Lys Gly Pro Ser
1               5                   10
```

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 7:

```
Pro Gly Asn Arg Ser Met Gly His Glu
1               5
```

(2) INFORMATION FOR SEQ ID NO: 8:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 8:

```
Glu Ala Glu Gly Gly Ser Arg Ser
1               5
```

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 9:

```
Val Gly Ala Ala Arg Asp Ser Arg Ala Ala
1               5                   10
```

(2) INFORMATION FOR SEQ ID NO: 10:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 10:

```
ATG CTG CCC GGT TTG GCA CTG CTC CTG CTG GCC GCC TGG ACG GCT CGG     48
Met Leu Pro Gly Leu Ala Leu Leu Leu Leu Ala Ala Trp Thr Ala Arg
1               5                   10                  15
```

```
GCG CTG GAG GTA CCC ACT GAT GGT AAT GCT GGC CTG CTG GCT GAA CCC     96
Ala Leu Glu Val Pro Thr Asp Gly Asn Ala Gly Leu Leu Ala Glu Pro
             20                  25                  30

CAG ATT GCC ATG TTC TGT GGC AGA CTG AAC ATG CAC ATG AAT GTC CAG    144
Gln Ile Ala Met Phe Cys Gly Arg Leu Asn Met His Met Asn Val Gln
         35                  40                  45

AAT GGG AAG TGG GAT TCA GAT CCA TCA GGG ACC AAA ACC TGC ATT GAT    192
Asn Gly Lys Trp Asp Ser Asp Pro Ser Gly Thr Lys Thr Cys Ile Asp
     50                  55                  60

ACC AAG GAA GGC ATC CTG CAG TAT TGC CAA GAA GTC TAC CCT GAA CTG    240
Thr Lys Glu Gly Ile Leu Gln Tyr Cys Gln Glu Val Tyr Pro Glu Leu
 65                  70                  75                  80

CAG ATC ACC AAT GTG GTA GAA GCC AAC CAA CCA GTG ACC ATC CAG AAC    288
Gln Ile Thr Asn Val Val Glu Ala Asn Gln Pro Val Thr Ile Gln Asn
             85                  90                  95

TGG TGC AAG CGG GGC CGC AAG CAG TGC AAG ACC CAT CCC CAC TTT GTG    336
Trp Cys Lys Arg Gly Arg Lys Gln Cys Lys Thr His Pro His Phe Val
        100                 105                 110

ATT CCC TAC CGC TGC TTA GTT GGT GAG TTT GTA AGT GAT GCC CTT CTC    384
Ile Pro Tyr Arg Cys Leu Val Gly Glu Phe Val Ser Asp Ala Leu Leu
    115                 120                 125

GTT CCT GAC AAG TGC AAA TTC TTA CAC CAG GAG AGG                    420
Val Pro Asp Lys Cys Lys Phe Leu His Gln Glu Arg
130                 135                 140
```

(2) INFORMATION FOR SEQ ID NO: 11:

(i) SEQUENCE CHARACTERISTICS:
        (A) LENGTH: 140 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 11:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
             85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg
130                 135                 140
```

(2) INFORMATION FOR SEQ ID NO: 12:

(i) SEQUENCE CHARACTERISTICS:
        (A) LENGTH: 32 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 12:

Trp Lys Ile Thr Leu Gly Arg Thr Gly Trp Gly Thr Gly Lys Ile Arg
1               5                   10                  15

Gly Ala Thr Pro Cys Thr Lys Thr Lys Arg Val Thr Arg Thr Leu Ala
                20                  25                  30

(2) INFORMATION FOR SEQ ID NO: 13:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 13:

Cys Cys Pro Val Trp His Cys Ser Cys Trp Pro Pro Gly Arg Leu Gly
1               5                   10                  15

Arg Trp Arg Tyr Pro Leu Met Val Met Leu Ala Cys Trp Leu Asn Pro
                20                  25                  30

Arg Leu Pro Cys Ser Val Ala Asp
            35                  40

(2) INFORMATION FOR SEQ ID NO: 14:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 14:

Lys Leu Lys Lys Gln Ala Leu Glu Thr Pro Pro Ala Trp Lys Thr Lys
1               5                   10                  15

Leu Leu Val Thr
            20

(2) INFORMATION FOR SEQ ID NO: 15:

(i) SEQUENCE CHARACTERISTICS:
        (A) LENGTH: 21 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 15:

Ala Ala Arg Phe Gly Thr Ala Pro Ala Gly Arg Leu Asp Gly Ser Gly
1               5                   10                  15

Ala Gly Gly Thr His
            20

(2) INFORMATION FOR SEQ ID NO: 16:

(i) SEQUENCE CHARACTERISTICS:
        (A) LENGTH: 1059 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 16:

```
ATG GCT GAG CCC CGC CAG GAG TTC GAA GTG ATG GAA GAT CAC GCT GGG      48
Met Ala Glu Pro Arg Gln Glu Phe Glu Val Met Glu Asp His Ala Gly
1               5                   10                  15

ACG TAC GGG TTG GGG GAC AGG AAA GAT CAG GGG GGC TAC ACC ATG CAC      96
Thr Tyr Gly Leu Gly Asp Arg Lys Asp Gln Gly Gly Tyr Thr Met His
            20                  25                  30

CAA GAC CAA GAG GGT GAC ACG GAC GCT GGC CTG AAA GCT GAA GAA GCA     144
Gln Asp Gln Glu Gly Asp Thr Asp Ala Gly Leu Lys Ala Glu Glu Ala
        35                  40                  45

GGC ATT GGA GAC ACC CCC AGC CTG GAA GAC GAA GCT GCT GGT CAC GTG     192
Gly Ile Gly Asp Thr Pro Ser Leu Glu Asp Glu Ala Ala Gly His Val
50                  55                  60

ACC CAA GCT CGC ATG GTC AGT AAA AGC AAA GAC GGG ACT GGA AGC GAT     240
Thr Gln Ala Arg Met Val Ser Lys Ser Lys Asp Gly Thr Gly Ser Asp
65                  70                  75                  80

GAC AAA AAA GCC AAG GGG GCT GAT GGT AAA ACG AAG ATC GCC ACA CCG     288
Asp Lys Lys Ala Lys Gly Ala Asp Gly Lys Thr Lys Ile Ala Thr Pro
                85                  90                  95

CGG GGA GCA GCC CCT CCA GGC CAG AAG GGC CAG GCC AAC GCC ACC AGG     336
Arg Gly Ala Ala Pro Pro Gly Gln Lys Gly Gln Ala Asn Ala Thr Arg
            100                 105                 110

ATT CCA GCA AAA ACC CCG CCC GCT CCA AAG ACA CCA CCC AGC TCT GGT     384
Ile Pro Ala Lys Thr Pro Pro Ala Pro Lys Thr Pro Pro Ser Ser Gly
        115                 120                 125

GAA CCT CCA AAA TCA GGG GAT CGC AGC GGC TAC AGC AGC CCC GGC TCC     432
Glu Pro Pro Lys Ser Gly Asp Arg Ser Gly Tyr Ser Ser Pro Gly Ser
130                 135                 140

CCA GGC ACT CCC GGC AGC CGC TCC CGC ACC CCG TCC CTT CCA ACC CC      480
Pro Gly Thr Pro Gly Ser Arg Ser Arg Thr Pro Ser Leu Pro Thr Pro
145                 150                 155                 160

CCC ACC CGG GAG CCC AAG AAG GTG GCA GTG GTC CGT ACT CCA CCC AAG     528
Pro Thr Arg Glu Pro Lys Lys Val Ala Val Val Arg Thr Pro Pro Lys
                165                 170                 175

TCG CCG TCT TCC GCC AAG AGC CGC CTG CAG ACA GCC CCC GTG CCC ATG     576
Ser Pro Ser Ser Ala Lys Ser Arg Leu Gln Thr Ala Pro Val Pro Met
            180                 185                 190

CCA GAC CTG AAG AAT GTC AAG TCC AAG ATC GGC TCC ACT GAG AAC CTG     624
Pro Asp Leu Lys Asn Val Lys Ser Lys Ile Gly Ser Thr Glu Asn Leu
        195                 200                 205

AAG CAC CAG CCG GGA GGC GGG AAG GTG CAA ATA GTC TAC AAA CCA GTT     672
Lys His Gln Pro Gly Gly Gly Lys Val Gln Ile Val Tyr Lys Pro Val
210                 215                 220

GAC CTG AGC AAG GTG ACC TCC AAG TGT GGC TCA TTA GGC AAC ATC CAT     720
Asp Leu Ser Lys Val Thr Ser Lys Cys Gly Ser Leu Gly Asn Ile His
225                 230                 235                 240

CAT AAA CCA GGA GGT GGC CAG GTG GAA GTA AAA TCT GAG AAG CTT GAC     768
His Lys Pro Gly Gly Gly Gln Val Glu Val Lys Ser Glu Lys Leu Asp
                245                 250                 255

TTC AAG GAC AGA GTC CAG TCG AAG ATT GGG TCC CTG GAC AAT ATC ACC     816
Phe Lys Asp Arg Val Gln Ser Lys Ile Gly Ser Leu Asp Asn Ile Thr
            260                 265                 270

CAC GTC CCT GGC GGA GGA AAT AAA AAG ATT GAA ACC CAC AAG CTG ACC     864
His Val Pro Gly Gly Gly Asn Lys Lys Ile Glu Thr His Lys Leu Thr
        275                 280                 285

TTC CGC GAG AAC GCC AAA GCC AAG ACA GAC CAC GGG GCG GAG ATC GTG     912
Phe Arg Glu Asn Ala Lys Ala Lys Thr Asp His Gly Ala Glu Ile Val
290                 295                 300
```

| | | | | | | | | | | | | |
|---|---|---|---|---|---|---|---|---|---|---|---|---|
| TAC | AAG | TCG | CCA | GTG | GTG | TCT | GGG | GAC | ACG | TCT | CCA | CGG | CAT | CTC | AGC | 960 |
| Tyr | Lys | Ser | Pro | Val | Val | Ser | Gly | Asp | Thr | Ser | Pro | Arg | His | Leu | Ser | |
| 305 | | | | 310 | | | | | 315 | | | | | 320 | | |

| | | | | | | | | | | | | |
|---|---|---|---|---|---|---|---|---|---|---|---|---|
| AAT | GTC | TCC | TCC | ACC | GGC | AGC | ATC | GAC | ATG | GTA | GAC | TCG | CCC | CAG | CTC | 1008 |
| Asn | Val | Ser | Ser | Thr | Gly | Ser | Ile | Asp | Met | Val | Asp | Ser | Pro | Gln | Leu | |
| | | | | 325 | | | | | 330 | | | | | 335 | | |

| | | | | | | | | | | | | |
|---|---|---|---|---|---|---|---|---|---|---|---|---|
| GCC | ACG | CTA | GCT | GAC | GAG | GTG | TCT | GCC | TCC | CTG | GCC | AAG | CAG | GGT | TTG | 1056 |
| Ala | Thr | Leu | Ala | Asp | Glu | Val | Ser | Ala | Ser | Leu | Ala | Lys | Gln | Gly | Leu | |
| | | 340 | | | | | 345 | | | | | 350 | | | | |

TGA                                                                                                      1059

(2) INFORMATION FOR SEQ ID NO: 17:

(i) SEQUENCE CHARACTERISTICS:
        (A) LENGTH: 352 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 17:

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

```
Phe Arg Glu Asn Ala Lys Ala Lys Thr Asp His Gly Ala Glu Ile Val
    290                 295                 300
Tyr Lys Ser Pro Val Val Ser Gly Asp Thr Ser Pro Arg His Leu Ser
305                 310                 315                 320
Asn Val Ser Ser Thr Gly Ser Ile Asp Met Val Asp Ser Pro Gln Leu
                325                 330                 335
Ala Thr Leu Ala Asp Glu Val Ser Ala Ser Leu Ala Lys Gln Gly Leu
            340                 345                 350
```

(2) INFORMATION FOR SEQ ID NO: 18:

(i) SEQUENCE CHARACTERISTICS:
        (A) LENGTH: 130 amino acids
        (B) TYPE: amino acid
        (C) STRANDEDNESS: double
        (D) TOPOLOGY: unknown (ii) MOLECULE TYPE:peptide (xi) SEQUENCE DESCRIPTION: SEQ ID NO: 18:

```
Pro Lys Leu Ala Trp Ser Val Lys Ala Lys Thr Gly Leu Glu Ala Met
1               5                   10                  15
Thr Lys Lys Pro Arg Gly Leu Met Val Lys Arg Arg Ser Pro His Arg
                20                  25                  30
Gly Glu Gln Pro Leu Gln Ala Arg Ala Arg Pro Thr Pro Pro Gly
            35                  35                  40
Phe Gln Gln Lys Pro Arg Pro Leu Gln Arg His His Pro Ala Leu Val
        50                  55                  60
Asn Leu Gln Asn Gln Gly Ile Ala Ala Ala Thr Ala Ala Pro Ala Pro
65                  70                  75                  80
Gln Ala Leu Pro Ala Ala Pro Ala Pro Arg Pro Phe Gln Pro His
                85                  90                  95
Pro Pro Gly Ser Pro Arg Arg Trp Gln Trp Ser Val Leu His Pro Ser
            100                 105                 110
Arg Arg Leu Pro Pro Arg Ala Ala Cys Arg Gln Pro Pro Cys Pro Cys
            115                 120                 125
Gln Thr
    130
```

(2) INFORMATION FOR SEQ ID NO: 19:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 19:

```
Trp Leu Ser Pro Ala Arg Ser Ser Lys
1               5
```

(2) INFORMATION FOR SEQ ID NO: 20:

(i) SEQUENCE CHARACTERISTICS:
        (A) LENGTH: 7 amino acids
        (B) TYPE:amino acid
        (C) STRANDEDNESS: single
        (D) TOPOLOGY: unknown (ii) MOLECULE TYPE: peptide (xi) SEQUENCE DESCRIPTION: SEQ ID NO: 20:

(2) INFORMATION FOR SEQ ID NO: 21:

(i) SEQUENCE CHARACTERISTICS:
        (A) LENGTH: 34 amino acids
        (B) TYPE: amino acid
        (D) TOPOLOGY: unknown (ii) MOLECULE TYPE: peptide (xi) SEQUENCE DESCRIPTION: SEQ ID NO: 21:

```
His Gly Arg Trp Pro Glu Ser
1               5
```

(2) INFORMATION FOR SEQ ID NO: 21:

(i) SEQUENCE CHARACTERISTICS:
        (A) LENGTH: 34 amino acids
        (B) TYPE: amino acid
        (D) TOPOLOGY: unknown (ii) MOLECULE TYPE: peptide (xi) SEQUENCE DESCRIPTION: SEQ ID NO: 21:

```
Ala Pro Pro Gly Val Arg Ser Asp Gly Arg Ser Arg Trp Asp Val Arg
1               5                   10                  15
Val Gly Gly Gln Glu Arg Ser Gly Gly Leu His His Ala Pro Arg Pro
                20                  25                  30
Arg Gly
```

(2) INFORMATION FOR SEQ ID NO: 22:

(i) SEQUENCE CHARACTERISTICS:
        (A) LENGTH: 707 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 22:

```
ATG CAG ATC TTC GTG AAA ACC CTT ACC GGC AAG ACC ATC ACC CTT GAG        48
Met Gln Ile Phe Val Lys Thr Leu Thr Gly Lys Thr Ile Thr Leu Glu
1               5                   10                  15

GTG GAG CCC AGT GAC ACC ATC GAA AAT GTG AAG GCC AAG ATC CAG GAT        96
Val Glu Pro Ser Asp Thr Ile Glu Asn Val Lys Ala Lys Ile Gln Asp
                20                  25                  30

AAG GAA GGC ATT CCC CCC GAC CAG CAG AGG CTC ATC TTT GCA GGC AAG       144
Lys Glu Gly Ile Pro Pro Asp Gln Gln Arg Leu Ile Phe Ala Gly Lys
            35                  40                  45

CAG CTG GAA GAT GGC CGT ACT CTT TCT GAC TAC AAC ATC CAG AAG GAG       192
Gln Leu Glu Asp Gly Arg Thr Leu Ser Asp Tyr Asn Ile Gln Lys Glu
        50                  55                  60

TCG ACC CTG CAC CTG GTC CTG CGT CTG AGA GGT GGT ATG CAG ATC TTC       240
Ser Thr Leu His Leu Val Leu Arg Leu Arg Gly Gly Met Gln Ile Phe
65                  70                  75                  80

GTG AAG ACC CTG ACC GGC AAG ACC ATC ACC CTG GAA GTG GAG CCC AGT       288
Val Lys Thr Leu Thr Gly Lys Thr Ile Thr Leu Glu Val Glu Pro Ser
                85                  90                  95

GAC ACC ATC GAA AAT GTG AAG GCC AAG ATC CAG GAT AAA GAA GGC ATC       336
Asp Thr Ile Glu Asn Val Lys Ala Lys Ile Gln Asp Lys Glu Gly Ile
            100                 105                 110

CCT CCC GAC CAG CAG AGG CTC ATC TTT GCA GGC AAG CAG CTG GAA GAT       384
Pro Pro Asp Gln Gln Arg Leu Ile Phe Ala Gly Lys Gln Leu Glu Asp
        115                 120                 125

GGC CGC ACT CTT TCT GAC TAC AAC ATC CAG AAG GAG TCG ACC CTG CAC       432
Gly Arg Thr Leu Ser Asp Tyr Asn Ile Gln Lys Glu Ser Thr Leu His
    130                 135                 140

CTG GTC CTG CGT CTG AGA GGT GGT ATG CAG ATC TTC GTG AAG ACC CTG       480
Leu Val Leu Arg Leu Arg Gly Gly Met Gln Ile Phe Val Lys Thr Leu
145                 150                 155                 160

ACC GGC AAG ACC ATC ACT CTG GAA GTG GAG CCC AGT GAC ACC ATC GAA       528
Thr Gly Lys Thr Ile Thr Leu Glu Val Glu Pro Ser Asp Thr Ile Glu
                165                 170                 175
```

```
AAT GTG AAG GCC AAG ATC CAA GAT AAA GAA GGC ATC CCT CCC GAC CAG            576
Asn Val Lys Ala Lys Ile Gln Asp Lys Glu Gly Ile Pro Pro Asp Gln
            180                 185                 190

CAG AGG CTC ATC TTT GCA GGC AAG CAG CTG GAA GAT GGC CGC ACT CTT            624
Gln Arg Leu Ile Phe Ala Gly Lys Gln Leu Glu Asp Gly Arg Thr Leu
            195                 200                 205

TCT GAC TAC AAC ATC CAG AAG GAG TCG ACC CTG CAC CTG GTC CTG CGC            672
Ser Asp Tyr Asn Ile Gln Lys Glu Ser Thr Leu His Leu Val Leu Arg
            210                 215                 220

CTG AGG GGT GGC TGT TAATTCTTCA GTCATGGCAT                                  707
Leu Arg Gly Gly Cys
225
```

(2) INFORMATION FOR SEQ ID NO: 23:

(i) SEQUENCE CHARACTERISTICS:
        (A) LENGTH: 229 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 23:

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
            115                 120                 125

Gly Arg Thr Leu Ser Asp Tyr Asn Ile Gln Lys Glu Ser Thr Leu His
            130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
            165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
            195                 200                 205

Ser Asp Tyr Asn Ile Gln Lys Glu Ser Thr Leu His Leu Val Leu Arg
            210                 215                 220

Leu Arg Gly Gly Cys
225
```

(2) INFORMATION FOR SEQ ID NO: 24:

(i) SEQUENCE CHARACTERISTICS:
        (A) LENGTH: 20 amino acids (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 24:

```
Lys Pro Leu Pro Ala Arg Pro Ser Pro Leu Arg Trp Ser Pro Val Thr
1               5                   10                  15
Pro Ser Lys Met
            20
```

(2) INFORMATION FOR SEQ ID NO: 25:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

```
Cys Arg Ser Ser
1
```

(2) INFORMATION FOR SEQ ID NO: 26:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 26:

```
Gly Gly Ala Gln
1
```

(2) INFORMATION FOR SEQ ID NO: 27:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 27:

```
Ala Asp Leu Arg Glu Asn Pro Tyr Arg Gln Asp His His Pro
1               5                   10
```

(2) INFORMATION FOR SEQ ID NO: 28:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 28:

```
C CCC AGC GGA GGT GAA GGA CGT CCT TCC CCA GGA GCC GAC TGG CCA        46
  Pro Ser Gly Gly Glu Gly Arg Pro Ser Pro Gly Ala Asp Trp Pro
  1               5                   10                  15
ATC ACA GGC AGG AAG ATG AAG GTT CTG TGG GCT GCG TTG CTG GTC ACA      94
```

```
Ile Thr Gly Arg Lys Met Lys Val Leu Trp Ala Ala Leu Leu Val Thr
            20                  25                  30

TTC CTG GCA GGA TGC CAG GCC AAG GTG GAG CAA GCG GTG GAG ACA GAG        142
Phe Leu Ala Gly Cys Gln Ala Lys Val Glu Gln Ala Val Glu Thr Glu
            35                  40                  45

CCG GAG CCC GAG CTG CGC CAG CAG ACC GAG TGG CAG AGC GGC CAG CGC        190
Pro Glu Pro Glu Leu Arg Gln Gln Thr Glu Trp Gln Ser Gly Gln Arg
        50                  55                  60

TGG GAA CTG GCA CTG GGT CGC TTT TGG GAT TAC CTG CGC TGG GTG CAG        238
Trp Glu Leu Ala Leu Gly Arg Phe Trp Asp Tyr Leu Arg Trp Val Gln
    65                  70                  75

ACA CTG TCT GAG CAG GTG CAG GAG GAG CTG CTC AGC TCC CAA GTC ACC        286
Thr Leu Ser Glu Gln Val Gln Glu Glu Leu Leu Ser Ser Gln Val Thr
80                  85                  90                  95

CAA GAA CTG AGG GCG CTG ATG GAC GAG ACC ATG AAG GAG TTG AAG GCC        334
Gln Glu Leu Arg Ala Leu Met Asp Glu Thr Met Lys Glu Leu Lys Ala
                100                 105                 110

TAC AAA TCG GAA CTG GAG GAA CAA CTG ACC CCG GTA GCG GAG GAG ACG        382
Tyr Lys Ser Glu Leu Glu Glu Gln Leu Thr Pro Val Ala Glu Glu Thr
                115                 120                 125

CGG GCA CGG CTG TCC AAG GAG CTG CAG ACG GCG CAG GCC CGG CTG GGC        430
Arg Ala Arg Leu Ser Lys Glu Leu Gln Thr Ala Gln Ala Arg Leu Gly
            130                 135                 140

GCG GAC ATG GAG GAC GTG TGC GGC CGC CTG GTG CAG TAC CGC GGC GAG        478
Ala Asp Met Glu Asp Val Cys Gly Arg Leu Val Gln Tyr Arg Gly Glu
        145                 150                 155

GTG CAG GCC ATG CTC GGC CAG AGC ACC GAG GAG CTG CGG GTG CGC CTC        526
Val Gln Ala Met Leu Gly Gln Ser Thr Glu Glu Leu Arg Val Arg Leu
160                 165                 170                 175

GCC TCC CAC CTG CGC AAG CTG CGT AAG CGG CTC CTC CGC GAT CCC GAT        574
Ala Ser His Leu Arg Lys Leu Arg Lys Arg Leu Leu Arg Asp Pro Asp
                180                 185                 190

GAC CTG CAG AAG CGC CTG GCA GTG TAC CAG GCC GGG GCC CGC GAG GGC        622
Asp Leu Gln Lys Arg Leu Ala Val Tyr Gln Ala Gly Ala Arg Glu Gly
                195                 200                 205

GCC GAG CGC GGC CTC AGC GCC ATC CGC GAG CGC CTG GG                     660
Ala Glu Arg Gly Leu Ser Ala Ile Arg Glu Arg Leu
            210                 215

(2) INFORMATION FOR SEQ ID NO: 29:

(i) SEQUENCE CHARACTERISTICS:
        (A) LENGTH: 220 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 29:

Pro Ser Gly Gly Glu Gly Arg Pro Ser Pro Gly Ala Asp Trp Pro Ile
1               5                   10                  15

Thr Gly Arg Lys Met Lys Val Leu Trp Ala Ala Leu Leu Val Thr Phe
            20                  25                  30

Leu Ala Gly Cys Gln Ala Lys Val Glu Gln Ala Val Glu Thr Glu Pro
        35                  40                  45

Glu Pro Glu Leu Arg Gln Gln Thr Glu Trp Gln Ser Gly Gln Arg Trp
    50                  55                  60

Glu Leu Ala Leu Gly Arg Phe Trp Asp Tyr Leu Arg Trp Val Gln Thr
65                  70                  75                  80

Leu Ser Glu Gln Val Gln Glu Glu Leu Leu Ser Ser Gln Val Thr Gln
```

```
                        85                  90                  95
Glu Leu Arg Ala Leu Met Asp Glu Thr Met Lys Glu Leu Lys Ala Tyr
            100                 105                 110

Lys Ser Glu Leu Glu Glu Gln Leu Thr Pro Val Ala Glu Glu Thr Arg
        115                 120                 125

Ala Arg Leu Ser Lys Glu Leu Gln Thr Ala Gln Ala Arg Leu Gly Ala
    130                 135                 140

Asp Met Glu Asp Val Cys Gly Arg Leu Val Gln Tyr Arg Gly Glu Val
145                 150                 155                 160

Gln Ala Met Leu Gly Gln Ser Thr Glu Glu Leu Arg Val Arg Leu Ala
                165                 170                 175

Ser His Leu Arg Lys Leu Arg Lys Arg Leu Leu Arg Asp Pro Asp Asp
            180                 185                 190

Leu Gln Lys Arg Leu Ala Val Tyr Gln Ala Gly Ala Arg Glu Gly Ala
        195                 200                 205

Glu Arg Gly Leu Ser Ala Ile Arg Glu Arg Leu Gly
    210                 215                 220

(2) INFORMATION FOR SEQ ID NO: 30:

(i) SEQUENCE CHARACTERISTICS:
        (A) LENGTH: 76 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 30:

Arg Phe Cys Gly Leu Arg Cys Trp Ser His Ser Trp Gln Asp Ala Arg
1               5                   10                  15

Pro Arg Trp Ser Lys Arg Trp Arg Gln Ser Arg Ser Pro Ser Cys Ala
            20                  25                  30

Ser Arg Pro Ser Gly Arg Ala Ala Ser Ala Gly Asn Trp His Trp Val
        35                  40                  45

Ala Phe Gly Ile Thr Cys Ala Gly Cys Arg His Cys Leu Ser Arg Cys
    50                  55                  60

Arg Arg Ser Cys Ser Ala Pro Lys Ser Pro Lys Asn
65                  70                  75

(2) INFORMATION FOR SEQ ID NO: 31:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 31:

Pro Ala Glu Val Lys Asp Val Leu Pro Gln Glu Pro Thr Gly Gln Ser
1               5                   10                  15

Gln Ala Gly Arg
            20

(2) INFORMATION FOR SEQ ID NO: 32:

(i) SEQUENCE CHARACTERISTICS:
        (A) LENGTH: 77 amino acids
        (B) TYPE: amino acid
        (C) STRANDEDNESS: single
```

(D) TOPOLOGY: unknown (ii) MOLECULE TYPE: peptide (xi) SEQUENCE DESCRIPTION: SEQ ID NO: 32:

```
Arg Thr Ser Phe Pro Arg Ser Arg Leu Ala Asn His Arg Gln Glu Asp
1               5                   10                  15
Glu Gly Ser Val Gly Cys Val Ala Gly His Ile Pro Gly Arg Met Pro
            20                  25                  30
Gly Gln Gly Gly Ala Ser Gly Gly Asp Arg Ala Gly Ala Arg Ala Ala
        35                  40                  45
Pro Ala Asp Arg Val Ala Glu Arg Pro Ala Leu Gly Thr Gly Thr Gly
50                  55                  60
Ser Leu Leu Gly Leu Pro Ala Leu Gly Ala Asp Thr Val
65                  70                  75
```

(2) INFORMATION FOR SEQ ID NO: 33:

(i) SEQUENCE CHARACTERISTICS:
       (A) LENGTH: 4 amino acids
       (B) TYPE: amino acid
       (C) STRANDEDNESS: single
       (D) TOPOLOGY: unknown (ii) MOLECULE TYPE: protein (xi) SEQUENCE DESCRIPTION: SEQ ID NO: 33:

```
Pro Gln Arg Arg
1
```

(2) INFORMATION FOR SEQ ID NO: 34:

(i) SEQUENCE CHARACTERISTICS:
       (A) LENGTH: 480 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 34:

```
GCA GGG AAG AGT GGT ACC TCA ACA CCC ACT ACC CCT GGG TCT ACT GCC      48
Ala Gly Lys Ser Gly Thr Ser Thr Pro Thr Thr Pro Gly Ser Thr Ala
1               5                   10                  15

ATC ACT CCT GGC ACC CCA CCA AGT TAT TCT TCA CGC ACA CCA GGC ACT      96
Ile Thr Pro Gly Thr Pro Pro Ser Tyr Ser Ser Arg Thr Pro Gly Thr
            20                  25                  30

CCT GGA ACC CCT AGC TAT CCC AGG ACC CCT CAC ACA CCA GGA ACC CCC     144
Pro Gly Thr Pro Ser Tyr Pro Arg Thr Pro His Thr Pro Gly Thr Pro
        35                  40                  45

AAG TCT GCC ATC TTG GTG CCG AGT GAG AAG AAG GTC GCC ATC ATA CGT     192
Lys Ser Ala Ile Leu Val Pro Ser Glu Lys Lys Val Ala Ile Ile Arg
50                  55                  60

ACT CCT CCA AAA TCT CCT GGA CTG ACT CCC AAG CAG CTT CGG CTT ATT     240
Thr Pro Pro Lys Ser Pro Gly Leu Thr Pro Lys Gln Leu Arg Leu Ile
65                  70                  75                  80

AAC CAA CCA CTG CCA GAC CTG AAG AAT GTC AAA TCC AAA ATC GGA TCA     288
Asn Gln Pro Leu Pro Asp Leu Lys Asn Val Lys Ser Lys Ile Gly Ser
                85                  90                  95

ACA GAC AAC ATC AAA TAC CAG CCT AAA GGG GGG CAG GTA CAA ATT GTT     336
Thr Asp Asn Ile Lys Tyr Gln Pro Lys Gly Gly Gln Val Gln Ile Val
            100                 105                 110

ACC AAG AAG ATA GAC CTA AGC CAT GTG ACA TCC AAA TGT GGC TCT CTG     384
Thr Lys Lys Ile Asp Leu Ser His Val Thr Ser Lys Cys Gly Ser Leu
```

```
                     115                 120                 125
AAG  AAC  ATC  CGC  CAC  AGG  CCA  GGT  GGC  GGA  CGT  GTG  AAA  ATT  GAG  AGT       432
Lys  Asn  Ile  Arg  His  Arg  Pro  Gly  Gly  Gly  Arg  Val  Lys  Ile  Glu  Ser
     130                 135                 140

GTA  AAA  CTA  GAT  TTC  AAA  GAA  AAG  GCC  CAA  GCT  AAA  GTT  GGT  TCT  CTT       480
Val  Lys  Leu  Asp  Phe  Lys  Glu  Lys  Ala  Gln  Ala  Lys  Val  Gly  Ser  Leu
145                 150                 155                 160
```

(2) INFORMATION FOR SEQ ID NO: 35:

(i) SEQUENCE CHARACTERISTICS:
        (A) LENGTH: 160 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 35:

```
Ala  Gly  Lys  Ser  Gly  Thr  Ser  Thr  Pro  Thr  Thr  Pro  Gly  Ser  Thr  Ala
1                   5                   10                  15

Ile  Thr  Pro  Gly  Thr  Pro  Pro  Ser  Tyr  Ser  Ser  Arg  Thr  Pro  Gly  Thr
               20                  25                  30

Pro  Gly  Thr  Pro  Ser  Tyr  Pro  Arg  Thr  Pro  His  Thr  Pro  Gly  Thr  Pro
          35                  40                  45

Lys  Ser  Ala  Ile  Leu  Val  Pro  Ser  Glu  Lys  Lys  Val  Ala  Ile  Ile  Arg
     50                  55                  60

Thr  Pro  Pro  Lys  Ser  Pro  Gly  Leu  Thr  Pro  Lys  Gln  Leu  Arg  Leu  Ile
65                  70                  75                  80

Asn  Gln  Pro  Leu  Pro  Asp  Leu  Lys  Asn  Val  Lys  Ser  Lys  Ile  Gly  Ser
               85                  90                  95

Thr  Asp  Asn  Ile  Lys  Tyr  Gln  Pro  Lys  Gly  Gly  Gln  Val  Gln  Ile  Val
          100                 105                 110

Thr  Lys  Lys  Ile  Asp  Leu  Ser  His  Val  Thr  Ser  Lys  Cys  Gly  Ser  Leu
     115                 120                 125

Lys  Asn  Ile  Arg  His  Arg  Pro  Gly  Gly  Gly  Arg  Val  Lys  Ile  Glu  Ser
130                 135                 140

Val  Lys  Leu  Asp  Phe  Lys  Glu  Lys  Ala  Gln  Ala  Lys  Val  Gly  Ser  Leu
145                 150                 155                 160
```

(2) INFORMATION FOR SEQ ID NO: 36:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 36:

```
Leu  Pro  Ser  Ser  Phe  Gly  Leu  Leu  Thr  Asn  His  Cys  Gln  Thr
1                   5                   10
```

(2) INFORMATION FOR SEQ ID NO: 37:

(i) SEQUENCE CHARACTERISTICS:
        (A) LENGTH: 71 amino acids
        (C) STRANDEDNESS: single
        (B) TYPE: amino acid
        (D) TOPOLOGY: unknown (ii) MOLECULE TYPE: peptide (xi) SEQUENCE DESCRIPTION: SEQ ID NO: 37:

Gln Gly Arg Val Val Pro Gln His Pro Leu Pro Leu Gly Leu Leu Pro
1               5                   10                  15

Ser Leu Leu Ala Pro His Gln Val Ile Leu His Ala His Gln Ala Leu
            20                  25                  30

Leu Glu Pro Leu Ala Ile Pro Gly Pro Leu Thr His Gln Glu Pro Pro
        35                  40                  45

Ser Leu Pro Ser Trp Cys Arg Val Arg Arg Ser Pro Ser Tyr Val
    50                  55                  60

Leu Leu Gln Asn Leu Leu Asp
65                  70

(2) INFORMATION FOR SEQ ID NO: 38:

(i) SEQUENCE CHARACTERISTICS:
        (A) LENGTH: 19 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 38:

Leu Ser Gln Asp Pro Ser His Thr Arg Asn Pro Gln Val Cys His Leu
1               5                   10                  15

Gly Ala Glu (2) INFORMATION FOR SEQ ID NO: 39:

(i) SEQUENCE CHARACTERISTICS:
        (A) LENGTH: 35 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 39:

Arg Glu Glu Trp Tyr Leu Asn Thr His Tyr Pro Trp Val Tyr Cys His
1               5                   10                  15

His Ser Trp His Pro Thr Lys Leu Phe Phe Thr His Thr Arg His Ser
            20                  25                  30

Trp Asn Pro
        35

(2) INFORMATION FOR SEQ ID NO: 40:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 40:

```
GCAGCTCCTC GGGCCGTAGC TCGACCCCGC CTTCCCTTTT CCGCAGAATC CTCGCCTTGG      60

CTGCAGCAGC GCGCTGCCCC CACTGGCCGG CGTGCCGTGA TCGATCGCAG GCTGCGTCAG     120

GACCTCCCGG CGTATAAATA GGGGTGGCAG AACGGCGCCG AGCCGCACAC AGCCATCCAT     180

CCTCCCCCTT CCCTCTCTCC CCTGTCCTCT CTCTCCGGGC TCCCACCGCC GCCGGGGAGC     240

ACCGGCCGCC AACCAATGAG TTCCTTCAGC TACGAGCCGT ACTACTCGAC CTCCTACAAG     300
```

```
CGGCGCTACG TGGAGACGCC CCGGGTGCAT ATCAGCGTGC GCAGCGGCTA CAGCACCGCA      360

CGCTCAGCTT ACTCAAGCTA CTCGGCGCCG GTGTCTTCCT CGCTGTCCGT GCGCCGCAGC      420
```

(2) INFORMATION FOR SEQ ID NO: 41:

(i) SEQUENCE CHARACTERISTICS:
        (A) LENGTH: 46 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 41:

```
Ala Ala Pro Arg Ala Val Ala Arg Pro Arg Leu Pro Phe Ser Ala Glu
1               5                   10                  15

Ser Ser Pro Trp Leu Gln Gln Arg Ala Ala Pro Thr Gly Arg Arg Ala
            20                  25                  30

Val Ile Asp Arg Arg Leu Arg Gln Asp Leu Pro Ala Tyr Lys
        35                  40                  45
```

(2) INFORMATION FOR SEQ ID NO: 42:

(i) SEQUENCE CHARACTERISTICS:
        (A) LENGTH: 26 amino acids
        (B) TYPE:amino acid
        (C) STRANDEDNESS: single
        (D) TOPOLOGY: unknown (ii) MOLECULE TYPE:peptide (xi) SEQUENCE DESCRIPTION: SEQ ID NO: 42:

```
Leu Asp Pro Ala Phe Pro Phe Pro Gln Asn Pro Arg Leu Gly Cys Ser
1               5                   10                  15

Ser Ala Leu Pro Pro Leu Ala Gly Val Pro
            20                  25
```

(2) INFORMATION FOR SEQ ID NO: 43:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 43:

```
Gln Leu Leu Gly Pro
1               5
```

(2) INFORMATION FOR SEQ ID NO: 44:

(i) SEQUENCE CHARACTERISTICS:
        (A) LENGTH: 94 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 44:

```
Ile Gly Val Ala Glu Arg Arg Arg Ala Ala His Ser His Pro Ser Ser
1               5                   10                  15

Pro Phe Pro Leu Ser Pro Val Leu Ser Leu Arg Ala Pro Thr Ala Ala
            20                  25                  30
```

Gly Glu His Arg Pro Pro Thr Asn Glu Phe Leu Gln Leu Arg Ala Val
              35                  40                  45

Leu Leu Asp Leu Leu Gln Ala Ala Leu Arg Gly Asp Ala Pro Gly Ala
 50                  55                  60

Tyr Gln Arg Ala Gln Arg Leu Gln His Arg Thr Leu Ser Leu Leu Lys
 65                  70                  75                  80

Leu Leu Gly Ala Gly Val Phe Leu Ala Val Arg Ala Pro Gln
                 85                  90

(2) INFORMATION FOR SEQ ID NO: 45:

(i) SEQUENCE CHARACTERISTICS:
        (A) LENGTH: 44 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 45:

Ser Ser Ser Gly Arg Ser Ser Thr Pro Pro Ser Leu Phe Arg Arg Ile
 1               5                  10                  15

Leu Ala Leu Ala Ala Ala Arg Cys Pro His Trp Pro Ala Cys Arg
                 20                  25                  30

Asp Arg Ser Gln Ala Ala Ser Gly Pro Pro Gly Val
                 35                  40

(2) INFORMATION FOR SEQ ID NO: 46:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 46:

CAGCTGCTTT AAGACAAGGG GTGGGGGAAG GGGAGGGAGG CAAGAAAAGA TGAGGGTGGG      60

GGAGGGGAAA AGAGGGAATG CAAGGGGAAG GAGGGAGGAG ACGGGGAGAA GGAAAGATTG    120

GAAGAAAAGG ATCTCCGAGG AAGGGGCTGA GAGAAGGGCA GGGTGAACTG GACTAAAGGC    180

CAGAGTAGGA AGGAGAAGAG GGGCCAAAAA AGAAGGGGAT GAAATTAAGC ACAGAAGATG    240

GGTAAAGAAA AAAGTATCAG GGAAAGGGCA AAATAAGAGA AAGCCTTGAG GATAAGAGGG    300

TAGAAGGCTA AGAACAAGG GGACCACGGG GTCGGGGAAG CGCTGCCTGA ACGGCGGGAC    360

AGTGACAAAA GAAAGGGCGC TGGCGATATT CCGACCAAGG GAAACGCAAT CGGGAGGTGA    420

(2) INFORMATION FOR SEQ ID NO: 47:

(i) SEQUENCE CHARACTERISTICS:
        (A) LENGTH: 54 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 47:

Ser Cys Phe Lys Thr Arg Gly Gly Gly Arg Gly Gly Arg Gln Glu Lys
 1               5                  10                  15

Met Arg Val Gly Glu Gly Lys Arg Gly Asn Ala Arg Gly Arg Arg Glu
                 20                  25                  30

```
Glu Thr Gly Arg Arg Lys Asp Trp Lys Lys Arg Ile Ser Glu Glu Gly
            35                  40                  45
Ala Glu Arg Arg Ala Gly
 50
```

(2) INFORMATION FOR SEQ ID NO: 48:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 48:

```
Gly Trp Gly Arg Gly Lys Glu Gly Met Gln Gly Glu Gly Gly Arg Arg
 1               5                  10                  15
Arg Gly Glu Gly Lys Ile Gly Arg Lys Gly Ser Pro Arg Lys Gly Leu
            20                  25                  30
Arg Glu Gly Gln Gly Glu Leu Asp
            35                  40
```

(2) INFORMATION FOR SEQ ID NO: 49:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 49:

```
Ala Ala Leu Arg Gln Gly Val Gly Glu Gly Glu Gly Gly Lys Lys Arg
 1               5                  10                  15
```

(2) INFORMATION FOR SEQ ID NO: 50:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 50:

```
Glu Lys Gly Arg Val Asn Trp Thr Lys Gly Gln Ser Arg Lys Glu Lys
 1               5                  10                  15
Arg Gly Gln Lys Arg Arg Gly
            20
```

(2) INFORMATION FOR SEQ ID NO: 51:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 51:

```
Asp Lys Gly Trp Gly Lys Gly Arg Glu Ala Arg Lys Asp Glu Gly Gly
 1               5                  10                  15
Gly Gly Glu Lys Arg Glu Cys Lys Gly Lys Glu Gly Gly Asp Gly Glu
```

```
                    20                  25                  30
Lys Glu Arg Leu Glu Glu Lys Asp Leu Arg Gly Arg Gly
                35                  40                  45

(2) INFORMATION FOR SEQ ID NO: 52:

(i) SEQUENCE CHARACTERISTICS:
        (A) LENGTH: 1162 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 52:

CCACTCCGGA GTCCTCTGCC CGCTTCCCGA CCTCGAGGGT CTCCTCTGAC GCGCAGCGTC     60

GATTCCCCTT CCCTCCTCGG TCCCCTGCCC CGCCCCTCTC ACTGCGCGGA GCCGGTCGCC    120

GGGGGGCCGC AGGGGAGGAG GCGGAGAGGC GGGGCCCTCC TCCCCACCCT CTCACTGCCA    180

AGGGGTTGGA CCCGGCCGCG GCGGCTATAA AAGGGCCGGC GCCCTGGTCG TGCCGCAGTG    240

CCTCCCGCCC CGTCCCGGCC TCGCGCACCT GCTCAGGCCA TGATGAGCTT CGGCGGCGCG    300

GACGCGCTGC TGGGCGCCCC GTTCGCGCCG CTGCATGGCG GCGGCAGCCT CCACTACGCG    360

CTAGCCCGAA AGGGTGGCGC AGGCGGGACG CGCTCCGCCG CTGGCTCCTC CAGCGGCTTC    420

CACTCGTGGA CACGGACGTC CGTGAGCTCC GTGTCCGCCT CGCCCAGCCG CTTCCGTGGC    480

GCAGGCGCCG CCTCAAGCAC CGACTCGCTG ACACGCTGA GCAACGGGCC GGAGGGCTGC     540

ATGGTGGCGG TGGCCACCTC ACGCAGTGAG AAGGAGCAGC TGCAGGCGCT GAACGACCGC    600

TTCGCCGGGT ACATCGACAA GGTGCGGCAG CTGGAGGCGC ACAACCGCAG CCTGGAGGGC    660

GAGGCTGCGG CGCTGCGGCA GCAGCAGGCG GGCCGCTCCG CTATGGGCGA GCTGTACGAG    720

CGCGAGGTCC GCGAGATGCG CGGCGCGGTG CTGCGCCTGG GCGCGGCGCG CGGTCAGCTA    780

CGCCTGGAGC AGGAGCACCT GCTCGAGGAC ATCGCGCACG TGCGCCAGCG CCTAGACGAC    840

GAGGCCCGGC AGCGAGAGGA GGCCGAGGCG GCGGCCCGCG CGCTGGCGCG CTTCGCGCAG    900

GAGGCCGAGG CGGCGCGCGT GGACCTGCAG AAGAAGGCGC AGGCGCTGCA GGAGGAGTGC    960

GGCTACCTGC GGCGCCACCA CCAGGAAGAG GTGGGCGAGC TGCTCGGCCA GATCCAGGGC   1020

TCCGGCGCCG CGCAGGCGCA GATGCAGGCC GAGACGCGCG ACGCCCTGAA GTGCGACGTG   1080

ACGTCGGCGC TGCGCGAGAT TCGCGCGCAG CTTGAAGGCC ACGCGGTGCA GAGCACGCTG   1140

CAGTCCGAGG AGTGGTTCCG AG                                            1162

(2) INFORMATION FOR SEQ ID NO: 53:

(i) SEQUENCE CHARACTERISTICS:
        (A) LENGTH: 69 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 53:

Pro Leu Arg Ser Pro Leu Pro Ala Ser Arg Pro Arg Gly Ser Pro Leu
1               5                   10                  15

Thr Arg Ser Val Asp Ser Pro Ser Leu Leu Gly Pro Leu Pro Arg Pro
                20                  25                  30

Ser His Cys Ala Glu Pro Val Ala Gly Gly Pro Gln Gly Arg Arg Arg
                35                  40                  45
```

```
Arg Gly Gly Ala Leu Leu Pro Thr Leu Ser Leu Pro Arg Gly Trp Thr
    50                  55                  60

Arg Pro Arg Arg Leu
 65

(2) INFORMATION FOR SEQ ID NO: 54:

(i) SEQUENCE CHARACTERISTICS:
        (A) LENGTH: 77 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 54:

Arg Ala Ala Ser Ile Pro Leu Pro Ser Ser Val Pro Cys Pro Ala Pro
 1               5                  10                  15

Leu Thr Ala Arg Ser Arg Ser Pro Gly Gly Arg Arg Gly Gly Gly Gly
                20                  25                  30

Glu Ala Gly Pro Ser Ser Pro Pro Ser His Cys Gln Gly Val Gly Pro
                35                  40                  45

Gly Arg Gly Gly Tyr Lys Arg Ala Gly Ala Leu Val Val Pro Gln Cys
    50                  55                  60

Leu Pro Pro Arg Pro Gly Leu Ala His Leu Leu Arg Pro
 65                  70                  75

(2) INFORMATION FOR SEQ ID NO: 55:

(i) SEQUENCE CHARACTERISTICS:
        (A) LENGTH: 15 amino acids
        (B) TYPE: amino acid
        (D) TOPOLOGY: unknown (ii) MOLECULE TYPE: peptides (xi) SEQUENCE DESCRIPTION: SEQ ID NO: 55:

His Ser Gly Val Leu Cys Pro Leu Pro Asp Leu Glu Gly Leu Leu
 1               5                  10                  15

(2) INFORMATION FOR SEQ ID NO: 56:

(i) SEQUENCE CHARACTERISTICS:
        (A) LENGTH: 181 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 56:

Glu Gly Ala Ala Ala Gly Ala Glu Arg Pro Leu Arg Arg Val His Arg
 1               5                  10                  15

Gln Gly Ala Ala Ala Gly Gly Ala Gln Pro Gln Pro Gly Gly Arg Gly
                20                  25                  30

Cys Gly Ala Ala Ala Ala Ala Gly Gly Pro Leu Arg Tyr Gly Arg Ala
                35                  40                  45

Val Arg Ala Arg Gly Pro Arg Asp Ala Arg Gly Ala Ala Pro Gly
    50                  55                  60

Arg Gly Ala Arg Ser Ala Thr Pro Gly Ala Gly Ala Pro Ala Arg Gly
 65                  70                  75                  80

His Arg Ala Arg Ala Pro Ala Pro Arg Arg Gly Pro Ala Ala Arg
                    85                  90                  95
```

```
Gly Gly Arg Gly Gly Pro Arg Ala Gly Ala Leu Arg Ala Gly Gly
            100                 105                 110
Arg Gly Gly Ala Arg Gly Pro Ala Glu Glu Gly Ala Gly Ala Ala Gly
            115                 120                 125
Gly Val Arg Leu Pro Ala Ala Pro Pro Gly Gly Gly Arg Ala
130                 135                 140
Ala Arg Pro Asp Pro Gly Leu Arg Arg Ala Gly Ala Asp Ala Gly
145                 150                 155                 160
Arg Asp Ala Arg Arg Pro Glu Val Arg Asp Val Gly Ala Ala Arg
                165                 170                 175
Asp Ser Arg Ala Ala
            180
```

(2) INFORMATION FOR SEQ ID NO: 57:

(i) SEQUENCE CHARACTERISTICS:
        (A) LENGTH: 188 amino acids
        (B) TYPE: amino acid
        (D) TOPOLOGY: linear (ii) MOLECULE TYPE: protein (xi) SEQUENCE DESCRIPTION: SEQ ID NO: 57:

```
Thr Pro Glu Ser Ser Ala Arg Phe Pro Thr Ser Arg Val Ser Ser Asp
1               5                   10                  15
Ala Gln Arg Arg Phe Pro Phe Pro Pro Arg Ser Pro Ala Pro Pro Leu
            20                  25                  30
Ser Leu Arg Gly Ala Gly Arg Gly Ala Ala Gly Glu Glu Ala Glu
            35                  40                  45
Arg Arg Gly Pro Pro Pro His Pro Leu Thr Ala Lys Gly Leu Asp Pro
50                  55                  60
Ala Ala Ala Ala Ile Lys Gly Pro Ala Pro Trp Ser Cys Arg Ser Ala
65                  70                  75                  80
Ser Arg Pro Val Pro Ala Ser Arg Thr Cys Ser Gly His Asp Glu Leu
                85                  90                  95
Arg Arg Arg Gly Arg Ala Ala Gly Arg Pro Val Arg Ala Ala Ala Trp
            100                 105                 110
Arg Arg Gln Pro Pro Leu Arg Ala Ser Pro Lys Gly Trp Arg Arg Arg
            115                 120                 125
Asp Ala Leu Arg Arg Trp Leu Leu Gln Arg Leu Pro Leu Val Asp Thr
130                 135                 140
Asp Val Arg Glu Leu Arg Val Arg Leu Ala Gln Pro Leu Pro Trp Arg
145                 150                 155                 160
Arg Arg Arg Leu Lys His Arg Leu Ala Gly His Ala Glu Gln Arg Ala
                165                 170                 175
Gly Gly Leu His Gly Gly Gly His Leu Thr Gln
            180                 185
```

(2) INFORMATION FOR SEQ ID NO: 58:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 58:

GAG AGG CTT GAG GCC AAG CAC CGA GAG AGA ATG TCC CAG GTC ATG AGA     48

```
Glu Arg Leu Glu Ala Lys His Arg Glu Arg Met Ser Gln Val Met Arg
1               5                   10                  15
GAA TGG GAA GAG GCA GAA CGT CAA GCA AAG AAC TTG CCT AAA           90
Glu Trp Glu Glu Ala Glu Arg Gln Ala Lys Asn Leu Pro Lys
            20                  25                  30
```

(2) INFORMATION FOR SEQ ID NO: 59:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 59:

```
Glu Arg Leu Glu Ala Lys His Arg Glu Arg Met Ser Gln Val Met Arg
1               5                   10                  15
Glu Trp Glu Glu Ala Glu Arg Gln Ala Lys Asn Leu Pro Lys
            20                  25                  30
```

(2) INFORMATION FOR SEQ ID NO: 60:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 60:

```
Ala Gln Lys Met Gly Lys Glu Lys Ser Ile Arg Glu Arg Ala Lys
1               5                   10                  15
```

(2) INFORMATION FOR SEQ ID NO: 61:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 61:

```
Gly Gln Ala Pro Arg Glu Asn Val Pro Gly His Glu Arg Met Gly Arg
1               5                   10                  15
Gly Arg Thr Ser Ser Lys Glu Leu Ala
            20                  25
```

(2) INFORMATION FOR SEQ ID NO: 62:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

```
GGAGATCGTG TACAAGTCGC CAGTGGTGTC TGGGGACACG TCTCCACGGC ATCTCAGCAA      60

TGTCTCCTCC ACCGGCAGCA TCGACATGGT AGACTCGCCC CAGCTCGCCA CGCTAGCTGA     120

C                                                                    121
```

(2) INFORMATION FOR SEQ ID NO: 63:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

```
Gly Asp Arg Val Gln Val Ala Ser Gly Val Trp Gly His Val Ser Thr
 1               5                  10                  15

Ala Ser Gln Gln Cys Leu Leu His Arg Gln His Arg His Gly Arg Leu
             20                  25                  30

Ala Pro Ala Arg His Ala Ser
             35
```

(2) INFORMATION FOR SEQ ID NO: 64:

(i) SEQUENCE CHARACTERISTICS:
        (A) LENGTH: 160 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 64:

```
Arg Lys Lys Lys Ala Arg Lys Lys Arg Lys Lys Met Arg Glu Leu
 1               5                  10                  15

Ser Gln Thr Lys Pro Lys Arg Glu Asp Pro Arg Arg Lys Ala Leu Val
             20                  25                  30

Lys Lys Arg Lys Val Ser Arg Lys Lys Glu Lys Gln Lys Leu Lys Leu
             35                  40                  45

Lys Glu Arg Lys Pro Lys Leu Lys Arg Lys Arg Lys Trp Arg Lys Arg
             50                  55                  60

Val Arg Lys Trp Leu Pro Arg Arg Ser Trp Trp Gln Met Pro Arg Trp
65                   70                  75                  80

Lys Ser Gln Lys Lys Pro Ser Leu Leu Cys Gln Asn His Gln Trp Lys
             85                  90                  95

Arg Lys Ala Ser Leu Leu Cys Pro Ser His Gln Trp Lys Arg Lys Ala
             100                 105                 110

Ser Leu Leu Cys Pro Ser His Gln Trp Lys Arg Lys Ala Ser Leu Leu
             115                 120                 125

Cys Arg Asn His Gln Trp Lys Arg Lys Ala Ser Leu Leu Cys Gln Asn
             130                 135                 140

His Gln Trp Lys Arg Lys Pro Asn Leu Leu Cys Gln Asn His Gln Trp
145                 150                 155                 160
```

(2) INFORMATION FOR SEQ ID NO: 65:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 65:

```
Glu Ile Val Tyr Lys Ser Pro Val Val Ser Gly Asp Thr Ser Pro Arg
 1               5                  10                  15
```

```
His Leu Ser Asn Val Ser Ser Thr Gly Ser Ile Asp Met Val Asp Ser
            20                  25                  30

Pro Gln Leu Ala Thr Leu Ala Asp
         35                  40
```

(2) INFORMATION FOR SEQ ID NO: 66:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 66:

```
T CTG AGA GGT GGT ATG CAG ATC TTC GTG AAG ACC CTG ACC GGC AAG          46
  Leu Arg Gly Gly Met Gln Ile Phe Val Lys Thr Leu Thr Gly Lys
  1               5                   10                  15

ACC ATC ACC CTG GAA GTG GAG CCC AGT  GA                                75
Thr Ile Thr Leu Glu Val Glu Pro Ser
                20
```

(2) INFORMATION FOR SEQ ID NO: 67:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 67:

```
Leu Arg Gly Gly Met Gln Ile Phe Val Lys Thr Leu Thr Gly Lys Thr
1               5                   10                  15

Ile Thr Leu Glu Val Glu Pro Ser Asp
            20                  25
```

(2) INFORMATION FOR SEQ ID NO: 68:

(i) SEQUENCE CHARACTERISTICS:
        (A) LENGTH: 160 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 68:

```
Glu Glu Glu Glu Gly Gln Glu Glu Glu Glu Glu Asp Glu Gly Ala
1               5                   10                  15

Lys Ser Asp Gln Ala Glu Gly Gly Ser Glu Lys Glu Gly Ser Ser
            20                  25                  30

Glu Lys Glu Glu Gly Glu Gln Glu Glu Gly Glu Thr Glu Ala Glu Ala
        35                  40                  45

Glu Gly Glu Glu Ala Glu Ala Lys Glu Glu Lys Val Glu Glu Lys
    50                  55                  60

Ser Glu Glu Val Ala Thr Lys Glu Glu Leu Val Ala Asp Ala Lys Val
65                  70                  75                  80

Glu Lys Pro Glu Lys Ala Lys Ser Pro Val Pro Lys Ser Pro Val Glu
            85                  90                  95

Glu Lys Gly Lys Ser Pro Val Pro Lys Ser Pro Val Glu Glu Lys Gly
            100                 105                 110
```

Lys Ser Pro Val Pro Lys Ser Pro Val Glu Glu Lys Gly Lys Ser Pro
            115                 120                 125

Val Pro Lys Ser Pro Val Glu Glu Lys Gly Lys Ser Pro Val Ser Lys
            130                 135                 140

Ser Pro Val Glu Glu Lys Ala Lys Ser Pro Val Pro Lys Ser Pro Val
145                 150                 155                 160

(2) INFORMATION FOR SEQ ID NO: 69:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 69:

Glu Arg Trp Tyr Ala Asp Leu Arg Glu Asp Pro Asp Arg Gln Gln Asp
1               5                   10                  15

His His Pro Gly Ser Gly Ala Gln
            20

(2) INFORMATION FOR SEQ ID NO: 70:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 70:

Met Ser Arg Met Gly Ser Gly Ile Gln Ile His Gln Gly Pro Lys Pro
1               5                   10                  15

Ala Leu Ile Pro Arg Lys Ala Ser Cys Ser Ile Ala Lys Lys Ser Thr
            20                  25                  30

Leu Asn Cys Arg Ser Pro Met Trp
            35                  40

(2) INFORMATION FOR SEQ ID NO: 71:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 71:

Lys Pro Thr Asn Gln
1               5

(2) INFORMATION FOR SEQ ID NO: 72:

(i) SEQUENCE CHARACTERISTICS:
        (A) LENGTH: 19 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 72:

```
Pro Ser Arg Thr Gly Ala Ser Gly Ala Ala Ser Ser Ala Arg Pro Ile
1               5                   10                  15

Pro Thr Leu
```

(2) INFORMATION FOR SEQ ID NO: 73:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 73:

```
Phe Pro Thr Ala Ala
1               5
```

(2) INFORMATION FOR SEQ ID NO: 74:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 74:

```
Leu Val Ser Leu
1
```

(2) INFORMATION FOR SEQ ID NO: 75:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 75:

```
Val Met Pro Phe Ser Phe Leu Thr Ser Ala Asn Ser Tyr Thr Arg Arg
1               5                   10                  15

Gly
```

(2) INFORMATION FOR SEQ ID NO: 76:

(i) SEQUENCE CHARACTERISTICS:
        (A) LENGTH: 83 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 76:

```
Glu Asn Gly Lys Arg Gln Asn Val Lys Gln Arg Thr Cys Leu Lys Leu
1               5                   10                  15

Ile Arg Arg Gln Leu Ser Ser Ile Ser Arg Arg Lys Trp Asn Leu Trp
                20                  25                  30

Asn Arg Lys Gln Pro Thr Arg Asp Ser Ser Trp Trp Arg His Thr Trp
                35                  40                  45

Pro Glu Trp Lys Pro Cys Ser Met Thr Ala Ala Ala Trp Pro Trp Arg
        50                  55                  60
```

```
Thr Thr Ser Pro Leu Cys Arg Leu Phe Leu Leu Gly Leu Val Thr Cys
 65                  70                  75                  80

Ser Ile Cys
```

(2) INFORMATION FOR SEQ ID NO: 77:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 77:

```
Arg Ser Met Ser Ala Gln Asn Arg Arg Thr Asp Ser Thr Pro
 1               5                  10
```

(2) INFORMATION FOR SEQ ID NO: 78:

(i) SEQUENCE CHARACTERISTICS:
        (A) LENGTH: 21 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 78:

```
Ser Ile Ser Ser Met Cys Ala Trp Trp Ile Pro Arg Lys Pro Leu Arg
 1               5                  10                  15

Ser Gly Pro Arg Leu
             20
```

(2) INFORMATION FOR SEQ ID NO: 79:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 79:

```
His Thr Ser Val
 1
```

(2) INFORMATION FOR SEQ ID NO: 80:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 80:

```
Cys Trp Pro Ala Gly
 1               5
```

(2) INFORMATION FOR SEQ ID NO: 81:

(i) SEQUENCE CHARACTERISTICS:
        (A) LENGTH: 32 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 81:

Thr Pro Asp Cys His Val Leu Trp Gln Thr Glu His Ala His Glu Cys
1               5                   10                  15

Pro Glu Trp Glu Val Gly Phe Arg Ser Ile Arg Asp Gln Asn Leu His
                20                  25                  30

(2) INFORMATION FOR SEQ ID NO: 82:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 82:

Tyr Gln Gly Arg His Pro Ala Val Leu Pro Arg Ser Leu Pro
1               5                   10

(2) INFORMATION FOR SEQ ID NO: 83:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 83:

Thr Ala Asp His Gln Cys Gly Arg Ser Gln Pro Thr Ser Asp His Pro
1               5                   10                  15

Glu Leu Val Gln Ala Gly Pro Gln Ala Val Gln Asp Pro Ser Pro Leu
                20                  25                  30

Cys Asp Ser Leu Pro Leu Leu Ser Trp
            35                  40

(2) INFORMATION FOR SEQ ID NO: 84:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 84:

Cys Pro Ser Arg Ser
1               5

(2) INFORMATION FOR SEQ ID NO: 85:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 85:

Gln Val Gln Ile Leu Thr Pro Gly Glu Gly
1               5                   10

(2) INFORMATION FOR SEQ ID NO: 86:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 86:

```
Thr Cys Pro Phe Pro Glu Ser Gln Arg Glu Ala
1               5                   10
```

(2) INFORMATION FOR SEQ ID NO: 87:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 87:

```
Gly Gln Ala Pro Arg Glu Asn Val Pro Gly His Glu Arg Met Gly Arg
1               5                   10                  15

Gly Arg Thr Ser Ser Lys Glu Leu Ala
            20                  25
```

(2) INFORMATION FOR SEQ ID NO: 88:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 88:

```
Glu Gly Ser Tyr Pro Ala Phe Pro Gly Glu Ser Gly Ile Phe Gly Thr
1               5                   10                  15

Gly Ser Ser Gln Arg Glu Thr Ala Ala Gly Gly Asp Thr His Gly Gln
            20                  25                  30

Ser Gly Ser His Ala Gln
            35
```

(2) INFORMATION FOR SEQ ID NO: 89:

(i) SEQUENCE CHARACTERISTICS:
        (A) LENGTH: 69 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 89:

```
Pro Pro Pro Pro Gly Pro Gly Glu Leu His His Arg Ser Ala Gly Cys
1               5                   10                  15

Ser Ser Ser Ala Ser Ser Arg Val Gln Tyr Ala Lys Glu Val Cys Pro
            20                  25                  30

Arg Arg Thr Glu Gly Gln Thr Ala His Pro Lys Ala Phe Arg Ala Cys
            35                  40                  45
```

Ala His Gly Gly Ser Gln Glu Ser Arg Ser Asp Pro Val Pro Gly Tyr
    50                  55                  60

Asp Thr Pro Pro Cys
65

(2) INFORMATION FOR SEQ ID NO: 90:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 90:

Arg Met Ser Ser Pro Arg Ser Ala Pro Leu Arg Thr
1               5                   10

(2) INFORMATION FOR SEQ ID NO: 91:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 91:

Ser Thr Asn Gln Leu Thr
1               5

(2) INFORMATION FOR SEQ ID NO: 92:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 92:

Pro Pro Ser Val Ala His
1               5

(2) INFORMATION FOR SEQ ID NO: 93:

(i) SEQUENCE CHARACTERISTICS:
        (A) LENGTH: 13 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 93:

Ala Thr Ser Ile Ile Asn Gln Glu Val Ala Arg Trp Lys
1               5                   10

(2) INFORMATION FOR SEQ ID NO: 94:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 94:

Asn Leu Arg Ser Leu Thr Ser Arg Thr Glu Ser Ser Arg Arg Leu Gly
1               5                   10                  15

Pro Trp Thr Ile Ser Pro Thr Ser Leu Ala Glu Glu Ile Lys Arg Leu
            20                  25                  30

Lys Pro Thr Ser
        35

(2) INFORMATION FOR SEQ ID NO: 95:

(i) SEQUENCE CHARACTERISTICS:
        (A) LENGTH: 43 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 95:

Pro Ser Ala Arg Thr Pro Lys Pro Arg Gln Thr Thr Gly Arg Arg Ser
1               5                   10                  15

Cys Thr Ser Arg Gln Trp Cys Leu Gly Thr Arg Leu His Gly Ile Ser
            20                  25                  30

Ala Met Ser Pro Pro Pro Ala Ala Ser Thr Trp
        35                  40

(2) INFORMATION FOR SEQ ID NO: 96:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 96:

Thr Arg Pro Ser Ser Pro Arg
1               5

(2) INFORMATION FOR SEQ ID NO: 97:

(i) SEQUENCE CHARACTERISTICS:
        (A) LENGTH: 13 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 97:

Leu Thr Arg Cys Leu Pro Pro Trp Pro Ser Arg Val Cys
1               5                   10

(2) INFORMATION FOR SEQ ID NO: 98:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 98:

Arg Ser Arg His Trp Arg His Pro Gln Pro Gly Arg Arg Ser Cys Trp

```
                    5,958,684
        101                                    102
                          -continued
```

```
1               5              10             15

Ser Arg Asp Pro Ser Ser His Gly Gln
            20              25
```

(2) INFORMATION FOR SEQ ID NO: 99:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 99:

```
Lys Gln Arg Arg Asp Trp Lys Arg
1               5
```

(2) INFORMATION FOR SEQ ID NO: 100:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 100:

```
Gln Lys Ser Gln Gly Gly
1               5
```

(2) INFORMATION FOR SEQ ID NO: 101:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:101:

```
Asn Glu Asp Arg His Thr Ala Gly Ser Ser Pro Ser Arg Pro Glu Gly
1               5                  10                 15

Pro Gly Gln Arg His Gln Asp Ser Ser Lys Asn Pro Ala Arg Ser Lys
            20                 25                 30

Asp Thr Thr Gln Leu Trp
            35
```

(2) INFORMATION FOR SEQ ID NO: 102:

(i) SEQUENCE CHARACTERISTICS:
        (A) LENGTH: 76 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 102:

```
Thr Ser Lys Ile Arg Gly Ser Gln Arg Leu Gln Gln Pro Arg Leu Pro
1               5                  10                 15

Arg His Ser Arg Gln Pro Leu Pro His Pro Val Pro Ser Asn Pro Thr
            20                 25                 30

His Pro Gly Ala Gln Glu Gly Gly Ser Gly Pro Tyr Ser Thr Gln Val
            35                 40                 45
```

Ala Val Phe Arg Gln Glu Pro Pro Ala Asp Ser Pro Arg Ala His Ala
    50                  55                  60

Arg Pro Glu Glu Cys Gln Val Gln Asp Arg Leu His
65                  70                  75

(2) INFORMATION FOR SEQ ID NO: 103:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 103:

Glu Pro Glu Ala Pro Ala Gly Arg Arg Glu Gly Ala Asn Ser Leu Gln
1                   5                   10                  15
Thr Ser (2) INFORMATION FOR SEQ ID NO: 104:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 104:

Pro Glu Gln Gly Asp Leu Gln Val Trp Leu Ile Arg Gln His Pro Ser
1                   5                   10                  15

(2) INFORMATION FOR SEQ ID NO: 105:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 105:

Thr Arg Arg Trp Pro Gly Gly Ser Lys Ile
1                   5                   10

(2) INFORMATION FOR SEQ ID NO: 106:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 106:

Leu Gln Gly Gln Ser Pro Val Glu Asp Trp Val Pro Gly Gln Tyr His
1                   5                   10                  15
Pro Arg Pro Trp Arg Arg Lys
                20

(2) INFORMATION FOR SEQ ID NO: 107:

(i) SEQUENCE CHARACTERISTICS:

(A) LENGTH: 57 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 107:

Asn Pro Gln Ala Asp Leu Pro Arg Glu Arg Gln Ser Gln Asp Arg Pro
1               5                   10                  15

Arg Gly Gly Asp Arg Val Gln Val Ala Ser Gly Val Trp Gly His Val
            20                  25                  30

Ser Thr Ala Ser Gln Gln Cys Leu Leu His Arg Gln His Arg His Gly
        35                  40                  45

Arg Leu Ala Pro Ala Arg His Ala Ser
    50                  55

(2) INFORMATION FOR SEQ ID NO: 108:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 108:

Arg Gly Val Cys Leu Pro Gly Gln Ala Gly Phe Val
1               5                   10

(2) INFORMATION FOR SEQ ID NO: 109:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 109:

Phe Phe Ser His Gly
1               5

(2) INFORMATION FOR SEQ ID NO: 110:

(i) SEQUENCE CHARACTERISTICS:
        (A) LENGTH: 46 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 110:

Arg Pro Arg Ser Arg Ile Arg Lys Ala Phe Pro Pro Thr Ser Arg Gly
1               5                   10                  15

Ser Ser Leu Gln Ala Ser Ser Trp Lys Met Ala Val Leu Phe Leu Thr
            20                  25                  30

Thr Thr Ser Arg Arg Ser Arg Pro Cys Thr Trp Ser Cys Val
        35                  40                  45

(2) INFORMATION FOR SEQ ID NO: 111:

(i) SEQUENCE CHARACTERISTICS:
        (A) LENGTH: 7 amino acids (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO: 111:

Glu Val Val Cys Arg Ser Ser
1               5

(2) INFORMATION FOR SEQ ID NO: 112:

(i) SEQUENCE CHARACTERISTICS:
          (A) LENGTH: 17 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO: 112:

Pro Ala Arg Pro Ser Pro Trp Lys Trp Ser Pro Val Thr Pro Ser Lys
1               5                   10                  15

Met (2) INFORMATION FOR SEQ ID NO: 113:

(i) SEQUENCE CHARACTERISTICS:
          (A) LENGTH: 7 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO: 113:

Glu Val Val Cys Arg Ser Ser
1               5

(2) INFORMATION FOR SEQ ID NO: 114:

(i) SEQUENCE CHARACTERISTICS:
          (A) LENGTH: 17 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO: 114:

Pro Ala Arg Pro Ser Leu Trp Lys Trp Ser Pro Val Thr Pro Ser Lys
1               5                   10                  15

Met (2) INFORMATION FOR SEQ ID NO: 115:

(i) SEQUENCE CHARACTERISTICS:
          (A) LENGTH: 46 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO: 115:

Arg Pro Arg Ser Lys Ile Lys Lys Ala Ser Leu Pro Thr Ser Arg Gly
1               5                   10                  15

Ser Ser Leu Gln Ala Ser Ser Trp Lys Met Ala Ala Leu Phe Leu Thr

```
             20                  25                  30
Thr Thr Ser Arg Arg Ser Arg Pro Cys Thr Trp Ser Cys Ala
         35                  40                  45
```

(2) INFORMATION FOR SEQ ID NO: 116:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 116:

```
Gly Val Ala Val Asn Ser Ser Val Met Ala
 1               5                  10
```

(2) INFORMATION FOR SEQ ID NO: 117:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 117:

```
His His Arg Lys Cys Glu Gly Gln Asp Pro Gly
 1               5                  10
```

(2) INFORMATION FOR SEQ ID NO: 118:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 118:

```
Gly Arg His Ser Pro Arg Pro Ala Glu Ala His Leu Cys Arg Gln Ala
 1               5                  10                  15
Ala Gly Arg Trp Pro Tyr Ser Phe
             20
```

(2) INFORMATION FOR SEQ ID NO: 119:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 119:

```
Leu Gln His Pro Glu Gly Val Asp Pro Ala Pro Gly Pro Ala Ser Glu
 1               5                  10                  15
Arg Trp Tyr Ala Asp Leu Arg Glu Asp Pro Asp Arg Gln Asp His His
             20                  25                  30
Pro Gly Ser Gly Ala Gln
         35
```

(2) INFORMATION FOR SEQ ID NO: 120:

(i) SEQUENCE CHARACTERISTICS:
    (A) LENGTH: 11 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO: 120:

His His Arg Lys Cys Glu Gly Gln Asp Pro Gly
1               5                   10

(2) INFORMATION FOR SEQ ID NO: 121:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 121:

Arg Arg His Pro Ser Arg Pro Ala Glu Ala His Leu Cys Arg Gln Ala
1               5                   10                  15

Ala Gly Arg Trp Pro His Ser Phe
            20

(2) INFORMATION FOR SEQ ID NO: 122:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 122:

Leu Gln His Pro Glu Gly Val Asp Pro Ala Pro Gly Pro Ala Ser Glu
1               5                   10                  15

Arg Trp Tyr Ala Asp Leu Arg Glu Asp Pro Asp Arg Gln Asp His His
            20                  25                  30

Ser Gly Ser Gly Ala Gln
            35

(2) INFORMATION FOR SEQ ID NO: 123:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 123:

His His Arg Lys Cys Glu Gly Gln Asp Pro Arg
1               5                   10

(2) INFORMATION FOR SEQ ID NO: 124:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 124:

Arg Arg His Pro Ser Arg Pro Ala Glu Ala His Leu Cys Arg Gln Ala
1               5                   10                  15
Ala Gly Arg Trp Pro His Ser Phe
            20

(2) INFORMATION FOR SEQ ID NO: 125:

(i) SEQUENCE CHARACTERISTICS:
        (A) LENGTH: 26 amino acids
        (B) TYPE: amino acid
        (C) STRANDEDNESS: single
        (D) TOPOLOGY: unknown (ii) MOLECULE TYPE:peptide (xi) SEQUENCE DESCRIPTION: SEQ ID NO: 125:

Leu Gln His Pro Glu Gly Val Asp Pro Ala Pro Gly Pro Ala Pro Glu
1               5                   10                  15
Gly Trp Leu Leu Ile Leu Gln Ser Trp His
            20                  25

(2) INFORMATION FOR SEQ ID NO: 126:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 126:

Trp Thr Arg Pro
1

(2) INFORMATION FOR SEQ ID NO: 127:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 127:

Arg Pro Thr Asn Arg Asn Trp Arg Asn Asn
1               5                   10

(2) INFORMATION FOR SEQ ID NO: 128:

(i) SEQUENCE CHARACTERISTICS:
        (A) LENGTH: 97 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 128:

Arg Arg Arg Arg Gly His Gly Cys Pro Arg Ser Cys Arg Arg Arg
1               5                   10                  15
Pro Gly Trp Ala Arg Thr Trp Arg Thr Cys Ala Ala Ala Trp Cys Ser
            20                  25                  30

```
Thr Ala Ala Arg Cys Arg Pro Cys Ser Ala Arg Ala Pro Arg Ser Cys
         35                  40                  45
Gly Cys Ala Ser Pro Pro Thr Cys Ala Ser Cys Val Ser Gly Ser Ser
 50                  55                  60
Ala Ile Pro Met Thr Cys Arg Ser Ala Trp Gln Cys Thr Arg Pro Gly
 65                  70                  75                  80
Pro Ala Arg Ala Pro Ser Ala Ala Ser Ala Pro Ser Ala Ser Ala Trp
                 85                  90                  95
Gly
```

(2) INFORMATION FOR SEQ ID NO: 129:

(i) SEQUENCE CHARACTERISTICS:
      (A) LENGTH: 100 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO: 129:

```
Ala Gly Ala Gly Gly Ala Ala Gln Leu Pro Ser His Pro Arg Thr Glu
 1               5                  10                  15
Gly Ala Asp Gly Arg Asp His Glu Gly Val Glu Gly Leu Gln Ile Gly
                 20                  25                  30
Thr Gly Gly Thr Thr Asp Pro Gly Ser Gly Gly Asp Ala Gly Thr Ala
             35                  40                  45
Val Gln Gly Ala Ala Asp Gly Ala Pro Ala Gly Arg Gly His Gly
 50                  55                  60
Gly Arg Val Arg Pro Pro Gly Ala Val Pro Arg Arg Gly Ala Gly His
 65                  70                  75                  80
Ala Arg Pro Glu His Arg Gly Ala Ala Gly Ala Pro Arg Leu Pro Pro
                 85                  90                  95
Ala Gln Ala Ala
            100
```

(2) INFORMATION FOR SEQ ID NO: 130:

(i) SEQUENCE CHARACTERISTICS:
      (A) LENGTH: 7 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO: 130:

```
Ala Ala Pro Pro Arg Ser Arg
 1               5
```

(2) INFORMATION FOR SEQ ID NO: 131:

(i) SEQUENCE CHARACTERISTICS:
      (A) LENGTH: 28 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO: 131:

```
Pro Ala Glu Ala Pro Gly Ser Val Pro Gly Arg Gly Pro Arg Gly Arg
 1               5                  10                  15
```

Arg Ala Arg Pro Gln Arg His Pro Arg Ala Pro Gly
            20                  25

(2) INFORMATION FOR SEQ ID NO: 132:

(i) SEQUENCE CHARACTERISTICS:
        (A) LENGTH: 28 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 132:

Arg Met Ser Asn Pro Lys Ser Asp Gln Gln Thr Thr Ser Asn Thr Ser
1               5                  10                  15
Leu Lys Gly Gly Arg Tyr Lys Leu Leu Pro Arg Arg
            20                  25

(2) INFORMATION FOR SEQ ID NO: 133:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 133:

His Pro Asn Val Ala Leu
1               5

(2) INFORMATION FOR SEQ ID NO: 134:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 134:

Arg Thr Ser Ala Thr Gly Gln Val Ala Asp Val
1               5                  10

(2) INFORMATION FOR SEQ ID NO: 135:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 135:

Lys Leu Arg Val
1

(2) INFORMATION FOR SEQ ID NO: 136:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 136:

Ile Ser Lys Lys Arg Pro Lys Leu Lys Leu Val Leu
1               5                   10

(2) INFORMATION FOR SEQ ID NO: 137:

(i) SEQUENCE CHARACTERISTICS:
         (A) LENGTH: 23 amino acids
         (B) TYPE: amino acid
         (C) STRANDEDNESS: single
         (D) TOPOLOGY: unknown (ii) MOLECULE TYPE: peptide (xi) SEQUENCE DESCRIPTION: SEQ ID NO: 137:

Glu Glu Gly Arg His His Thr Tyr Ser Ser Lys Ile Ser Trp Thr Asp
1               5                   10                  15

Ser Gln Ala Ala Ser Ala Tyr
            20

(2) INFORMATION FOR SEQ ID NO: 138:

(i) SEQUENCE CHARACTERISTICS:
         (A) LENGTH: 23 amino acids
         (B) TYPE: amino acid
         (C) STRANDEDNESS: single
         (D) TOPOLOGY: unknown (ii) MOLECULE TYPE: peptide (xi) SEQUENCE DESCRIPTION: SEQ ID NO: 138:

Pro Thr Thr Ala Arg Pro Glu Glu Cys Gln Ile Gln Asn Arg Ile Asn
1               5                   10                  15

Arg Gln His Gln Ile Pro Ala
            20

(2) INFORMATION FOR SEQ ID NO: 139:

(i) SEQUENCE CHARACTERISTICS:
         (A) LENGTH: 37 amino acids
         (B) TYPE: amino acid
         (C) STRANDEDNESS: single
         (D) TOPOLOGY: unknown (ii) MOLECULE TYPE: peptide (xi) SEQUENCE DESCRIPTION: SEQ ID NO: 139:

Arg Gly Ala Gly Thr Asn Cys Tyr Gln Glu Asp Arg Pro Lys Pro Cys
1               5                   10                  15

Asp Ile Gln Met Trp Leu Ser Glu Glu His Pro Pro Gln Ala Arg Trp
            20                  25                  30

Arg Thr Cys Glu Asn
            35

(2) INFORMATION FOR SEQ ID NO: 140:

(i) SEQUENCE CHARACTERISTICS:
         (A) LENGTH: 12 amino acids
         (B) TYPE: amino acid
         (C) STRANDEDNESS: single
         (D) TOPOLOGY: unknown (ii) MOLECULE TYPE: peptide (xi) SEQUENCE DESCRIPTION: SEQ ID NO: 140:

Glu Cys Lys Thr Arg Phe Gln Arg Lys Gly Pro Ser (2) INFORMATION FOR SEQ ID NO: 141:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 141:

```
Ser Trp Phe Ser
1
```

(2) INFORMATION FOR SEQ ID NO: 142:

(i) SEQUENCE CHARACTERISTICS:
        (A) LENGTH: 93 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 142:

```
Gly Trp Gln Asn Gly Ala Glu Pro His Thr Ala Ile His Pro Pro Pro
1               5                   10                  15
Ser Leu Ser Pro Leu Ser Ser Leu Ser Gly Leu Pro Pro Pro Pro Gly
            20                  25                  30
Ser Thr Gly Arg Gln Pro Met Ser Ser Phe Ser Tyr Glu Pro Tyr Tyr
        35                  40                  45
Ser Thr Ser Tyr Lys Arg Arg Tyr Val Glu Thr Pro Arg Val His Ile
    50                  55                  60
Ser Val Arg Ser Gly Tyr Ser Thr Ala Arg Ser Ala Tyr Ser Ser Tyr
65                  70                  75                  80
Ser Ala Pro Val Ser Ser Ser Leu Ser Val Arg Arg Ser
            85                  90
```

(2) INFORMATION FOR SEQ ID NO: 143:

(i) SEQUENCE CHARACTERISTICS:
        (A) LENGTH: 52 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 143:

```
Ser Ile Ala Gly Cys Val Arg Thr Ser Arg Arg Ile Asn Arg Gly Gly
1               5                   10                  15
Arg Thr Ala Pro Ser Arg Thr Gln Pro Ser Ile Leu Pro Leu Pro Ser
            20                  25                  30
Leu Pro Cys Pro Leu Ser Pro Gly Ser His Arg Arg Arg Gly Ala Pro
        35                  40                  45
Ala Ala Asn Gln
    50
```

(2) INFORMATION FOR SEQ ID NO: 144:

(i) SEQUENCE CHARACTERISTICS:
        (A) LENGTH: 53 amino acids
        (B) TYPE: amino acid (C) STRANDEDNESS: single
        (D) TOPOLOGY: unknown (ii) MOLECULE TYPE: peptide (xi) SEQUENCE DESCRIPTION: SEQ ID NO: 144:

Val Pro Ser Ala Thr Ser Arg Thr Thr Arg Pro Thr Ser Gly Ala
1               5                   10                  15

Thr Trp Arg Arg Pro Gly Cys Ile Ser Ala Cys Ala Ala Thr Ala
            20                  25                  30

Pro His Ala Gln Leu Thr Gln Ala Thr Arg Arg Cys Leu Pro Arg
        35                  40                  45

Cys Pro Cys Ala Ala
        50

(2) INFORMATION FOR SEQ ID NO: 145:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 145:

Trp Thr Lys Ser Leu Phe
1               5

(2) INFORMATION FOR SEQ ID NO: 146:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 146:

Arg Lys Cys Thr Lys Arg Arg Ser Pro Asn Cys Arg Arg Ser Ser
1               5                   10                  15

Thr Arg Arg Ser Pro Trp Arg Trp Thr
            20                  25

(2) INFORMATION FOR SEQ ID NO: 147:

(i) SEQUENCE CHARACTERISTICS:
        (A) LENGTH: 37 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 147:

Pro Ser Pro Thr Phe Pro Pro Arg Ser Arg Thr Ser Ala Arg Ser Thr
1               5                   10                  15

Arg Ser Trp Pro Pro Arg Thr Cys Arg Thr Leu Arg Asn Gly Ser Arg
            20                  25                  30

Ala Ala Ser Arg Cys
        35

(2) INFORMATION FOR SEQ ID NO: 148:

(i) SEQUENCE CHARACTERISTICS:

(A) LENGTH: 37 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 148:

Pro Arg Ala Pro Pro Arg Thr Pro Thr Pro Cys Ala Pro Pro Arg Thr
1               5                   10                  15

Arg Cys Arg Arg Ala Val Val Cys Ser Arg Pro Arg Pro Trp Lys Ser
            20                  25                  30

Lys His Ala Gly Ala
        35

(2) INFORMATION FOR SEQ ID NO: 149:

(i) SEQUENCE CHARACTERISTICS:
        (A) LENGTH: 49 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 149:

Met Lys Arg Trp Arg Ser Ser Cys Arg Ser Trp Arg Thr Ser Arg Thr
1               5                   10                  15

Pro Thr Ser Ala Leu Cys Arg Cys Gly Thr Ala Arg Asn Thr Gly Gly
            20                  25                  30

Arg Gly Thr Arg Ala Arg Gly Gly Val Gly Ala Pro Arg Lys Arg Asn
        35                  40                  45

Gln (2) INFORMATION FOR SEQ ID NO: 150:

(i) SEQUENCE CHARACTERISTICS:
        (A) LENGTH: 49 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 150:

Gly Met Val Gln Glu Pro Leu His Gly Ala Asp Arg Glu Arg Arg Gln
1               5                   10                  15

Glu His Arg Arg Arg Ala Arg Arg Gln Gly Arg Gly Val Gly Glu Pro
            20                  25                  30

Ser Ser Ala Gln Gly Gln Asp Pro Gly Asn Arg Ser Met Pro Gly His
        35                  40                  45

Glu (2) INFORMATION FOR SEQ ID NO: 151:

(i) SEQUENCE CHARACTERISTICS:
        (A) LENGTH: 48 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 151:

Ser Ala Gly Glu Ala Ala Ala Gly Ala Gly Gly Gln Ala Glu Arg Arg

```
           1               5              10              15
His Gln Arg Tyr Ala Gly Ala Ala Arg Pro Glu Thr Gln Gly Gly Gly
                       20              25              30

Glu Leu Glu Gln Gly Gly Glu Leu Val Arg Pro Glu Ser Glu Thr Arg
                35              40              45
```

(2) INFORMATION FOR SEQ ID NO: 152:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 152:

```
Thr Gly Leu Lys Ala Arg Val Gly Arg Arg Arg Gly Ala Lys Lys Glu
 1               5              10              15

Gly Asp Glu Ile Lys His Arg Arg Trp Val Lys Lys Val Ser Gly
                20              25              30

Lys Gly Gln Asn Lys Arg Lys Pro
                35              40
```

(2) INFORMATION FOR SEQ ID NO: 153:

(i) SEQUENCE CHARACTERISTICS:
        (A) LENGTH: 41 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 153:

```
Glu Gly Arg Arg Leu Lys Asn Lys Gly Thr Thr Gly Ser Gly Lys Arg
 1               5              10              15

Cys Leu Asn Gly Gly Thr Val Thr Lys Glu Arg Ala Leu Ala Ile Phe
                20              25              30

Arg Pro Arg Glu Thr Gln Ser Gly Gly
                35              40
```

(2) INFORMATION FOR SEQ ID NO: 154:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 154:

```
Glu Gly Glu Glu Gly Pro Lys Lys Lys Gly Met Lys Leu Ser Thr Glu
 1               5              10              15

Asp Gly
```

(2) INFORMATION FOR SEQ ID NO: 155:

(i) SEQUENCE CHARACTERISTICS:
        (A) LENGTH: 21 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 155:

Arg Lys Lys Tyr Gln Gly Lys Gly Lys Ile Arg Glu Ser Leu Glu Asp
1               5                   10                  15

Lys Arg Val Glu Gly
            20

(2) INFORMATION FOR SEQ ID NO: 156:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 156:

Arg Thr Arg Gly Pro Arg Gly Arg Gly Ser Ala Ala
1               5                   10

(2) INFORMATION FOR SEQ ID NO: 157:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 157:

Thr Ala Gly Gln
1

(2) INFORMATION FOR SEQ ID NO: 158:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 158:

Gln Lys Lys Gly Arg Trp Arg Tyr Ser Asp Gln Gly Lys Arg Asn Arg
1               5                   10                  15

Glu Val (2) INFORMATION FOR SEQ ID NO: 159:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 159:

Glu Lys Ala Leu Arg Ile Arg Gly
1               5

(2) INFORMATION FOR SEQ ID NO: 160:

(i) SEQUENCE CHARACTERISTICS:
        (A) LENGTH: 38 amino acids (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 160:

Lys Ala Lys Glu Gln Gly Asp His Gly Val Gly Glu Ala Leu Pro Glu
1               5                  10                  15

Arg Arg Asp Ser Asp Lys Arg Lys Gly Ala Gly Asp Ile Pro Thr Lys
                20                  25                  30

Gly Asn Ala Ile Gly Arg
            35

(2) INFORMATION FOR SEQ ID NO: 161:

(i) SEQUENCE CHARACTERISTICS:
            (A) LENGTH: 13 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 161:

Gly Gly Arg Arg Arg Pro Gly Arg Arg Gly Gly Arg Arg
1               5                  10

(2) INFORMATION FOR SEQ ID NO: 162:

(i) SEQUENCE CHARACTERISTICS:
            (A) LENGTH: 14 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 162:

Val Arg Pro Ser Arg Arg Gly Arg Ile Arg Glu Gly Arg Leu
1               5                  10

(2) INFORMATION FOR SEQ ID NO: 163:

(i) SEQUENCE CHARACTERISTICS:
            (A) LENGTH: 4 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 163:

Lys Arg Gly Arg
1

(2) INFORMATION FOR SEQ ID NO: 164:

(i) SEQUENCE CHARACTERISTICS:
            (A) LENGTH: 8 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 164:

Ala Gly Arg Arg Arg Asn Arg Ser
1               5

(2) INFORMATION FOR SEQ ID NO: 165:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 165:

```
Arg Arg Gly Ser Arg Ser
1               5
```

(2) INFORMATION FOR SEQ ID NO: 166:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 166:

```
Arg Gly Lys Glu Ser Gly Gly Lys Glu
1               5
```

(2) INFORMATION FOR SEQ ID NO: 167:

(i) SEQUENCE CHARACTERISTICS:
        (A) LENGTH: 94 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 167:

```
Gly Ser Gly Tyr Gln Gly Gly Ala Gly Gly Arg Cys Gln Gly Lys
1               5                   10                  15

Ala Arg Lys Ser Gln Val Ser Cys Ala Lys Ile Thr Ser Gly Arg Glu
                20                  25                  30

Arg Gln Val Ser Cys Ala Gln Val Thr Ser Gly Arg Glu Arg Gln Val
            35                  40                  45

Ser Cys Ala Gln Val Thr Ser Gly Arg Glu Arg Gln Val Ser Cys Ala
    50                  55                  60

Glu Ile Thr Ser Gly Arg Glu Arg Gln Val Ser Cys Val Lys Ile Thr
65                  70                  75                  80

Ser Gly Arg Glu Ser Gln Ile Ser Cys Ala Lys Ile Thr Ser
                85                  90
```

(2) INFORMATION FOR SEQ ID NO: 168:

(i) SEQUENCE CHARACTERISTICS:
        (A) LENGTH: 317 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 168:

```
Lys Gly Arg Arg Pro Gly Arg Ala Ala Val Pro Pro Ala Pro Ser Arg
1               5                   10                  15
```

```
Pro Arg Ala Pro Ala Gln Ala Met Met Ser Phe Gly Gly Ala Asp Ala
            20                  25                  30

Leu Leu Gly Ala Pro Phe Ala Pro Leu His Gly Gly Ser Leu His
            35                  40                  45

Tyr Ala Leu Ala Arg Lys Gly Gly Ala Gly Thr Arg Ser Ala Ala
 50                  55                  60

Gly Ser Ser Ser Gly Phe His Ser Trp Thr Arg Thr Ser Val Ser Ser
 65                  70                  75                  80

Val Ser Ala Ser Pro Ser Arg Phe Arg Gly Ala Gly Ala Ala Ser Ser
                85                  90                  95

Thr Asp Ser Leu Asp Thr Leu Ser Asn Gly Pro Glu Gly Cys Met Val
                100                 105                 110

Ala Val Ala Thr Ser Arg Ser Glu Lys Glu Gln Leu Gln Ala Leu Asn
                115                 120                 125

Asp Arg Phe Ala Gly Tyr Ile Asp Lys Val Arg Gln Leu Glu Ala His
            130                 135                 140

Asn Arg Ser Leu Glu Gly Glu Ala Ala Leu Arg Gln Gln Ala
145                 150                 155                 160

Gly Arg Ser Ala Met Gly Glu Leu Tyr Glu Arg Glu Val Arg Glu Met
                165                 170                 175

Arg Gly Ala Val Leu Arg Leu Gly Ala Ala Arg Gly Gln Leu Arg Leu
            180                 185                 190

Glu Gln Glu His Leu Leu Glu Asp Ile Ala His Val Arg Gln Arg Leu
            195                 200                 205

Asp Asp Glu Ala Arg Gln Arg Glu Glu Ala Glu Ala Ala Arg Ala
            210                 215                 220

Leu Ala Arg Phe Ala Gln Glu Ala Glu Ala Ala Arg Val Asp Leu Gln
225                 230                 235                 240

Lys Lys Ala Gln Ala Leu Gln Glu Glu Cys Gly Tyr Leu Arg Arg His
                245                 250                 255

His Gln Glu Glu Val Gly Glu Leu Leu Gly Gln Ile Gln Gly Ser Gly
                260                 265                 270

Ala Ala Gln Ala Gln Met Gln Ala Glu Thr Arg Asp Ala Leu Lys Cys
                275                 280                 285

Asp Val Thr Ser Ala Leu Arg Glu Ile Arg Ala Gln Leu Glu Gly His
            290                 295                 300

Ala Val Gln Ser Thr Leu Gln Ser Glu Glu Trp Phe Arg
305                 310                 315

(2) INFORMATION FOR SEQ ID NO: 169:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 169:

Ala Ser Ala Ala Arg Thr Arg Cys Trp Ala Pro Arg Ser Arg Cys
1               5                   10                  15

Met Ala Ala Ala Ala Ser Thr Thr Arg
                20                  25

(2) INFORMATION FOR SEQ ID NO: 170:

(i) SEQUENCE CHARACTERISTICS:
```

(A) LENGTH: 26 amino acids
            (B) TYPE: amino acid
            (C) STRANDEDNESS: single
            (D) TOPOLOGY: unknown (ii) MOLECULE TYPE:peptide (xi) SEQUENCE DESCRIPTION: SEQ ID NO: 170:

Pro Glu Arg Val Ala Gln Ala Gly Arg Ala Pro Pro Leu Ala Pro Pro
1               5                   10                  15

Ala Ala Ser Thr Arg Gly His Gly Arg Pro
            20                  25

(2) INFORMATION FOR SEQ ID NO: 171:

(i) SEQUENCE CHARACTERISTICS:
            (A) LENGTH: 24 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 171:

Ala Pro Cys Pro Pro Arg Pro Ala Ala Ser Val Ala Gln Ala Pro Pro
1               5                   10                  15

Gln Ala Pro Thr Arg Trp Thr Arg
            20

(2) INFORMATION FOR SEQ ID NO: 172:

(i) SEQUENCE CHARACTERISTICS:
            (A) LENGTH: 23 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 172:

Ala Thr Gly Arg Arg Ala Ala Trp Trp Arg Trp Pro Pro His Ala Val
1               5                   10                  15

Arg Arg Ser Ser Cys Arg Arg
            20

(2) INFORMATION FOR SEQ ID NO: 173:

(i) SEQUENCE CHARACTERISTICS:
            (A) LENGTH: 80 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO: 173:

Thr Thr Ala Ser Pro Gly Thr Ser Thr Arg Cys Gly Ser Trp Arg Arg
1               5                   10                  15

Thr Thr Ala Ala Trp Arg Ala Arg Leu Arg Arg Cys Gly Ser Ser Arg
            20                  25                  30

Arg Ala Ala Pro Leu Trp Ala Ser Cys Thr Ser Ala Arg Ser Ala Arg
            35                  40                  45

Cys Ala Ala Arg Cys Cys Ala Trp Ala Arg Arg Ala Val Ser Tyr Ala
            50                  55                  60

Trp Ser Arg Ser Thr Cys Ser Arg Thr Ser Arg Thr Cys Ala Ser Ala
65                  70                  75                  80

(2) INFORMATION FOR SEQ ID NO: 174:

(i) SEQUENCE CHARACTERISTICS:
        (A) LENGTH: 77 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 174:

Thr Thr Arg Pro Gly Ser Glu Arg Arg Pro Arg Arg Pro Ala Arg
1               5                   10                  15

Trp Arg Ala Ser Arg Arg Pro Arg Arg Ala Trp Thr Cys Arg
            20                  25                  30

Arg Arg Arg Arg Arg Cys Arg Arg Ser Ala Ala Thr Cys Gly Ala Thr
        35                  40                  45

Thr Arg Lys Arg Trp Ala Ser Cys Ser Ala Arg Ser Arg Ala Pro Ala
    50                  55                  60

Pro Arg Arg Arg Arg Cys Arg Pro Arg Arg Ala Thr Pro
65                  70                  75

(2) INFORMATION FOR SEQ ID NO: 175:

(i) SEQUENCE CHARACTERISTICS:
        (A) LENGTH: 27 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 175:

Arg Arg Arg Cys Ala Arg Phe Ala Arg Ser Leu Lys Ala Thr Arg Cys
1               5                   10                  15

Arg Ala Arg Cys Ser Pro Arg Ser Gly Ser Glu
            20                  25

(2) INFORMATION FOR SEQ ID NO: 176:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 176:

Arg Pro Arg Gly Ala Glu His Ala Ala Val Arg Gly Val Val Pro
1               5                   10                  15

(2) INFORMATION FOR SEQ ID NO: 177:

(i) SEQUENCE CHARACTERISTICS:
        (A) LENGTH: 46 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 177:

Arg Pro Arg Ser Arg Ile Lys Lys Ala Ser Leu Pro Thr Ser Arg Gly
1               5                   10                  15

```
Ser Ser Leu Gln Ala Ser Ser Trp Lys Met Ala Ala Leu Phe Leu Thr
            20                  25                  30

Thr Thr Ser Arg Arg Ser Arg Pro Cys Thr Trp Ser Cys Val
         35                  40                  45
```

(2) INFORMATION FOR SEQ ID NO: 178:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 178:

```
GACAAGTATC TCGAGACACC TGGGGATGAG AATGAACATG CCCATTTCCA GAAAGCCAAA    60

GAGAGGCTTG AGGCCAAGCA CCGAGAGAGA ATGTCCCAGG TCATGAGAGA ATGGGAAGAG   120

GCAGAACGTC AAGCAAAGAA CTTGCCTAAA GCTGATAAGA AGGCAGTTAT CCAGCATTTC   180

CAGGAGAAAG TGGAATCTTT GGAACAGGAA GCAGCCAACG AGAGACAGCA GCTGGTGGAG   240

ACACACATGG CCAGAGTGGA AGCCATGCTC AATGACCGCC GCCGCCTGGC CCTGGAGAAC   300

TACATCACCG CTCTGCAGGC TGTTCCTCCT CGGCCTCGTC ACGTGTTCAA TATGCTAAAG   360

AAGTATGTCC GCGCAGAACA GAAGGACAGA CAGCACACCC TAAAGCATTT CGAGCATGTG   420

CGCATGGTGG ATCCCAAGAA AGCCGCTCAG ATCCGGTCCC AGGTTATGAC ACACCTCCGT   480

GTGATTTATG AGCGCATGAA TCAGTCTCTC TCCCTGCTCT ACAACGTGCC TGCAGTGGCC   540
```

(2) INFORMATION FOR SEQ ID NO: 179:

(i) SEQUENCE CHARACTERISTICS:
        (A) LENGTH: 160 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 179:

```
Asp Lys Tyr Leu Glu Thr Pro Gly Asp Glu Asn Glu His Ala His Phe
1               5                   10                  15

Gln Lys Ala Lys Glu Arg Leu Glu Ala Lys His Arg Glu Arg Met Ser
            20                  25                  30

Gln Val Met Arg Glu Trp Glu Glu Ala Glu Arg Gln Ala Lys Asn Leu
         35                  40                  45

Pro Lys Ala Asp Lys Lys Ala Val Ile Gln His Phe Gln Glu Lys Val
     50                  55                  60

Glu Ser Leu Glu Gln Glu Ala Ala Asn Glu Arg Gln Gln Leu Val Glu
65                  70                  75                  80

Thr His Met Ala Arg Val Glu Ala Met Leu Asn Asp Arg Arg Arg Leu
                85                  90                  95

Ala Leu Glu Asn Tyr Ile Thr Ala Leu Gln Ala Val Pro Pro Arg Pro
            100                 105                 110

Arg His Val Phe Asn Met Leu Lys Lys Tyr Val Arg Ala Glu Gln Lys
         115                 120                 125

Asp Arg Gln His Thr Leu Lys His Phe Glu His Val Arg Met Val Asp
     130                 135                 140

Pro Lys Lys Ala Ala Gln Ile Arg Ser Gln Val Met Thr His Leu Arg
145                 150                 155                 160
```

(2) INFORMATION FOR SEQ ID NO: 180:

(i) SEQUENCE CHARACTERISTICS:
        (A) LENGTH: 34 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 180:

```
Thr Ser Ile Ser Arg His Leu Gly Met Arg Met Asn Met Pro Ile Ser
 1               5                  10                  15

Arg Lys Pro Lys Arg Gly Leu Arg Pro Ser Thr Glu Arg Glu Cys Pro
             20                  25                  30

Arg Ser
```

(2) INFORMATION FOR SEQ ID NO: 181:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 181:

```
Gln Val Ser Arg Asp Thr Trp Gly
 1               5
```

(2) INFORMATION FOR SEQ ID NO: 182:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 182:

```
AGCTTGATGG ACGAAATCTC TTTTCTGAAG AAAGTGCACG AAGAGGAGAT CGCCGAACTG    60
CAGGCGCAGA TCCAGTACGC GCAGATCTCC GTGGAGATGG ACGTGACCAA GCCCGACCTT   120
TCCGCCGCGC TCAAGGACAT CCGCGCGCAG TACGAGAAGC TGGCCGCCAA GAACATGCAG   180
AACGCTGAGG AATGGTTCAA GAGCCGCTTC ACGGTGCTGA CCGAGAGCGC CGCCAAGAAC   240
ACCGACGCCG TGCGCGCCGC CAAGGACGAG GTGTCGGAGA GCCGTCGTCT GCTCAAGGCC   300
AAGACCCTGG AAATCGAAGC ATGCCGGGGC ATGAATGAAG CGCTGGAGAA GCAGCTGCAG   360
GAGCTGGAGG ACAAGCAGAA CGCCGACATC AGCGCTATGC AGGTGCGGCA CGGCCAGAAA   420
CACAGGGGGG CGGGGAACTC GAGCAAGGGG GGGAGTTGGT GCGCCCAGAA AGCGAAACCA   480
GGGGTGGTGC GGCTGCCCAG CTCTTAGGGA TAGGGCTTGG CTCCTTGGCC ACTGTGTGGA   540
```

(2) INFORMATION FOR SEQ ID NO: 183:

(i) SEQUENCE CHARACTERISTICS:
        (A) LENGTH: 160 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 183:

```
Ser Leu Met Asp Glu Ile Ser Phe Leu Lys Lys Val His Glu Glu
1               5                   10                  15

Ile Ala Glu Leu Gln Ala Gln Ile Gln Tyr Ala Gln Ile Ser Val Glu
                20                  25                  30

Met Asp Val Thr Lys Pro Asp Leu Ser Ala Ala Leu Lys Asp Ile Arg
            35                  40                  45

Ala Gln Tyr Glu Lys Leu Ala Ala Lys Asn Met Gln Asn Ala Glu Glu
        50                  55                  60

Trp Phe Lys Ser Arg Phe Thr Val Leu Thr Glu Ser Ala Ala Lys Asn
65                  70                  75                  80

Thr Asp Ala Val Arg Ala Ala Lys Asp Glu Val Ser Glu Ser Arg Arg
                85                  90                  95

Leu Leu Lys Ala Lys Thr Leu Glu Ile Glu Ala Cys Arg Gly Met Asn
                100                 105                 110

Glu Ala Leu Glu Lys Gln Leu Gln Glu Leu Glu Asp Lys Gln Asn Ala
            115                 120                 125

Asp Ile Ser Ala Met Gln Val Arg His Gly Gln Lys His Arg Gly Ala
            130                 135                 140

Gly Asn Ser Ser Lys Gly Gly Ser Trp Cys Ala Gln Lys Ala Lys Pro
145                 150                 155                 160

(2) INFORMATION FOR SEQ ID NO: 184:

(i) SEQUENCE CHARACTERISTICS:
        (A) LENGTH: 61 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 184:

Leu Asp Gly Arg Asn Leu Phe Ser Glu Glu Ser Ala Arg Arg Gly Asp
1               5                   10                  15

Arg Arg Thr Ala Gly Ala Asp Pro Val Arg Ala Asp Leu Arg Gly Asp
                20                  25                  30

Gly Arg Asp Gln Ala Arg Pro Phe Arg Arg Ala Gln Gly His Pro Arg
            35                  40                  45

Ala Val Arg Glu Ala Gly Arg Gln Glu His Ala Glu Arg
        50                  55                  60

(2) INFORMATION FOR SEQ ID NO: 185:

(i) SEQUENCE CHARACTERISTICS:
        (A) LENGTH: 480 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 185:

GGAGGAAGAA GAAGGCCAGG AAGAAGAGGA GGAAGAAGAT GAGGGAGCTA AGTCAGACCA        60

AGCCGAAGAG GGAGGATCCG AGAAGGAAGG CTCTAGTGAA AAAGAGGAAG GTGAGCAGGA       120

AGAAGGAGAA ACAGAAGCTG AAGCTGAAGG AGAGGAAGCC GAAGCTAAAG AGGAAAAGAA       180

AGTGGAGGAA AAGAGTGAGG AAGTGGCTAC CAAGGAGGAG CTGGTGGCAG ATGCCAAGGT       240

GGAAAAGCCA GAAAAAGCCA AGTCTCCTGT GCCAAAATCA CCAGTGGAAG AGAAAGGCAA       300

GTCTCCTGTG CCCAAGTCAC CAGTGGAAGA GAAAGGCAAG TCTCCTGTGC CCAAGTCACC       360
```

```
AGTGGAAGAG AAAGGCAAGT CTCCTGTGCC GAAATCACCA GTGGAAGAGA AAGGCAAGTC    420

TCCTGTGTCA AAATCACCAG TGGAAGAGAA AGCCAAATCT CCTGTGCCAA AATCACCAGT    480
```

(2) INFORMATION FOR SEQ ID NO: 186:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 186:

```
Ser Thr Ser Arg Glu Ala Gly Arg Cys Lys
1               5                   10
```

(2) INFORMATION FOR SEQ ID NO: 187:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 187:

```
Ala Lys Lys Ser Pro Val Lys Ala Thr Ala Pro Glu Val Lys Glu Glu
1               5                   10                  15

Glu Gly Glu Lys
            20
```

(2) INFORMATION FOR SEQ ID NO: 188:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 188:

```
Pro Lys Ser Leu Gln
1               5
```

(2) INFORMATION FOR SEQ ID NO: 189:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 189:

```
Lys Gln Leu His Leu Lys Leu Lys Lys Arg Lys Gly Lys Arg
1               5                   10
```

DIAGNOSIS OF NEURODEGENERATIVE DISEASE

This application claims the benefit of U.S. Provisional Application No. 60/009,832, filed Jan. 1, 1996.

BACKGROUND OF THE INVENTION

Many diseases are believed to stem from somatic genetic mutation rather than inherited gene abnormalities, including different types of cancers and neurodegenerative diseases.

Diseases which are caused by somatic mutation are often age-related, with an increasing incidence of somatic mutation with increasing age. For example, the prevalence of cancer increases with age, and it appears that some cancers are caused by somatic mutation. Cancer is the second leading cause of death in the United States, accounting for approximately 500,000 deaths (or 20 percent of all deaths) per year. These diseases are so prevalent that unless current trends are reversed, one in three living Americans will develop cancer at some time. Cancers are usually detected by clinical methods and cytological methods and are difficult to detect early. In some cases, familial cancers have been traced to inherited genes, and detection of such genes is believed to be predictive of susceptibility to the cancer.

It is an object of the present invention to provide methods and assays for detection and/or treatment of diseases involving genetic mutations, particularly those diseases relating to aging, wherein the probability of having the disease increases with the age of the patient. The invention contemplates detection and/or treatment of those age related diseases which are due to mutations occurring in the DNA of somatic cells. If the mutations are not corrected, the disease may result.

Another object of the invention is to treat diseases identified according to the invention, by providing to a patient afflicted with the disease or having a propensity to develop the disease, a corrective agent such as an enzyme or oligonucleotide.

Yet another object of the invention is to provide a method for identifying age-related diseases by correlating nucleotide sequence mutation hotspots with the disease.

Other objects of the invention relate to identification, detection and treatment of age related diseases including cancers (especially non-hereditary cancers) and neurodegenerative diseases, such as Alzhemier's Disease (AD), Parkinson's Disease (PD), Down's syndrome, frontal lobe dementia (Pick's Disease), progressive supranuclear palsy (PSP), amyotrophic lateral sclerosis, Huntington's Disease, multiple sclerosis, and other degenerative diseases. Early disease diagnosis is important for effective treatment.

Alzheimer's Disease is in most cases a disease which is related to aging. AD is characterised by atrophy of nerve cells in the cerebral cortex, subcortical areas, and hippocampus and the presence of plaques, dystrophic neurites and neurofibrillary tangles. In most cases, it is not known whether AD is caused by a genetically inherited trait or by environmental factors, e.g., somatic mutations, or both. The pathogenic mutation is unknown.

Another object of the invention is to provide a diagnostic test for AD which enables definitive diagnosis of AD in living patients. Furthermore, as AD is a progressive disease, it is desirable to diagnose AD as early as possible so that preventative action may be taken.

A number of diagnostic methods have been previously suggested for AD diagnosis, most of which have focused on the amyloid protein. See for example U.S. Pat. Nos. 4,666,829, 4,816,416 and 4,933,159. However, amyloid deposits have been found in individuals, especially aged persons, who have not shown signs of dementia (See J. Biol. Chem., 265, pp 15977, 1990; and Tables 2 and 3). Diagnostic tests based on the amyloid protein have therefore been shown to lack specificity for AD.

In U.S. Pat. No. 4,727,041 a diagnostic test for AD is described based on measuring levels of somatotropin and somatomedin-C in blood sera following administration of an L-dopa proactive test.

In International patent application WO 94/02851, a method is described for identifying AD by the use of antibodies having affinity for paired helical filaments in order to determine the levels of paired helical filaments in cerebral spinal fluid. The presence of paired helical filaments is alleged to be indicative of AD.

Other diagnostic methods are based on the identification of "disease specific marker proteins" in the cerebral spinal fluid. In International patent application WO 95/05604, for example, five disease specific proteins are identified by their molecular weights. However, the specific identity of the proteins is unknown and their specific relationship to the pathogenesis of AD is also unknown. The five "disease specific marker proteins" may therefore be present as a result of a more fundamental cellular or biochemical change.

Another object of the invention is to provide for detection of AD preferably early on in the disease state. It is desirable to detect a protein or substance which is either directly responsible for the disease or is involved early on in the pathogenesis of the disease, or if not involved is nevertheless generated directly or indirectly by the mechanism causing the disease. Such a protein or substance may be the "causative" agent to the disease or may be "associated with" the disease state in the sense of being diagnostic of the disease state.

Recently, Sherrington et al. in Nature, 375, pp 254–260, 1995, identified a gene on chromosome 14 bearing missense mutations which are associated with up to 70% of familial early onset AD cases. A missense mutation involves a nucleotide substitution, usually a single nucleotide substitution, which results in an amino acid substitution at the corresponding codon. The missense mutations disclosed in Sherrington et al. are predicted to change the encoded amino acid at the following positions (numbering from the first putative initiation codon) Met to Leu at codon 146, His to Arg at codon 163, Ala to Glu at codon 246, Leu to Val at codon 286, Cys to Tyr at codon 410. It has been proposed that these mutations may be useful in identifying early onset AD. As stated earlier, the majority of AD cases are late onset (after 65 years of age; Table 1) and it is therefore still a problem to identify the majority of individuals having AD, particularly late onset AD.

Presently, there are a number of substances which are alleged to be useful in the treatment of AD. However, so far only limited success has been achieved with these substances. Methods for effectively treating and/or preventing AD are still required (see Allen and Burns, Journal of Psychopharmacology, 9, pp 43–56, 1995).

SUMMARY OF THE INVENTION

The present invention is based on the observation that a gene containing a frameshift mutation and encoding a corresponding mutant protein may be correlated with the presence of a disease.

According to the present invention there is provided a method for the diagnosis of a disease caused by or associated with at least one gene having one or more somatic mutations giving rise to a frameshift mutation comprising: i. providing a biological sample, such as a body fluid or tissue sample, from a patient; and ii. analyzing the sample for the presence of a gene having a frameshift mutation or a mutant protein encoded thereby, wherein the presence of the mutated gene or mutant protein is indicative of the disease.

The term "somatic mutation" refers to a mutation occurring in a somatic or non-germline cell, and does not pass through the germline and is therefore not inherited.

A "mutant" protein is a polypeptide encoded by a mRNA at least a part of which is in a reading frame that is shifted relative to the initiation start codon from that of the native or wild-type reading frame, and thus will include any protein having an aberrant carboxy terminal portion which is encoded by the +1 or +2 reading frame of the wild type gene sequence. Thus, the mutant protein will include a hybrid wild-type/nonsense protein having an amino terminal amino acid sequence that is encoded by the wild type (O) reading frame and a carboxy terminal amino acid sequence that is encoded by the +1 or +2 reading frame, and thus the nonsense portion of the mutant protein. The cross-over point between the wild type and nonsense amino acid sequences is the codon containing the frameshift mutation.

The invention is based on the discovery of the presence of such a mutant protein or an accumulation of more than one mutant protein in a tissue from a diseased individual, and also on identification of the mutant protein as indicative of the disease.

The phrase "caused by or associated with" refers to a gene which is either fully or partly responsible for the disease, or a gene which is not responsible for the disease but is associated with the diseased state in the sense that it is diagnostic of the diseased state.

A disease caused by or associated with at least one gene having one or more somatic mutations giving rise to a frameshift mutation can be any disease including non-hereditary cancers, neurodegenerative diseases such as Parkinson's Disease (PD), Alzheimer's Disease (AD), Down's syndrome, frontal lobe dementia (Pick's Disease), progressive supranuclear palsy (PSP), amyotrophic lateral sclerosis, Huntington's Disease, multiple sclerosis, and other degenerative diseases such as cardiovascular diseases and rheumatoid arthritis. Cancers treatable according to the invention include but are not limited to Hodgkin's disease, acute and chronic lymphocytic leukemias, multiple myeloma, breast, ovary, lung, and stomach or bladder cancers.

A gene having a somatic mutation which leads to a frameshift mutation, and herein referred to as the "mutant gene", can be any gene having at least one mutation which leads to a frameshift mutation.

A "frameshift mutation" refers to a deletion or insertion of one or more nucleotides within an open reading frame, for example, a single nucleotide or dinucleotide deletion or insertion, such that the reading frame of the coding region is shifted by one or two nucleotides. Preferably, the frameshift mutation is a nucleotide or dinucleotide deletion leading to a +1 or +2 frameshift mutation. However, any number of nucleotide deletions can occur provided a frameshift mutation results. Alternatively, the insertion of one or more nucleotides may give rise to a frameshift and such mutations also form part of the present invention.

Other genetic modifications which give rise to a frameshift also form part of the present invention, such as a change in the nucleotide sequence which leads to translation initiation from a different position or a mutation outside a coding region, such as within an Intron or a 5' or 3' untranslated region, which mutation may result in mis-translation and production of a mutant protein. In this type of gene mutation, the mutant protein would be completely nonsense sequences and would contain no wild-type sequences.

It is preferred that the mutation is a nucleotide and more preferably a dinucleotide deletion or insertion associated with the nucleotide sequence GAGA of the gene; especially preferred frameshift mutations are associated with the nucleotide sequence GAGAX, where X is one of G, A, T or C; thus preferred motifs include GAGAG, GAGAC, GAGAA, and GAGAT. Preferably the dinucleotide deletion is an AG deletion. It is further preferred that the mutant gene has one or two dinucleotide deletions associated with a GAGA, GAGAG, GAGAC, GAGAA, or GAGAT leading to a +1 or +2 frameshift mutation respectively.

In a preferred embodiment of the invention, the somatic mutations occur in genes of the neuronal system, where the disease is a neurodegenerative disease.

The "neuronal system" is defined as any cells, genes, proteins or substances relating to or forming part of the neuronal system such as nerve cells, glial cells, proteins including Tau, β amyloid precursor protein, ubiquitin, apolipoprotein E4 neurofilament proteins and microtubule associated protein II, and the genes encoding the proteins.

Where the disease is a neurodegenerative disease, especially AD, the preferred mutant genes of the present invention are those encoding the β amyloid precursor protein, the Tau protein, ubiquitin, apolipoprotein-$E_4$ (Apo-$E_4$), microtubule associated protein II (MAP 2) and the neurofilament proteins, having a deletion, insertion or other modification leading to a frameshift mutation. The most preferred mutant genes of the present invention are those encoding ubiquitin, MAP 2 and the neurofilament proteins, having a frameshift mutation.

It is preferred that the mutation is an AG dinucleotide deletion associated with a GAGA, or GAGAX leading to a frameshift mutation. It is further preferred that the mutant gene has one or two AG deletions each associated with a GAGA or similar motif, leading to a +1 or +2 frameshift mutation respectively.

The term "mutant protein" as used herein is defined as the protein encoded by the mutant gene of the present invention.

It is preferred that the methods of the present invention are for the diagnosis of a disease caused by or associated with at least one gene having one or more somatic mutations giving rise to a frameshift mutation. A preferred disease for diagnosis by the present invention is AD, except the early onset AD cases found to be linked to chromosome 14 and 1. It is further preferred that the methods of the present invention are for the diagnosis of late onset AD, especially non-familial or "sporadic" late onset AD cases.

As used herein, "biological sample" refers to a body fluid or body tissue which contains proteins and/or cells from which nucleic acids and proteins can be isolated. Preferred sources include buccal swabs, blood, sperm, epithelial or other tissue, milk, urine, cerebrospinal fluid, sputum, fecal matter, lung aspirates, throat swabs, genital swabs and exudates, rectal swabs, and nasopharyngeal aspirates.

The body fluid sample can be any body fluid which contains cells having the somatic mutation which gives rise to the frameshift mutation and causes the diseases. When the disease is a neurodegenerative disease it is preferred that the body fluid sample contains cells of the neuronal system or the products of such cells. When the disease is a neurodegenerative disease, the preferred body fluid is cerebral spinal fluid which can be obtained after a lumbar puncture (Lannfelt et al., Nature Medicine, 1, pp 829–832, 1995). Another preferred body fluid is blood, as it is easily obtained and contains lymphocytes which can be analyzed for the presence of the mutant gene or encoded protein.

The tissue sample can be any tissue and is preferably one that can be easily obtained, such as skin and nose epithelium.

Preferably, when analyzing the sample for a mutant gene, a nucleic acid probe is used. The nucleic acid probe is preferably a nucleotide probe having a sequence complementary to part of the mutant gene encompassing the mutation giving rise to the frameshift mutation.

As would be apparent to one skilled in the art, the probe may be used to detect DNA or RNA in a fluid sample or in a tissue sample.

The present invention further provides a nucleic acid probe having a sequence complementary to part of the mutant gene encompassing the mutation leading to the frameshift mutation. The probe is preferably sufficiently complementary to the mutant sequence of the gene so that under stringent conditions the probe only remains bound to the mutant sequence. "Stringent" conditions are defined herein as DNA:DNA hybridization conditions which may be performed at 65° C. using a hybridization buffer equivalent to 50% formamide and 0.1× SSC (see below and Evans et al. PNAS (1994) 9; 6059–6063, 6060). "Stringent" conditions also preferably include stringent washes, as described in Evans et al. (Ibid).

The probe may be of any length but is preferably between 5 and 50 nucleotides long, more preferably between 10 and 30 nucleotides long. For example, the probe may be 5, 10, 15, 20, 25, or 30 nucleotides in length.

In a preferred embodiment the probe comprises a sequence complementary to a GAGA or GAGAX, having a nucleotide or dinucleotide deletion or insertion, and nucleotide sequences corresponding to the nucleotide sequences flanking the GAGA or motif in the wild-type gene. It would be apparent to one skilled in the art that if RNA was being probed for, a probe comprising a sequence complementary to the corresponding GAGA motif present in the RNA would have to be used.

Methods of detecting the presence of the mutant gene include the polymerase chain reaction (PCR) using primers having a sequence complementary to the sequence either side of the mutation which gives rise to the frameshift mutation are used to amplify the DNA, as described hereinbelow.

The primers used in the above PCR based method can vary in size from 20 bp to 2–3 kb; for example, 20 bp, 50 bp, 100 bp, 500 bp, 1000 bp, 1500 bp, 2000 bp, or 3000 bp. The primers can be prepared by a number of standard techniques including cloning the sequences flanking the nucleotide region to be amplified or by synthesizing the primers using phosphoramidite method.

The present invention further provides primers for use in the above defined PCR based methods for the amplification of the nucleotide region containing the mutation.

Preferably, when analyzing the sample for the mutant protein of the present invention an immunological test is employed. The immunological test is preferably based on the use an antibody molecule having specificity for the mutant protein of the present invention and not the wild-type protein.

The present invention thus further provides an antibody molecule having specificity for the mutated protein of the present invention but not for the wild-type protein. Prefereably, the antibody is specific for the carboxy terminal end of the mutant protein.

The present invention further provides a method for the diagnosis of a neurodegenerative disease comprising: i. providing a body fluid or tissue sample from a patient; and ii. analyzing the sample for the presence of a gene of the neuronal system having a frameshift mutation or a protein encoded thereby, wherein the presence of the mutated gene is indicative of a neurodegenerative disease.

Preferably, the neurodegenerative disease is AD.

The present invention also relates to methods for preventing and/or treating the diseases, vectors for preventing and/or treating the diseases and for the production of diagnostic reagents, compositions for preventing and/or treating the diseases, nucleic acid sequences, probes and antibody molecules for use in the present invention and transgenic animals.

The present invention further provides a diagnostic kit for diagnosing a disease caused by or associated with at least one gene having one or more somatic mutations giving rise to a frameshift mutation comprising: i. a nucleic acid probe having a sequence complementary to part of the mutant gene which encompasses the mutation which leads to the frameshift mutation and packaging materials therefor; and ii. means for detecting the probe bound to the mutant gene.

The present invention further provides a diagnostic kit for diagnosing a disease caused by or associated with at least one gene having one or more somatic mutations giving rise to a frameshift mutation comprising: i. primers for use in a PCR reaction, the primers having a sequence complementary to the sequence either side of the mutation which gives rise to the frameshift mutation, packaging materials therefor, and reagents necessary for performing a PCR reaction and amplifying the DNA or RNA sequence containing the mutation; and ii. means for detecting the amplified DNA or RNA sequence containing the mutation.

The present invention further provides a diagnostic kit for diagnosing a disease caused by or associated with at least one gene having one or more somatic mutations giving rise to a frameshift mutation comprising: i. an antibody molecule having specificity for the mutant protein of the present invention and not the wild-type protein; and ii. means for detecting the antibody molecule bound to the mutant protein.

The antibody molecule and the means for detecting the bound antibody molecule are as defined above.

In a further embodiment of the present invention the diagnostic kit described above additionally comprising: i. an antibody molecule having specificity for the wild-type protein; and ii. means for detecting the antibody molecule bound to the wild-type protein, as a control for diagnosing a disease caused by or associated with at least one gene having one or more somatic mutations giving rise to a frameshift mutation.

The present invention further provides a gene having one or more somatic mutations giving rise to a frameshift mutation which causes or is associated with a disease.

The present invention further provides a mutated protein encoded by the mutated gene found to be indicative of a disease, the mutant gene having one or more somatic mutations giving rise to a frameshift mutation. Preferably, the mutant protein contains an antigenic epitope specific for the diseased state, examples of which are provided in Table 7.

In a preferred embodiment of the present invention the mutated gene encodes a protein comprising at least part of the sequence designated +1 or +2 in any one of FIGS. 2 to 9, or an immunologically equivalent fragment thereof.

In a preferred embodiment the mutated protein comprises any one of the following individual sequences: RGRTSSKELA; HGRLAPARHAS; YADLREDPDRQ; RQDHHPGSGAQ; GAPRLPPAQAA; KTRFQRKGPS; PGNRSMGHE; EAEGGSRS; or VGAARDSRAA, (Seq. ID Nos: 1–9, respectively) especially when the disease is a neurodegenerative disease such as AD.

In a preferred embodiment, the antibody molecule of the present invention has affinity for the mutant proteins defined above.

The present invention also relates to a method for treating and/or preventing a disease caused by or associated with at least one gene having one or more somatic mutations giving rise to a frameshift mutation. The finding of mutations in genes which lead to the production of mutant proteins, and which are indicative of a disease, has led to a number of ways of treating and/or preventing the disease.

The present invention further provides a method for detecting errors in nucleic acid repair mechanisms comprising: i. providing a body fluid or tissue sample from a patient; and ii. analyzing the sample for the presence of a gene having a frameshift mutation or a protein encoded thereby, the presence of a mutation being indicative of an error in the nucleic acid repair mechanisms.

The correction of the mutations found in the mutant genes of the present invention is therefore a valuable method for combatting diseases.

The present invention further provides methods of treating a disease by administering to a patient an expression vector encoding one or more DNA repair enzymes.

The present invention further provides the use of an expression vector encoding one or more repair enzymes in the manufacture of a composition for the treatment of a disease caused by or associated with at least one gene having one or more somatic mutations giving rise to a frameshift mutation.

The present invention further provides a method of treatment and/or prevention of a disease caused by or associated with at least one gene having one or more somatic mutations giving rise to a frameshift mutation, comprising administering an expression vector encoding one or more repair enzymes to a patient suffering from or likely to suffer from the disease.

The present invention further provides an expression vector encoding one or more repair enzymes.

The repair enzymes encoded by the vector can be any repair enzyme and/or an associated protein (see Kunkel, Current Biology, 1995, Vol. 5, No. 10, p.1091–1094); such as, for example, a G/T mismatch binding protein (GTBP or p160), which are capable of or contribute to the repair of a somatic mutation which leads to a frameshift mutation, such as a dinucleotide deletion. Preferred repair enzymes include Mut H, Mut S, Mut L, and Mut U, and the homologs thereof, including mammalian homologs. Such homologs include MSH 1–6, PMS 1–2, MLH 1 and GTBP.

The invention also encompasses methods of combatting diseases caused by at least one gene having one or more somatic mutations giving rise to a frameshift mutation by targeting the mRNA transcript transcribed from the mutated gene, and correcting the mutant mRNA using ribozymes.

Accordingly, the present invention further provides methods of treating the disease by administering an expression vector encoding a ribozyme in therapy.

The present invention further provides the use of an expression vector encoding a ribozyme in the manufacture of a composition for the treatment of a disease caused by at least one gene having one or more somatic mutations giving rise to a frameshift mutation.

The present invention further provides a method of treatment and/or prevention of a disease caused by at least one gene having one or more somatic mutations giving rise to a frameshift mutation, comprising administering an expression vector encoding a ribozyme under the control of a promoter to a patient suffering from or likely to suffer from the disease.

The present invention further provides an expression vector encoding a ribozyme under the control of a promoter.

The ribozyme encoded by the vector is preferably specific for RNA containing the mutations described above or for the RNA encoding a defective repair enzyme. For example, if a defect in a repair enzyme has lead to the mutated gene, by correcting the transcribed message from the repair enzyme gene the function of the repair enzyme can be restored.

A further method for combatting a disease caused by or associated with at least one gene having one or more somatic mutations giving rise to a frameshift mutation, is by gene therapy.

A vector encoding a non-mutated version of the mutated gene under the control of a promoter and other selected transcriptional or translational control elements can be delivered to affected or susceptible cells leading to the production of the correct protein in the cell. By increasing the percentage of the correct protein produced in relation to the mutated protein the further progression of the disease will be reduced, prevented and possibly reversed.

The present invention further provides methods of treating a disease by administering an expression vector encoding the wild-type version of the mutated gene.

The present invention further provides the use of an expression vector encoding the wild-type version of the mutated gene in the manufacture of a composition for treating a disease caused by or associated with at least one gene having one or more somatic mutations giving rise to a frameshift mutation.

The present invention further provides a method of treatment and/or prevention of a disease caused by or associated with at least one gene having one or more somatic mutations giving rise to a frameshift mutation, comprising administering an expression vector encoding the wild-type version of the mutated gene to a patient suffering from or likely to suffer from the disease.

The present invention further provides an expression vector encoding the wild-type version of the mutated gene.

The present invention also provides a vector encoding a wild-type version of the defective repair enzyme which has lead to or contributed to the presence of the mutated gene which causes or is associated with a disease, under the control of a promoter.

Preferably the wild-type repair enzyme is MSH 1–6, PMS 1–2 or MLH 1, or an associated protein such as GTBP.

The present invention further provides the use of more than one of the vectors of the present invention in any combination in therapy.

The present invention further provides the use of more than one of the vectors of the present invention in any combination in the treatment and/or prevention of a disease caused by or associated with at least one gene having one or more somatic mutations giving rise to a frameshift mutation.

The pharmaceutical compositions of the present invention in addition to the vectors as defined herein may additionally comprise a pharmaceutically acceptable excipient.

The invention also encompasses host cell lines and transgenic animals wherein the somatic cells of the animal and the DNA of the host cell contains a transgene which is a mutant gene having one or more somatic mutations giving rise to a frameshift mutation.

Preferably, the transgenic animals of the present invention are additionally defective in nucleic acid repair mechanisms. Thus, the mutated gene specifically expressed in this type of transgenic animal will not be repaired.

The present invention further provides an animal having somatic cells containing at least one of the mutated genes of the present invention.

Preferably, the animal is a rodent, more preferably a rat or mouse.

As used herein, and "expression vector" or an "expressible gene" denotes a vector containing a gene, or a gene which is expressible in a selected host cell. The gene will therefore be operatively associated with transcriptional and translational control sequences sufficient to permit expression of the gene in the host cell. Such control sequences include but are not limited to a promoter, and enhancer, a locus control region, a ribosome binding site, a polyadenylation site and a transcription termination site.

The present invention further provides a method for identifying diseases caused by or associated with at least one gene having one or more somatic mutations giving rise to a frameshift mutation. The method comprises: i. providing the sequence of a gene suspected of being involved in the pathogenesis of a disease; ii. identifying the sequence of the mutant protein encoded by the gene sequence following a frameshift mutation; iii. preparing a probe to the mutant protein or a fragment thereof; and iv. probing a body fluid or tissue sample from a patient having the disease and a patient not having the disease, in order to find a correlation between the presence of the mutant protein and the diseased state.

Preferably, the probe is an antibody molecule as defined herein. It is further preferred that the antibody molecule has affinity for a protein comprising at least one of the sequences: RGRTSSKELA (SEQ ID NO:1); HGRLAPARHAS (SEQ ID NO:2); YADLREDPDRQ (SEQ ID NO:3); RQDHHPGSGAQ (SEQ ID NO:4); GAPRLPPAQAA (SEQ ID NO:5); KTRFQRKGPS (SEQ ID NO:6); PGNRSMGHE (SEQ ID NO:7); EAEGGSRS (SEQ ID NO:8); or VGAARDSRAA (SEQ ID NO:9), especially when the disease is a neurodegenerative disease such as AD.

Other features and advantages of the invention will be apparent from the following description of the preferred embodiments thereof, and from the claims.

DESCRIPTION OF DRAWINGS

The invention is now illustrated in the appended example with reference to the following drawings:

FIG. 2 presents the coding nucleotide sequence of the human myloid A4 gene (SEQ ID NO:10 and 178), the amino acid sequence of the wild-type protein (SEQ ID NO:11 and 179), the mutant +1 frameshift protein (SEQ ID NO.15, 80–89 and 181) and the mutant +2 frameshift protein (SEQ ID NO:13, 70–79 and 180).

FIG. 3 presents the coding nucleotide sequence of the human microtubule-associated protein tau gene (SEQ ID NO:16), the amino acid sequence of the wild-type protein (SEQ ID NO:17), the mutant +1 frameshift protein (SEQ ID NO:20, 21 and 8–108) and the mutant +2 frameshift protein (SEQ ID NO:12, 14, 18, 19, 90–97 and 186).

FIG. 4 presents the coding nucleotide sequence of the human ubiquitin gene (SEQ ID NO:22), the amino acid sequence of the wild-type protein (SEQ ID NO:23 and 109), the mutant +1 frameshift protein (SEQ ID NO:26, 27 and 117–125) and the mutant +2 frameshift protein (SEQ ID NO:24, 25, 110–116 and 177).

FIG. 5 presents the coding nucleotide sequence of the human apolipoprotein E gene (SEQ ID NO:28), the amino acid sequence of the wild-type protein (SEQ ID NO:29), the mutant +1 frameshift protein (SEQ ID NO:32, 33 and 129–131) and the mutant +2 frameshift protein (SEQ ID NO: 30, 31 and 126–128). Information concerning restriction enzyme sites is also given.

FIG. 6 presents the coding nucleotide sequence of the human microtubule-associated protein 2 (SEQ ID NO:34), the amino acid sequence of the wild-type protein (SEQ ID NO:35), the mutant +1 frameshift protein (SEQ ID NO:38, 39 and 137–140) and the mutant +2 frameshift protein (SEQ ID NO:36, 37 and 132–136).

Figure 7A:
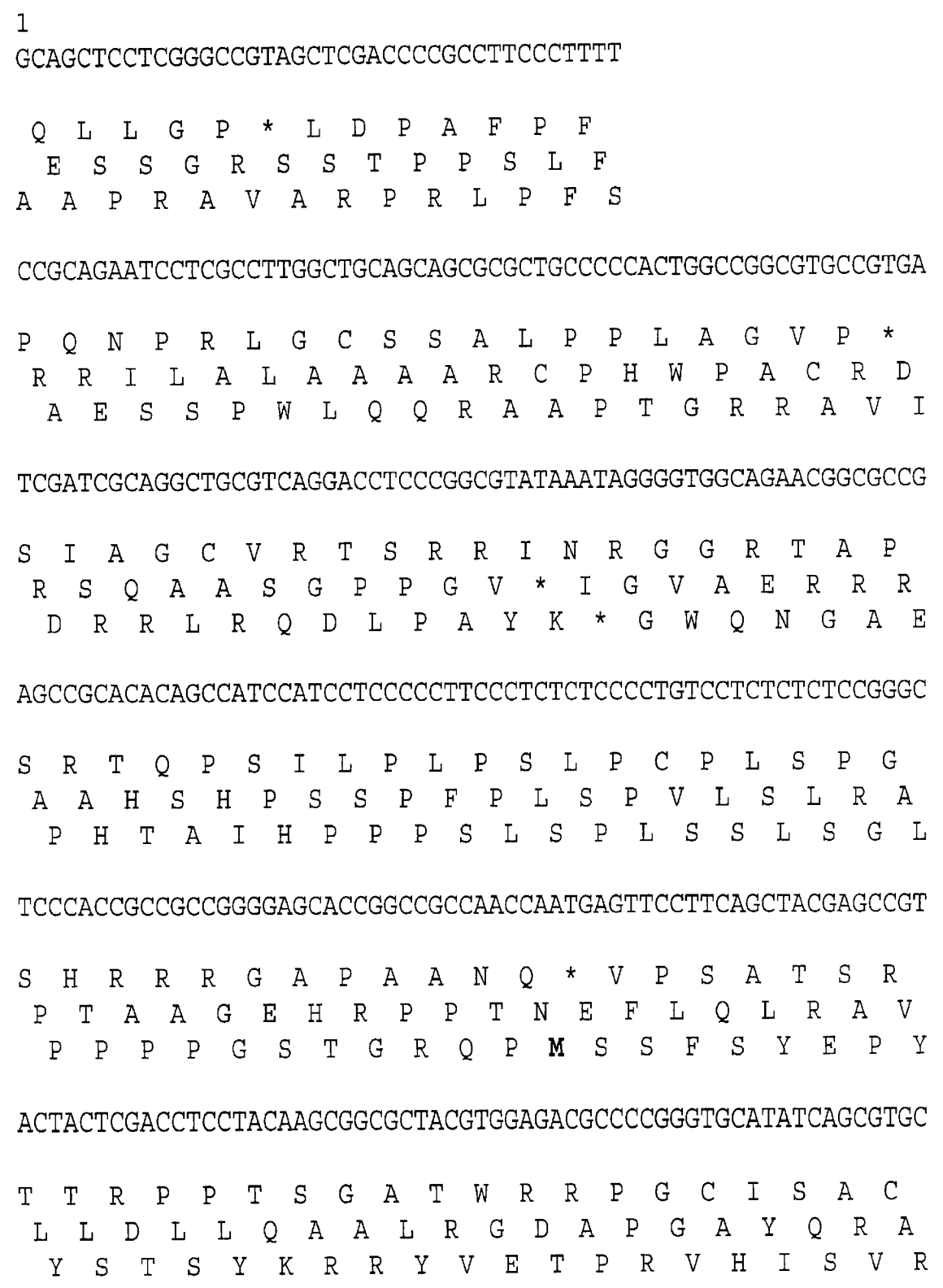

FIG. 7 presents the coding nucleotide sequence of the human neurofilament subunit NF-low (SEQ ID NO:40 and 182), the amino acid sequence of the wild-type protein (SEQ ID NO:41, 142 and 183), the mutant +1 frameshift protein (SEQ ID NO:44, 45, 150, 151 and 184) and the mutant +2 frameshift protein (SEQ ID NO:42, 43, 143–149).

FIG. 8 presents the coding nucleotide sequence of the human neurofilament subunit NF-M (SEQ ID NO:46 and 185), the amino acid sequence of the wild-type protein (SEQ ID NO:47, 68, 152, 153 and 187), the mutant +1 frameshift protein (SEQ ID NO:50, 51 and 158–167) and the mutant +2 frameshift protein (SEQ ID NO:48, 49, 64, 154–158, 188 and 189).

FIG. 9 presents the coding nucleotide sequence of the human neurofilament subunit NF-H (SEQ ID NO:52), the amino acid sequence of the wild-type protein (SEQ ID NO:53 and 168), the mutant +1 frameshift protein (SEQ ID NO:56, 57 and 176) and the mutant +2 frameshift protein (SEQ ID NO:54, 55 and 169–175).

FIG. 10 presents the partial mRNA nucleotide sequence and amino acid sequence of three human neuronal proteins (β amyloid precursor protein (exons 9 and 10) SEQ ID NO:58, 59 and 61), Tau (exon 13) SEQ ID NO:62, 63 and 65 and Ubiquitin B (exon 2 SEQ ID NO:66, 67 and 65)) expressed in the wildtype and +1 reading frame.

DESCRIPTION

Figure 1A:
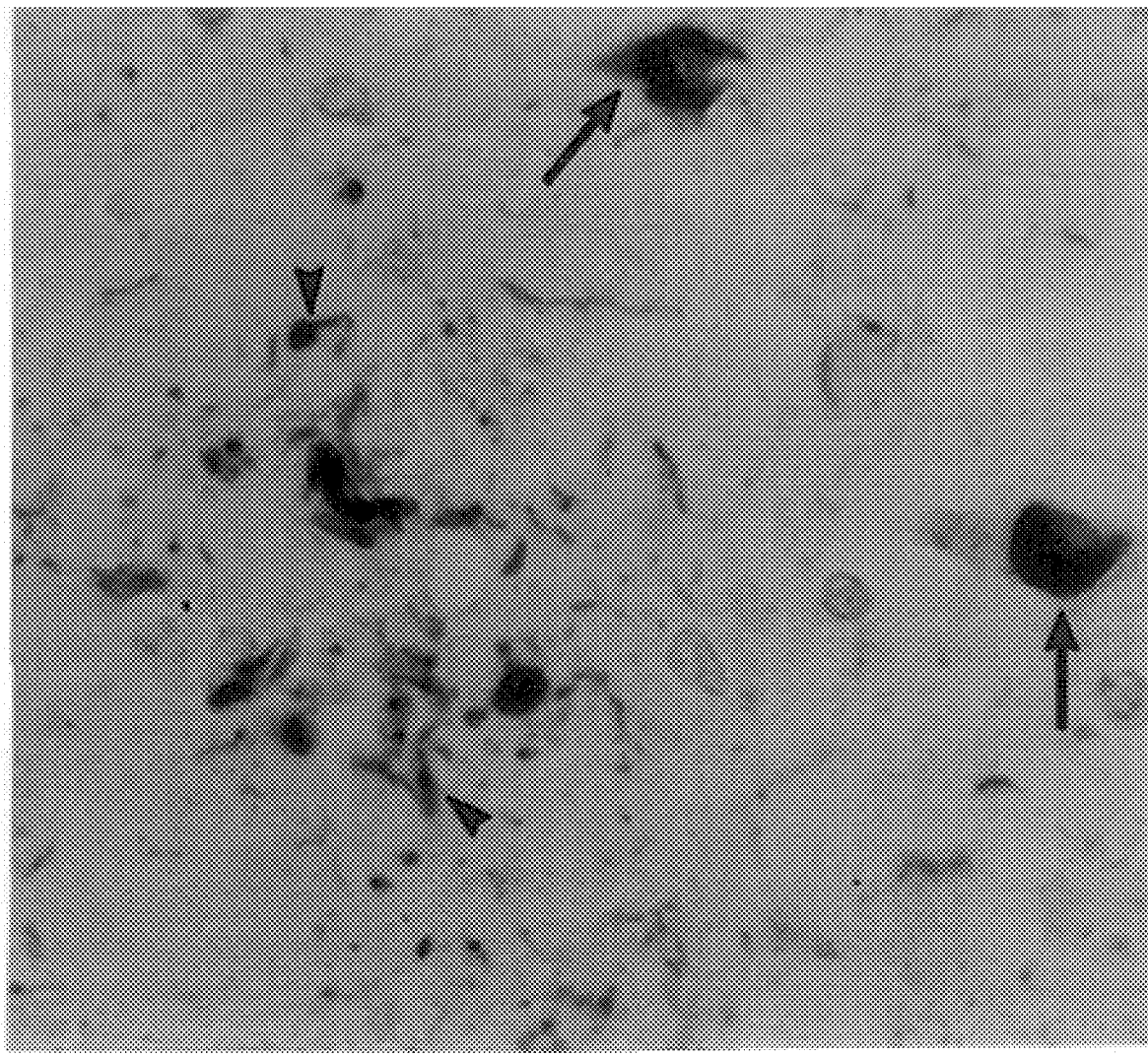
FIG. 1 is a copy of a paraffin section of the frontal cortex of a female Alzheimer patient (70 years old, #83170, Table 2) immunocytochemically incubated with an antibody against a peptide predicted by the +1 reading frame of βAPP (Tables 5 and 6). Dystrophic neurites (arrowheads) and tangles (arrows) are clearly visible in the cortical layer III.

The invention is illustrated by the following nonlimiting examples wherein the following materials and methods are employed. The entire disclosure of each of the literature references cited hereinafter are incorporated by reference herein.

The present invention is based on the discovery that frameshift mutations occur in a single gene or number of genes whose product or products are mutant proteins that are associated with, and indicative of, a disease state. The invention is based on the recognition that the presence of a frameshift mutation results in a new coding sequence for the cell containing the frameshift mutation, and thus a new polypeptide (herein termed a mutant protein) which may be correlated with and thus be indicative of a disease.

According to the present invention, diagnosis and/or identification of a disease caused by or associated with at least one gene having one or more somatic mutations which give rise to a frameshift mutation is accomplished as described herein.

According to the present invention, methods for preventing and/or treating the diseases, vectors for preventing and/or treating the diseases and for the production of diagnostic reagents, compositions for preventing and/or treating the diseases, nucleic acid sequences, probes and antibody molecules for use in the present invention and transgenic animals are accomplished as described herein.

Nucleotide deletions and other somatic mutations occur in genes due to a variety of reasons including errors in replication, as a result of recombination events, due to the presence of the mutagenic compounds, or as a result of a highly transcriptionally active state. Somatic mutations therefore regularly occur. In order to protect against such somatic mutations, mechanisms for correcting such mutations exist. The correction mechanisms involve a number of repair enzymes which detect and bind to the site of a mutation, and correct the mutation.

If the repair enzymes are defective or absent a number of problems can occur. For example, in xeroderma pigmentosum a deficiency in the excision-repair of somatic mutations leads to skin disorders in the patient. More recently, it has been shown that defective repair enzymes can lead to predisposition for certain sporadic cancers. For example, hereditary non-polyposis colorectal carcinoma (HNPCC). See TIG, 10 (5), pp 164 to 168, (1994), for a review.

According to the present invention, methods for detecting errors in nucleic acid repair mechanisms are accomplished as described herein. The correction of the mutations found in the mutant genes of the present invention is therefore a valuable method for combatting diseases.

Further methods for combatting diseases caused by at least one gene having one or more somatic mutations giving rise to a frameshift mutation, include targeting the mutant gene with an oligonucleotide having a correct nucleotide sequence and relying on endogenous or exogenous cellular repair enzymes to repair enzymes to repair the mutation, or targeting the mRNA transcript transcribed from the mutated gene, and correcting the mutant mRNA using ribozymes.

Methods and reagents for disease diagnosis and treatment are described in more detail hereinbelow.

Diagnosis of Diseases According to the Invention

The invention relates to methods for diagnosing diseases caused by or associated with at least one gene having one or more somatic mutations which give rise to a frameshift mutation. Such diseases include but are not limited to cancers and neurodegenerative diseases such as Parkinson's Disease (PD), Alzheimer's Disease (AD), frontal lobe dementia (Pick's Disease), progressive supranuclear palsy (PSP), amyotrophic lateral sclerosis, Huntington's Disease, multiple sclerosis, Down's syndrome, and other degenerative diseases such as cardiovascular diseases and rheumatoid arthritis.

Somatic mutations can result in a different gene function and have been implicated in diseases associated with ageing, such as certain cancers. However, it has generally been assumed that non-proliferating cells do not undergo important changes at the genomic level. For example, it was assumed previously that genomic changes are mainly related to cell proliferation (Smith, Mutation Research, 277, pp 139–142, 1992) which for non-proliferating cells such as most neurons ends during early postnatal life (Rakic, Science, 277, pp 1054–1056, 1985). However, Evans et al., 1994, Proc. Nat. Aca. Sci. 91:6059, observed that somatic mutations do occur in genes of the neuronal system, i.e., in post-mitotic neurons. The di/di Brattleboro rat, which suffers from severe diabetes insipidus due to the absence of the antidiuretic hormone vasopressin (VP), was the subject of the Evans et al. paper. It had previously been established that the VP hormone was absent in the Brattleboro rat due to a deletion of a single G residue in the second exon of the VP gene, resulting in a mutant VP precursor with an altered C-terminal amino acid sequence. It had also been observed that a small number of neurons in the di/di rat exhibited a heterozygous +/di phenotype and expressed an apparently normal VP gene product. In studying the molecular biology of the di/di rat, Evans et al. identified sequence alterations that restored the reading frame of the mutant VP precursor mRNA, which were based on a two-nucleotide deletion in a GAGAG motif. They correlated the presence of small amounts of normal VP gene product in single magnocellular neurons with a reversion of the mutant gene stemming from a frameshift mutation. Evans et al. concluded that, because +1 frameshift mutations are present in VP transcripts of both wild-type rats and di/di rats, the events leading to these mutations are not caused by the diseased state of the di/di rat per se. Thus, Evans et al. did not correlate a mutational GAGAG hotspot with a disease state, or predeliction to a disease.

In the present invention, the observations of Evans et al., as to reversions at GAGAG hotspots in VP transcripts within single neurons of the di/di rat leading to wild-type VP gene products, is extended and developed. According to the present invention, a human disease which is caused by or associated with at least one gene having one or more somatic mutations occurring at a mutational hotspot and which give rise to a frameshift mutation is identified and/or diagnosed. The nucleotide sequence of a gene suspected of being involved in the pathogenesis of a disease is provided, e.g., from published gene sequences or from cloning and sequencing of a suspect gene. The amino acid sequence encoded by the gene is then predicted, as are amino acid sequences of encoded mutant proteins. Mutant protein sequences are predicted in +1 and +2 reading frames following a hypothesized frameshift mutation. The location of the frameshift mutation may be hypothesized with respect to certain nucleotide sequence motifs which are suspected of causing frameshift mutations during transcription, examples of such motifs including but not limited to GAGA, for example, GAGAG, GAGAC, GAGAA, and GAGAT.

A probe is then prepared that is specific for the mutant protein or an immunogenic fragment thereof (such probes being described hereinabove for detection of proteins or protein fragments). Depending on where the mutation that leads to the frameshift occurs, part of the mutant protein will have the same sequence as the wild-type protein and part of the protein will have the sequence of the mutant protein. Furthermore, depending on where the mutation occurs the mutant protein will terminate when the nucleotide sequence codes for a stop codon (indicated as* in the Figures). Thus, different mutant proteins will be produced depending on where the mutation occurs.

Alzheimer's Disease is a representative disease diagnosable and treatable according to the invention. AD is a neurodegenerative disease characterised by idiopathic progressive dementia and is the fourth highest major cause of death in developed countries. It affects 5 to 11% of the population over the age of 65 and as much as 47% of the population over the age of 85. At present there are an estimated 4 million patients suffering from AD in the U.S.A. (see Coleman, Neurobiol. of Ageing, 15, Suppl. 2, pp 577–578, 1994), and an estimated 20 million Alzhemier's patients worldwide.

The clinical criteria for AD diagnosis have been defined (see Reisberg et al., Am. J. Psych. 12, pp 1136–1139, 1982; McKhann et al., Neurology, 34, pp 939–944, 1984). The early symptoms of AD vary but generally include depression, paranoia and anxiety. There is also a slow degeneration of intellectual function and memory. In particular, cognitive dysfunction and specific disturbances of speech (aphasia), motor activity (apraxia), and recognition of perception (agnosia) can occur.

There is not yet general consensus in a test for ante mortem diagnosis for AD due to the lack of knowledge of the pathogenic mechanisms involved in AD. Diagnosis of AD is made by examination of brain tissue. Such diagnosis is usually carried out on individuals post mortem. The diagnosis is based on the presence of a large number of intraneuronal neurofibrillary tangles and of neuritic plaques in the brain tissue, in particular in the neocortex and hippocampus. In order to identify the various types of plaques (e.g. neuritic plaques), neuropil threads and neurofibrillary tangles, staining and microscopic examination of several brain tissue sections is necessary. Neuritic plaques are believed to be composed of degenerating axons (e.g., neuropil threads), nerve terminals and possibly astrocytic and microglial elements. It is also often found that neuritic plaques have an amyloid protein core. The neurofibrillary tangles comprise normal and paired helical filaments and are believed to consist of several proteins.

There are two major types of AD, late onset (>60 years) and early onset (<60 years). Approximately 75% of all AD cases are late onset and only 25% are early onset. Of the latter group 2.4% consists of the familial type of AD linked to chromosome 21 and 28% of the cases are considered to be linked to chromosome 14, as discussed below. In addition, a recent linkage to chromosome 1 has been established for juvenile onset (0.4%). Sporadic cases are the most prominent group (60%).

In the most common late onset group, 10 to 30% of cases are considered to be related to chromosome 19, and in particular the apolipoprotein-$E_4$ gene is considered to be an important risk factor. The remaining late onset cases are non-familial or "sporadic" cases (see Van Broeckhoven et al., Europ. Neurol., 35, pp 8–19, 1995 and Table 1). For these cases relatively little is known and previously no data was available which suggested a possible cause of AD.

At present, it is unclear whether the formation of neuritic plaques and/or neurofibrillary tangles is directly responsible for causing AD. The formation of neuritic plaques, neuropil threads and/or neurofibrillary tangles may be a consequence of a more fundamental cellular or biochemical change.

Diagnostic methods of the invention will include the detection of nucleic acid sequences, preferably via procedures which involve formation of a nucleic acid duplex between two nucleic acid strands, i.e., a nucleic acid probe and a complementary sequence in DNA from a biological sample, or detection of a protein, preferably a mutant or hybrid wild-type/nonsense protein, as defined herein.

1. Preparation and Detection of DNA for Genetic Screening.

Typically, DNA is prepared from the biological sample by DNA extraction procedures well-known in the art (see, e.g., Sambrook et al., 1990, A Laboratory Manual for Cloning, Cold Spring Harbor Press, CSH, N.Y.), and may be further purified if desired, e.g., by electro-elution, prior to analysis.

Methods of detecting a mutated gene in DNA from a biological sample include, but are not limited to the following: (1) polymerase chain reaction (PCR) followed by sizing gel electrophoresis or hybridization with an allele-specific (or sequence-specific) probe; (2) hybridization of the eluted DNA with a nucleic acid probe that is complementary to the mutated gene; (3) allele-specific oligonucleotide (ASO) PCR followed by an amplification-detection system (e.g., gel electrophoresis and staining or HPLC); (4) the ARMS test, in which one primer has a complementary sequence encompassing the mutation which gives rise to the frameshift mutation, and amplification only occurs if the mutated sequence is present.; and (5) nucleotide sequencing.

A DNA probe useful according to the invention is preferably sufficiently complementary to the mutant sequence of the gene so that under stringent conditions the probe only remains bound to the mutant sequence (see Evans et al., Proc. Natl. Acad. Sci. USA, 91:6059–6063, (1994). The probe is preferably labelled using any of the standard techniques known to those skilled in the art, such as radioactively using $^{32}p$ or any other standard isotopes, or using non-radioactive methods including biotin or DIG labelling. The labelled probe can then be easily detected by methods well known to those skilled in the art.

An alternative method for detecting the presence of the mutant gene is via the polymerase chain reaction (PCR). Primers having a sequence complementary to the sequence either side of the mutation which gives rise to the frameshift mutation are used to amplify the DNA or RNA (if RNA is being detected a reverse transcriptase stage must be performed, as would be apparent to one skilled on the art) containing the mutation. The mutation in the amplified fragment can then be detected using the probe described above using standard techniques or by sequencing the amplified fragment. The advantages of using the PCR reaction is that the actual mutated sequence is obtained, less starting material is required and the PCR methods allow quantitative as well as qualitative determinations to be made. Quantitative determinations allow the number of copies of a mutated gene present in a particular sample to be estimated, and given this information the severity of the diseased state can be estimated.

Another alternative method for detecting the presence of the mutant gene is one in which one primer has a complementary sequence encompassing the mutation which gives rise to the frameshift mutation. Amplification will therefore only occur if the mutated sequence is present. Newton et al., Nucl. Acids. Res. 17:2503, 1989. The method has previously been used in detecting mutations in the gene responsible for cystic fibrosis, and one skilled in the art could easily perform this test for the detection of the mutant gene of the present invention.

An example of analysis method (1) follows. The DNA is amplified, e.g., using PCR, prior to analysis. Specific conditions for any one PCR, i.e. a PCR targeting a particular sequence, or for any one multiplex PCR, i.e. a PCR targeting a particular set of sequences, may vary but will be known to a person of ordinary skill in the art.

Amplification of a mutated or wild-type nucleic acid sequence can be accomplished directly from an aliquot of the prepared DNA as follows.

25 $\mu$l of DNA is aliquotted into a reaction tube containing 25 $\mu$l H$_2$O, 50 $\mu$l master mix (see below), 0.5 $\mu$l Amplitaq (Perkin Elmer Cetus, Norwalk, Conn.) and 0.5 µl UNG (Perkin Elmer Cetus, Norwalk, Conn.). A 50 µl master mix comprises 20 mM Tris HCl, pH 8.3, 100 mM KCl, 5 mM $MgCl_2$, 0.02 µmoles each of dATP, dGTP, dCTP, 0.04 µmoles of dUTP, 20 pmoles of each primer (Perkin Elmer Cetus, Norwalk, Conn.), and 25 µg gelatin.

A fragment characteristic of the selected amplification sequence can then be visualized under ultraviolet light after ethidium bromide staining a 13% polyacrylamide gel in which an aliquot of the amplification has been electrophoresed. Alternatively, hybridization with allele-specific probes can identify the presence of amplified product from either the normal and/or mutant alleles.

2. Preparation and Detection of Protein for Genetic Screening.

Where the biological molecule to be analyzed is a protein, it may be desirable to release the nucleic acid from biological sample cells prior to protein elution, or to remove nucleic acid from the sample eluate prior to protein analysis. Thus, the sample or eluate may first be treated to release or remove the nucleic acid by mechanical disruption (such as freeze/thaw, abrasion, sonication), physical/chemical disruption, such as treatment with detergents (e.g., Triton, Tween, or sodium dodecylsulfate), osmotic shock, heat, enzymatic lysis (lysozyme, proteinase K, pepsin, etc.), or nuclease treatment, all according to conventional methods well known in the art.

Where a biological sample includes a mutant protein, the presence or absence of which is indicative of a genetic disease, the protein may be detected using conventional detection assays, e.g., using protein-specific probes such as an antibody probe. Similarly, where a genetic disease correlates with the presence or absence of an amino acid or sequence of amino acids, these amino acids may be detected using conventional means, e.g., an antibody which is specific for the native or mutant sequence (see Table 7 for examples of amino acid sequences present in mutant proteins).

Any of the antibody reagents useful in the method of the present invention may comprise whole antibodies, antibody fragments, polyfunctional antibody aggregates, or in general any substance comprising one or more specific binding sites from an antibody. The antibody fragments may be fragments such as Fv, Fab and F(ab')$_2$ fragments or any derivatives thereof, such as a single chain Fv fragments. The antibodies or antibody fragments may be non-recombinant, recombinant or humanized. The antibody may be of any immunoglobulin isotype, e.g., IgG, IgM, and so forth. In addition, aggregates, polymers, derivatives and conjugates of immunoglobulins or their fragments can be used where appropriate.

The immunoglobulin source for an antibody reagent can be obtained in any manner such as by preparation of a conventional polyclonal antiserum or by preparation of a monoclonal or a chimeric antibody. Antiserum can be obtained by well-established techniques involving immunization of an animal, such as a mouse, rabbit, guinea pig or goat, with an appropriate immunogen.

Preparation of Antibodies

1. Polyclonal antibodies.

The peptide or polypeptide may be conjugated to a conventional carrier in order to increases its immunogenicity, and antisera to the peptide-carrier conjugate is raised in rabbits. Coupling of a peptide to a carrier protein and immunizations are performed as described (Dymecki, S. M., et al., J. Biol. Chem 267:4815–4823, 1992). Rabbit antibodies against this peptide are raised and the sera titered against peptide antigen by ELISA or alternatively by dot or spot blotting (Boersma and Van Leeuwen, 1994, Jour. Neurosci. Methods 51:317. At the same time, the antisera may be used in tissue sections. The sera is shown to react strongly with the appropriate peptides by ELISA, following the procedures of Green et al., Cell, 28, 477–487 (1982). The sera exhibiting the highest titer is used in subsequent experiments.

2. Monoclonal antibodies.

Techniques for preparing monoclonal antibodies are well known, and monoclonal antibodies of this invention may be prepared using a synthetic peptide, preferably bound to a carrier, as described by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic peptides or their conjugates.

Particularly preferred immunological tests rely on the use of either monoclonal or polyclonal antibodies and include enzyme linked immunoassays (ELISA), immunoblotting, immunoprecipitation and radioimmunoassays. See Voller, A., Diagnostic Horizons 2:1–7, 1978, Microbiological Associates Quarterly Publication, Walkersville, Md.; Voller, A. et al., J. Clin. Pathol. 31:507–520 (1978); U.S. Reissue Pat. No. 31,006; UK Patent 2,019,408; Butler, J. E., Meth. Enzymol. 73:482–523 (1981); Maggio, E. (ed.), Enzyme Immunoassay, CRC Press, Boca Raton, Fla., 1980) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing tissues for the presence of the mutant protein of the present invention, immunohistochemistry techniques are preferably used. It will be apparent to one skilled in the art that the antibody molecule will have to labelled to facilitate easy detection of mutant protein. Techniques for labelling antibody molecules are well known to those skilled in the art (see Harlour and Lane, Antibodies, Cold Spring Harbour Laboratory, pp 1–726, 1989).

Alternatively, sandwich hybridization techniques may be used, e.g., an antibody specific for a given protein. In addition, an antibody specific for a haptenic group conjugated to the binding protein can be used. Another sandwich detection system useful for detection is the avidin or streptavidin system, where a protein specific for the detectable protein has been modified by addition of biotin. In yet another embodiment, the antibody may be replaced with a non-immunoglobulin protein which has the property of binding to an immunoglobulin molecule, for example Staphylococcal protein A or Streptococcal protein G, which are well-known in the art. The protein may either itself be detectable labeled or may be detected indirectly by a detectable labeled secondary binding protein, for example, a second antibody specific for the first antibody. Thus, if a rabbit-anti-hybrid wild-type/nonsense protein antibody serves as the first binding protein, a labeled goat-anti-rabbit immunoglobulin antibody would be a second binding protein.

In another embodiment, the signal generated by the presence of the hybrid wild-type/nonsense protein is amplified by reaction with a specific antibody for that fusion protein (e.g., an anti-β-galactosidase antibody) which is detectably labeled. One of ordinary skill in the art can devise without undue experimentation a number of such possible first and second binding protein systems using conventional methods well-known in the art.

Alternatively, other techniques can be used to detect the mutant proteins, including chromatographic methods such as SDS PAGE, isoelectric focusing, Western blotting, HPLC and capillary electrophoresis.

Identification of Diseases According to the Invention

The invention provides methods for identifying diseases caused by or associated with at least one gene having one or more somatic mutations which give rise to a frameshift mutation.

Diseases are identified according to the invention as follows. The nucleotide sequence of a gene suspected of being involved in the pathogenesis of a disease is provided, e.g., from published gene sequences or from cloning and sequencing of a suspect gene. The amino acid sequence encoded by the gene is then predicted, as are amino acid sequences of encoded mutant proteins. Mutant protein sequences are predicted in +1 and +2 reading frames following a hypothesized frameshift mutation. The location of the frameshift mutation may be hypothesized with respect to certain nucleotide sequence motifs, examples of such motifs including but not limited to GAGA, for example, GAGAG, GAGAC, GAGAA, and GAGAT.

A probe is then prepared that is specific for the mutant protein or an immunogenic fragment thereof (such probes being described hereinabove for detection of proteins or protein fragments). Depending on where the mutation that leads to the frameshift occurs, part of the mutant protein will have the same sequence as the wild-type protein and part of the protein will have the sequence of the mutant protein. Furthermore, depending on where the mutation occurs the mutant protein will terminate when the nucleotide sequence codes for a stop codon (indicated as* in the Figures). Thus, different mutant proteins will be produced depending on where the mutation occurs.

The simplest method of probing for the presence of a particular mutant protein is to make an antibody to that protein or an immunogenic portion thereof. An immunogenic fragment may be synthesized corresponding to the C-terminus of the predicted mutant proteins because even if the mutation occurred at another position in the sequence the probability that the derived mutant protein contains the peptide sequence is increased. Furthermore, the C-terminal region of a protein is more likely to form an epitope than other regions of the protein.

Once a probe is made, a biological sample from a patient having the disease and a biological sample from a patient not having the disease is probed for the presence or absence of the mutant protein, also as described above. Alternatively, several probes may be prepared and the combination of probes used to probe the tissue sample. The presence of the mutant protein in a biological sample from a patient having the disease and the absence of said mutant protein in a biological sample from a patient not having the disease indicates that the mutant protein is a marker for the disease or susceptibility to the disease.

Treatment of Diseases According to the Invention

The invention also relates to methods for preventing and/or treating diseases, vectors for preventing and/or treating the diseases, and compositions such as nucleic acid sequences and proteins for preventing and/or treating the diseases, which methods and compositions are useful in gene and protein therapies.

The invention includes methods of treatment and/or prevention of a disease caused by or associated with a gene having a somatic mutation giving rise to a frameshift mutation in which a vector comprising an expressible gene encoding a repair enzyme or a ribozyme is administered to a patient suffering from or susceptible to the disease. Preferred diseases which are treated according to the invention include but are not limited to cancer or a neurodegenerative disease, especially AD, the preferred mutant genes of the present invention are those encoding the $\beta$ amyloid precursor protein, the Tau protein, ubiquitin, apolipoprotein-$E_4$ (Apo-$E_4$), microtubule associated protein II (MAP 2) and the neurofilament proteins, having a deletion, insertion or other modification leading to a frameshift mutation.

Examples of genes encoding such repair enzymes include but are not limited to genes encoding MSH 1–6, PMS 1–2, MLH 1 or GTBP.

The invention includes methods of treatment and/or prevention of a disease in which a vector comprising an expressible gene encoding the wild-type version of the mutated gene is administered to a patient suffering from or susceptible to the disease. Examples of genes encoding a wild-type version of a mutated gene include but are not limited to those disclosed herein and sequences disclosed in the figures.

A vector comprising an expressible gene encoding a repair enzyme (that is, the wild-type version of a defective repair enzyme which has lead to or contributed to the presence of the mutated gene which causes or is associated with a disease), a ribozyme, or a wild-type version of a mutated gene are characterized as described below.

The vectors of the present invention are preferably nucleic acid vectors comprising RNA or DNA. The vectors may be of linear or circular configuration and may be adapted for episomal or integrated existence in the host cell, as set out in the extensive body of literature known to those skilled in the art. The vectors may be delivered to cells using viral or non-viral delivery systems. The choice of delivery system will depend on whether the nucleic acid sequence to be delivered is to be incorporated into the cell genome or is to remain episomal.

Vectors of the present invention additionally may comprise further control sequences such as enhancers or locus control regions (LCRs), in order to lead to more controlled expression of the encoded gene or genes. LCRs are described in EP-A-0332667. The inclusion of a locus control region (LCR), is particularly preferred as it ensures the DNA is inserted in an open state at the site of integration, thereby allowing expression of the gene or genes contained in the vector. The vectors of the present invention have wide range of applications in ex vivo and in vivo gene therapy.

The invention also includes treatment of a disease by administration of a pharmaceutical composition comprising the wild-type analog of a mutant protein in admixture with a pharmaceutically acceptable carrier.

A pharmaceutical composition according to the invention will include a therapeutically effective amount of the wild-type analog of the mutant protein, a repair enzyme, or a ribozyme, in admixture with a carrier. A therapeutically effective amount is considered that amount which, when administered to a patient, provides a therapeutic benefit to the patient. Such amounts will generally be in the range of 10 ug–100 mg of therapeutic protein/kg body weight of the patient, preferably 50ug–10 mg, and most preferably 100 ug–1 mg.

Animal Models for Disease Diagnosis and Treatment According to the Invention The invention also includes cell lines and transgenic animals for use as disease models for testing or treatment. A cell line or transgenic animal according to the invention will contain a recombinant gene, also known herein as a transgene, having one or more somatic mutations giving rise to a frameshift mutation which causes or is associated with a disease.

The recombinant gene will encode a mutated protein found to be indicative of a disease. Preferably, the mutant protein will contain an antigenic epitope specific for the diseased state. The recombinant gene may encode a protein comprising at least part of the sequence designated +1 or +2 in any one of FIGS. 2 to 9, or an immunologically equivalent fragment thereof.

A cell line containing a transgene encoding a mutant protein, as described herein, is made by introducing the transgene into a selected cell line according to any one of several procedures known in the art for introducing a foreign gene into a cell.

A transgenic animal containing such a transgene includes a rodent, such as a rat or mouse, or other mammals, such as a goat, a cow, etc. and may be made according to procedures well-known in the art.

Transgenic animals are useful according to the invention as disease models for the purposes of research into diseases caused by or associated with at least one gene having one or more somatic mutations giving rise to a frameshift mutation, and therapies therefore. By specifically expressing one or more mutant genes, as defined above, the effect of such mutations on the development of the disease can be studied. Furthermore, therapies including gene therapy and various drugs can be tested on the transgenic animals.

Transgenic animals of the present invention may be additionally defective in nucleic acid repair mechanisms. Thus, the mutated gene specifically expressed in the transgenic animal will not be repaired.

EXAMPLE 1

Described below is an embodiment of the invention involving identification of somatic frameshift mutations in genes encoding proteins which are present in neuronal tissue, and how such mutations are useful in diagnosis of certain disease states.

The DNA sequences coding for the human amyloid A4 protein, Tau, ubiquitin, apolipoprotein E4, MAP 2 and the neurofilament subunits low, medium and high, were obtained from various gene sequence databases.

Using the sequence data, the various GAGA motifs in the sequences were identified, and deletions were hypothesized and the sequences of the derived mutant proteins predicted, as shown in FIGS. 2 to 9. Both the sequences of the +1 and +2 frameshift mutant proteins were predicted.

By examining the sequences of the hypothesized mutant proteins, a peptide corresponding to the C-terminus of the hypothesized mutant proteins was synthesized. The peptides were synthesized using standard techniques known to those skilled in the art. The peptides having the following sequences were synthesized: RGRTSSKELA SEQ ID NO:1; HGRLAPARHAS SEQ ID NO:2; YADLREDPDRQ SEQ ID NO:3; RQDHHPGSGAQ SEQ ID NO:4; GAPRLPPAQAA SEQ ID NO:5; KTRFQRKGPS SEQ ID NO:6; PGNRSMGHE SEQ ID NO:7; EAEGGSRS SEQ ID NO:8; and VGAARDSRAA SEQ ID NO:9.

Depending on where the mutation that leads to the frameshift occurs, part of the mutant protein will have the same sequence as the wild-type protein and part of the protein will have the sequence of the mutant protein. Furthermore, depending on where the mutation occurs the mutant protein will terminate when the nucleotide sequence codes for a stop codon (indicated as* in the Figures). Thus different mutant proteins will be produced depending on where the mutation occurs.

It is predicted that mutations will occur at GAGA motifs and the sequences of the mutant proteins predicted accordingly.

Peptides were synthesized corresponding to the C-terminus of the predicted mutant proteins because even if the mutation occurred at another position in the sequence the probability that the derived mutant protein contains the peptide sequence is increased. Furthermore, the C-terminus region of a protein is more likely to form an epitope than other regions of the protein.

The uniqueness of the synthesized peptides was confirmed by a gene sequence database search.

Each synthesized peptide was then injected into a rabbit and an antibody having affinity for the peptide purified. The techniques used to obtain the antibodies are standard techniques known to those skilled in the art.

The antibodies obtained were then tested on autopsy material of frontal cortex, temporal lobe and hippocampus of neuropathologically confirmed AD cases and control non-AD cases. The presence of the antibodies is determined using standard detection methods known to those skilled in the art.

Figure 1B:
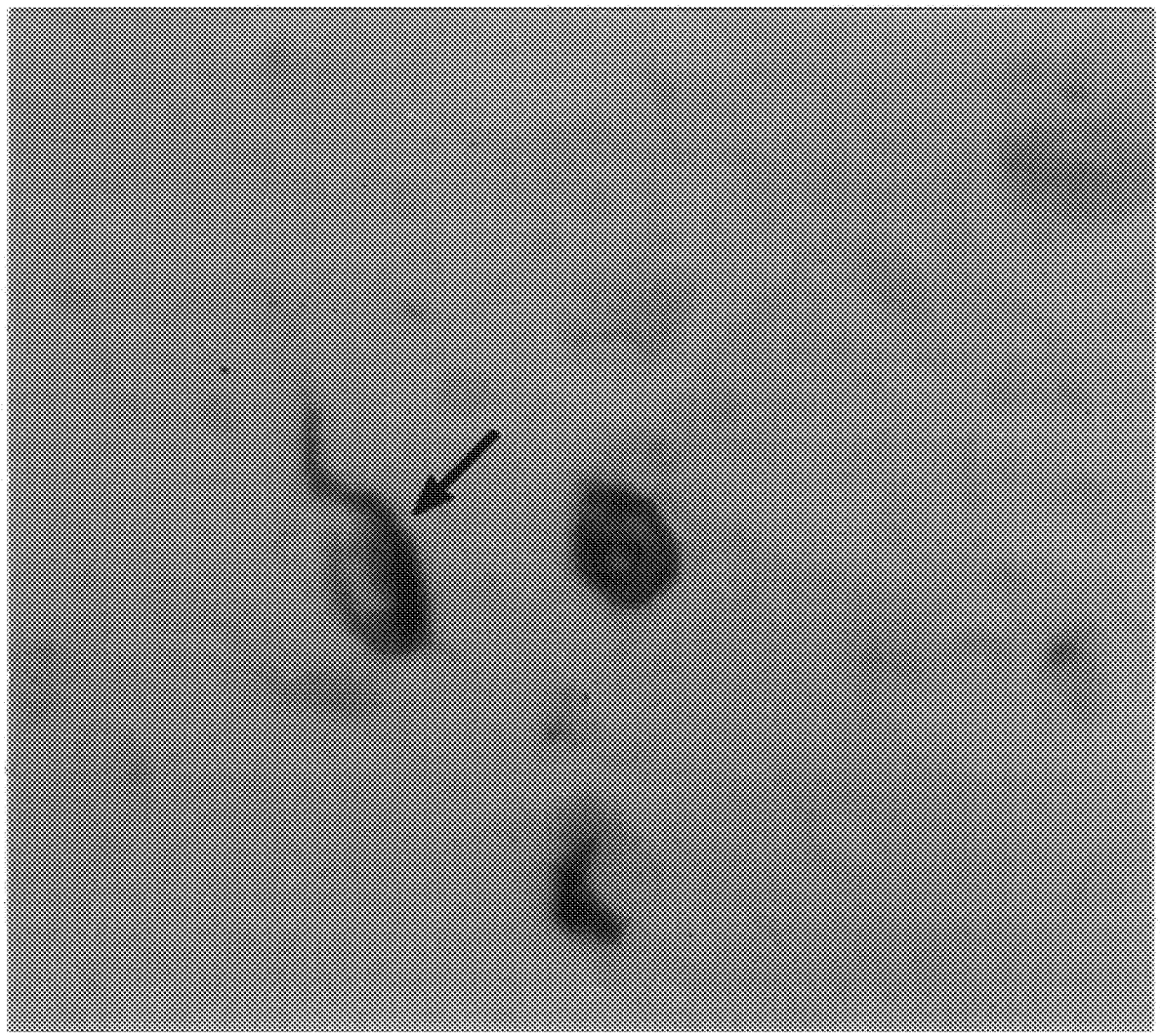

FIG. 1 shows the presence of the β amyloid precursor mutant protein in the frontal cortex of an Alzheimer patient identified using an antibody against a peptide predicted by the +1 reading frame of β amyloid precursor protein. The antibody used had affinity for a peptide having the following sequence RGRTSSKELA SEQ ID NO:1.

The results of other immunoreactive tests performed using the antibodies against the predicted peptides are shown in Table 2 and 3. Tables 2 and 3 also indicates the neuropathological state (presence of plaques/tangles) of the various tissue samples.

It can be seen that the presence of the mutant protein can be detected and correlates with the subject having AD. The presence of one or more of the mutant proteins can therefore be seen to be indicative of AD.

Table 4 summaries the immunoreactivity results within the frontal cortex (area 11), temporal cortex (area 38) and the hippocampus.

Other diseases also may be correlated with the presence of mutant proteins, as defined herein. For example, six patients with Down's syndrome were tested according to the invention. Down's syndrome is trisomy of chromosome 21 which leads to over-expression of β-amyloid precursor protein. We noted that the frontal and temporal cerebral cortex and hippocampus of these patients contained plaques and neurofibrillary tangles, and hypothesized that such over-expression may promote accumulation of somatic mutations in neurons, by frameshift mutations at a GAGAG motif in the over-expressed β-amyloid gene. After immunocytochemical staining of tissue from frontal and temporal cerebral cortex from the Down's patients with the above-described antibody specific for the amyloid +1 carboxy terminal peptide, immunoreactivity was observed in the neurofibrillary tangles in 4 of 6 patients. Staining was absent in the frontal cortex of the matched controls. Therefore, the mutant amyloid protein is correlated not only with Alzheimer's disease, but also with other diseases, such as Down's, involving Alzheimer's neuropathology.

It has been found that a number of the mutations occur at GAGA motifs. Table 5 shows the presence of GAGA motifs in various genes of the neuronal system. The motif or, as can be seen from the sequences of Tau and apolipoprotein E4, similar motifs such as GAGAG GAGAC, GAGAA, and GAGAT may be associated with the frameshift mutations that lead to or are associated with the disease. The presence of the motif or similar motifs in other genes may indicate that they are relevant to a disease. It is also possible that other mutations occur that are not associated with such motifs but still lead to frameshift mutations that cause or are associated with a disease.

Table 6 shows the presence of GAGAG motifs in particular genes of the neuronal system, namely βAPP, Tau and Ubiquitin. This table also indicates, inter alia, the chromosomal location of the genes and the molecular weight of the longest polypeptide forms encoded by the genes and the predicted size of the aberrant +1 peptide with its C-terminus against which the antibodies were raised. These peptides were revealed in a Western blot and also identified with a different antibody recognizing an epitope on the unaffected wild-type N-terminus.

EXAMPLE 2

Selection of Antigenic Peptide

Synthetic polypeptides corresponding in sequence to a portion of a mutant protein (whether such peptides are chemically synthesized or are chemically or recombinantly-generated fragments of a protein), as described herein, will be useful according to the invention as antigenic peptides for generation of antibodies specific for a mutant protein, provided they possess the following characteristics. The synthetic peptide will include a minimum of 12 and preferably 15 amino acid residues, and an optimum length of 20–21 amino acids. The hydrophilicity and antigenic index of the amino acid sequence of the hybrid wild-type/nonsense protein may be determined by Analytical Biotechnology Sciences, Boston, Mass., using computer programming. Potential synthetic peptides useful according to the invention include a stretch of 12–20 amino acids preferably within the carboxy terminal 100–150 amino acids of the hybrid wild-type/nonsense protein.

The amino acid sequence of a selected peptide is searched in a computer database of sequences (e.g., GenBank) to preclude the possibility that at reasonable concentrations, antisera to any one peptide would specifically interact with any protein of a known sequence. Preferred sequences are those which are determined not to have a close homolog (i.e., "close" meaning 80–100% identity).

EXAMPLE 3

Detection of "Mutant" Protein

Another embodiment of this invention relates to an assay for the presence of the "mutant" or mutant protein in a given tissue as indicative of a disease state. Here, an above-described antibody is prepared. The antibody or idiotype-containing polyamide portion thereof is then admixed with candidate tissue and an indicating group. The presence of the naturally occurring amino acid sequence is ascertained by the formation of an immune reaction, as signaled by the indicating group. Candidate tissues include any tissue or cell line or bodily fluid to be tested for the presence of the mutant protein, as described hereinabove.

Expression of a given hybrid wild-type/nonsense protein may be investigated using antiserum prepared in rabbits against a peptide corresponding to a carboxy terminal stretch of amino acids in the hybrid wild-type/nonsense protein as follows.

CMK cells or U3T3 cells are metabolically labeled with $^{35}$S-methionine and extracts are immunoprecipitated with antiserum. If the hybrid wild-type/nonsense protein is present in the cells, then a protein species of corresponding molecular weight will be detected in CMK and U3T3 cells. The protein may be localized to the membrane, nucleus or cytoplasm by Western blot analysis of the nuclear, membrane and cytoplasmic fractions, as generally described in Towbin et al., Proc. Natl. Acad. Sci. USA, 76, 4350–4354 (1979). This localization may be confirmed by immunofluorescence analysis to be associated mainly with the plasma membrane.

Metabolic labeling immunoprecipitation, and immunolocalization assays are performed as described previously (Furth, M. E., et al., Oncogene 1:47–58, 1987; Laemmli, U. K., Nature 227:680–685, 1970; Yarden, Y., et al., EMBO J. 6:3341–3351, 1987; Konopka, J. B., et al., Mol. Cell. Biol. 5:3116–3123, 1985). For immunoblot analysis, total lysates are prepared (using Fruth's lysis buffer) (Fruth, M. E., et al., Oncogene, 1:47–58, 1987). Relative protein concentrations are determined with a colorimetric assay kit (Bio-Rad) with bovine serum albumin as the standard. A protein of lysate containing approximately 0.05 mg of protein was mixed with an equal volume of 2×SDS sample buffer containing 2 mercaptoethanol, boiled for 5 min., fractioned on 10% polyacrylamide-SDS gels (Konopka, J. B., et al., J.Virol., 51:223–232, 1984) and transferred to immunobilon polyvinyldine difluoride (Millipore Corp., Bedford, Mass.) filters. Protein blots were treated with specific antipeptide antibodies (see below). Primary binding of the specific antibodies may be detected using anti-IgG second antibodies conjugated to horseradish peroxidase and subsequent chemiluminescence development ECL Western blotting system (Amersham International).

For metabolic labeling, $10^6$ cells are labeled with 100 $\mu$Ci of $^{35}$S-methionine in 1 ml of Dulbecco's modified Eagles medium minus methionine (Amersham Corp.) for 16 h. Immunoprecipitation of protein from labeled cells with antipeptide antiserum is performed as described (Dymecki, S. M., et al., J. Biol. Chem 267:4815–4823, 1992). Portions of lysates containing $10^7$ cpm of acid-insolube S-methionine were incubated with 1 $\mu$g of the antiserum in 0.5 ml of reaction mixture. Immunoprecipitation samples were analyzed by SDS-polylarcylamide gel electrophoresis and autoradiography.

For immunolocalization studies, $10^7$ CMK cells are resuspended in 1 ml of sonication buffer (60 mM Tris-HCl, pH 7.5, 6 mM EDTA, 15 mM EGTA, 0.75M sucrose, 0.03% leupeptin 12 mM phenylmethylsulfonyl fluoride, 30 mM 2-mercaptoethanol). Cells are sonicated 6 times for 10 seconds each and centrifuged at 25,000×g for 10 min at 4° C. The pellet is dissolved in 1 ml of sonication buffer and centrifuged at 25,000×g for 10 min at 4° C.

The pellet (nucleus fraction) is resuspended in 1 ml of sonication buffer and added to an equal volume of 2×SDS sample buffer. The supernatant obtained above (after the first sonication) is again centrifuged at 100,000×g for 40 min at 4° C. The supernatant (cytosolic fraction) is removed and added to an equal volume of 2× concentrated SDS sample buffer. The remaining pellet (membrane fraction) is washed and dissolved in sonication buffer and SDS sample buffer as described above. Protein samples are analyzed by electrophoresis on 10% polyacrylamide gels, according to the Laemmli method (Konopka, J. B., et al., Mol. Cell. Biol. 5:3116–3123, 1985). The proteins are transferred from the gels on a 0.45-µm polyvinylidine difluoride membrane for subsequent immunoblot analysis. Primary binding of antibodies is detected using anti-IgG second antibodies conjugated to horseradish peroxidase.

For immunohistochemical localization of a given protein, if desired, CMK cells or U3T3 are grown on cover slips to approximately 50% confluence and are washed with PBS (pH 7.4) after removing the medium. The cells are prefixed for 1 min at 37° C. in 1% paraformaldehyde containing 0.075% Triton X-100, rinsed with PBS and then fixed for 10 min with 4% paraformaldehyde. After the fixation step, cells are rinsed in PBS, quenched in PBS with 0.1 and finally rinsed again in PBS. For antibody staining, the cells are first blocked with a blocking solution (3% bovine serum albumin in PBS) and incubated for 1 h at 37° C. The cells are then incubated for 1 h at 37° C. with antiserum (1:100 dilution or with preimmune rabbit serum (1:100) (see below). After the incubation with the primary antibody, the cells are washed in PBS containing 3% bovine and serum albumin and 0.1% Tween 20 and incubated for 1 h at 37° C. in fluorescein-conjugated donkey anti-rabbit IgGs (Jackson Immunoresearch, Maine) diluted 1:100 in blocking solution.

The coverslips are washed in PBS (pH 8.0), and glycerol is added to each coverslip before mounting on glass slides and sealing with clear nail polish. All glass slides were examined with a Zeiss Axiophot microscope.

EXAMPLE 4

Biological Sample Analysis

The above methods for detection of a given mutant protein or nucleic acid are applicable to analyses involving tissues, cell lines and bodily fluids suspected of containing the marker protein.

For example, a sample of CNS tissue suspected of being in a diseased state may be analyzed, it having been previously observed according to the invention that tissue of that particular diseased state contains detectable levels of hybrid wild-type/nonsense proteins relative to healthy tissue.

An aliquot of the suspect sample and a healthy control sample are provided and admixed with an effective amount of an antibody specific for the hybrid wild-type/nonsense protein, as herein described, and an indicating group. The admixture is typically incubated, as is known, for a time sufficient to permit an immune reaction to occur. The incubated admixture is then assayed for the presence of an immune reaction as indicated by the indicating group. The relative levels of the hybrid wild-type/nonsense protein in the suspect sample and the control sample are then compared, allowing for diagnosis of a diseased or healthy state in the suspect sample.

The above types of analyzing for the presence of the hybrid wild-type/nonsense protein may, of course, be performed using analysis for the coding mRNA, e.g., via Northern blot or RNA dot blot analysis, both of which are conventional and known in the art.

Disease Treatment According to the Invention

Once a gene containing a frameshift mutation (i.e., a frameshifted gene), or a mutant protein is correlated with a disease state, the disease is treatable according to the invention as follows: by administering to a patient in need thereof a wild-type version of a mutant gene or the corresponding wild-type transcript; by administering the wild-type version of the hybrid wild-type/nonsense protein; by administering enzymes, or sequences encoding such enzymes, having activity that operates to correct nucleotide insertions or deletions (DNA repair enzymes); by administering enzymes which serve to correct frameshifted RNA via splicing, e.g., ribozymes; or by administering oligonucleotides or sequences encoding oligonucleotides to a cell as templates for repair of an insertion or deletion mutation. A patient in need thereof will include a patient exhibiting symptoms of the disease, even those patients suspected of developing the disease, i.e., who are monitored according to the invention by measuring the a tissue sample, e.g., the cerebrospinal fluid, for the presence of frameshifted peptides (e.g. peptides having an amino acid sequence in the +1 or +2 reading frame).

Therefore, it is contemplated according to the invention that the wild type version of the mutant (i.e., frameshifted) gene, or its encoded wild type protein, may be administered to the patient in order to treat the disease associated with the presence of the mutant gene or its encoded protein.

According to the invention, a vector encoding a non-mutated version of a frameshifted gene under the control of a promoter can be delivered to affected or susceptible cells leading to the production of the correct protein in the cell. Without being bound by any one theory, it is suggested that increasing the percentage of The correct protein produced in relation to the hybrid wild-type/nonsense protein will reduce or prevent further progression of the disease, and possibly reverse the diseased state. For example, in neurons having undergone a frameshift mutation in one of two expressed alleles, the balance between the wild-type and mutant transcripts may be shifted in favor of the wild-type one as a result of the treatments described herein. In addition, it is possible that not every mutant gene and transcript results in a mutant protein that is directly toxic to the neuronal tissue. For example, the mutant protein may be routed to the lysosomal system or just secreted (e.g. by the constitutive or regulated pathway)and degraded elsewhere. However, sometimes the mutant protein will be accumulated in the membranes of organelles, for instance in the endoplasmic reticulum, thus disrupting the normal processes of the cellular machinery. This may be especially true if both alleles of a given gene or if different genes are mutated.

The wild-type version of the mutated gene encodes the correct protein. The wild-type gene corresponds to the mutated gene found present in the affected cells and preferably the wild-type gene is expressed at high levels leading to the production of more wild-type protein than the mutated protein. When the disease is a neurodegenerative disease, preferred wild-type genes include the β amyloid protein gene, the Tau gene, the ubiquitin gene, the apolipoprotein-$E_4$ gene, the microtubule associated protein II (MAP2) gene and the neurofilament protein genes. The sequences of these genes are provided herein in the figures. Other preferred wild-type genes include the alpha and beta tubulin genes, the sequences of which are found in Cowan et al., Mol. and Cellular Biology, 3, 1738–1745(1983) and Lewis et al., J. Mol. Biol. 182, 11–20(1985), repectively.

When the disease is a non-hereditary cancer, preferred wild-type gene sequences include but are not limited to the human p53 gene and the bcl-2 gene. Mammalian phosphoprotein p53 has been shown to play an essential role in regulation of cell division and is required for the transition from phase G0 to G1 of the cell cycle. P53 is normally present in very low levels in normal cells and is believed to be a tumor suppressor gene; when present at high levels, p53 has been shown to play a role in transformation and malignancy. P53 gene alleles from normal and malignant tissues have been shown to contain BglII site polymorphism (Buchman et al., 1988, Gene 70:245). The p53 coding region contains several GAGA motifs, e.g., GAGAC at position 1476 of the sequence published in Buchman et al., GAGA at position 1498; GAGA at position 1643; and GAGA at position 1713, which motifs present candidate sites for frameshift mutations according to the invention. A frameshift mutation within the p53 gene thus may lead to loss of the natural p53 tumor suppressor function. Detection of such a mutation in p53 may be diagnostic of pre-malignancy or malignancy, and treatment as described herein which results in correction of p53 function may restore tumor suppressor function.

It is also contemplated according to the invention that a mutant gene, which mutation comprises a somatic mutation giving rise to a frameshift mutation that includes a nucleotide deletion or insertion (i.e., of one or more nucleotides), may be due to a deficit in one or more DNA repair enzymes and/or associated proteins in the cell containing the mutant gene. Therefore, where the disease is associated with a deficiency in a DNA repair enzyme, the disease may be treated by administering a DNA repair enzyme, or sequences encoding the repair enzyme, to the patient.

The present invention thus further provides a method of treatment and/or prevention of a disease caused by or associated with at least one gene having one or more somatic mutations giving rise to a frameshift mutation, comprising administering a vector encoding one or more repair enzymes under the control of a promoter to a patient suffering from or likely to suffer from the disease, or delivering the repair enzyme itself to a target cell containing the frameshifted gene.

The repair enzyme can be any repair enzyme which is capable of or contributes to, the repair of a somatic mutation which leads to a frameshift mutation, such as a dinucleotide deletion. Preferred repair enzymes include Mut H, Mut S, Mut L, and Mut U and the mammalian homologues thereof. These include MSH 1–6, PMS 1–2 and MLH 1, as described in Prolla et al., Science 265:1091, 1994; Strand et al., 1993, Nature 365:274; Kramer et al., 1984, Cell 38:879; Johnson et al., 1995, Science 269:238; Horii et al., 1994, Biochem. Biophys. Res. Comm. 204:1257; Jeyaprakash et al., 1994, Mutation Research 325:21; J. H. J. Hoeijmakers, 1987, Journal of Cell Science Suppl. 6:111–125; and Kunkel et al., supra.

The invention also encompasses methods of combatting diseases caused by at least one gene having one or more somatic mutations giving rise to a frameshift mutation by targeting the mRNA transcript transcribed from the mutated gene. Thus, it is also contemplated according to the invention that a frameshift mutation within a gene may be corrected at the level of the frameshifted RNA via splicing using a ribozyme having specificity for the correct mRNA sequence (see Denman et al., Arch. Of Biochem. Biophysics. 323,71–78,1995), and correcting the mutant mRNA using ribozymes. The disease associated with the frameshifted gene is thus treated by administering an appropriate ribozyme, or sequences encoding the ribozyme, to the patient.

Ribozymes of selected specificities may be made as described by Sullenger & Cech,Nature 371: 619–622, 1994), herein incorporated by reference. The ribozyme encoded by the vector is preferably specific for RNA containing the mutations described above or for the RNA encoding a defective repair enzyme. For example, if a defect in a repair enzyme has led to the mutated gene, by correcting the transcribed message from the repair enzyme gene the function of the repair enzyme can be restored.

Ribozymes and sequences encoding ribozymes may be prepared as described by Tuschl et al., Curr. Opin. Struc. Biol. 5:296, 1995 and Wahl et al., Curr. Opin. Struc. Biol. 5:282, 1995.

The invention also encompasses methods of treating diseases caused by or associated with at least one gene having one or more somatic mutations giving rise to a frameshift mutation by delivery of oligonucleotides or sequences encoding oligonucleotides to a target cell containing a frameshifted gene. The oligonucleotides will have a wild-type sequence with respect to the corresponding mutant sequence of the frameshifted gene, and thus may serve as templates for correction of the mutant sequence. For example, triple helix-forming oligonucleotides may be used to target mutations to selected genes within mammalian cells. Targeted mutagenesis in vivo depends upon the strength and specificity of the third strand binding. Oligonucleotides with strong target site binding affinity, i.e., with full target site homology (except for the base to be corrected, which base will be mismatched between the oligonucleotide and the nuclear DNA) are preferred. Also preferred are oligonucleotides between 10–30 nucleotides in length and containing a GAGA, GAGAC, GAGAG, GAGAA or GAGAT motif. Formation of a site-specific triple strand brings the wild type oligonucleotide sequence into proximity with the base pair to be mutated. DNA repair enzyme will then recognize the mismatch and will repair the mismatch. Targeted mutagenesis via triple helix formation has been shown to work in mammalian cells (see Wang et al., 1995, Mol. Cell Biol. 15:1759).

Disease treatment according to the invention is described below and includes preparation of the administered substance and administration of the substance to a patient suffering from a disease according to the invention. As used herein "substance" refers to any one of the following: a DNA repair enzyme, a ribozyme, a nucleic acid sequence encoding a repair enzyme or a ribozyme, a nucleic acid sequence comprising a wild type version of a mutant gene, and a wild type protein encoded by the wild type gene, an antibody specific for the frameshifted (nonsense) protein, and oligonucleotides having a wild type sequence to serve as a template for repair of a frameshift mutation.

Disease treatment according to the invention may be accomplished as follows. In Example 5, administration of nucleic acid sequences according to the invention is described. In Example 6, the purification of DNA repair enzymes is described. In Example 7, administration of proteins, ribozymes, or nucleic acids using liposomes is described. And in Example 8, delivery of these substances across the blood-brain barrier is described.

EXAMPLE 5

Administration of Nucleic Acids

Delivery of nucleic acid sequences encoding substances which effect or facilitate repair of the frameshifted gene is carried out as follows. Sequences encoding repair enzymes, ribozymes, a wild-type version of a mutant gene, or a wild-type oligonucleotide sequence may be cloned into an appropriate vector for expression in desired mammalian cell. The vector will include a promoter that is expressed in the target cell type, and also may include an nhancer and locus control region, as selected for expression in a given cell type.

Examples of vectors useful according to the invention include but are not limited to any vector which results in successful transfer of the coding sequences to the target mammalian cell, including both viral or non-viral vectors, e.g., retroviral vectors or adenoviral vectors.

For example, the retroviral gene transfer vector SAX (Kantoff et al., Proc. Nat. Aca. Sci. 83:6563, 1986) may be used to insert a selected coding sequence into a target cell. SAX is a moloney virus based vector with the neoR gene promoted from the retroviral LTR and the human ADA gene promoted from an internal SV40 promoter. Thus, the SAX vector may be engineered by one of skill in the art to contain the coding sequence for a DNA repair enzyme, a ribozyme, or a wild-type version of a mutant gene, or a selected oligonucleotide template sequence, identified as described herein, e.g., by substituting the desired coding region for the hADA coding region in the SAX vector.

It has been previously shown that ribozymes can be targeted to and can correct specific errors via a transplicing mechanism. See Sullenger & Cech, Nature, 371, pp 619–622, 1994. By correcting the mutant mRNA, the correct protein will be translated thus preventing and/or treating the disease. One skilled in the art following the teaching of Sullenger & Cech would easily be able to design a ribozyme to correct the mRNA transcript transcribed from the mutant gene of the present invention.

Expression vectors are known in the art which encode, or may be engineered to encode, a selected ribozyme. Yuyama et al., Nucl. Acids Res. 22:5060, 1994, describe a multifunctional expression vector encoding several ribozymes. This vector may be adapted to encoded a ribozyme of a selected specificity by substituting one or both ribozyme sequences in the vector for a selected ribozyme sequence. Zhou et al., Gene 149:33, 1994, and Yamada et al., Virology 205;121, 1994, describe retroviral transduction of ribozyme sequences into T cells. These retroviral vectors may be adapted to encode a selected ribozyme sequence. Liu et al., Gene Therapy 1:32, 1994, and Lee et al., Gene Therapy 2:377, 1995, describe expression vectors which are adaptable for use in expression of any nucleic acid sequence contemplated according to the invention.

Once the vector contains the desired coding region, the vector may be introduced ex vivo into a selected population of cells isolated from a patient, and the transfected cells then reintroduced into a patient. The coding sequence for the repair enzyme, ribozyme, wild-type version of a mutant protein, or oligonucleotide, will then be expressed in the patient, and the reintroduced population of cells may expand and thus provide a cell population in which the frameshift mutation is corrected.

Alternatively, the vector may be encapsulated in liposomes, as described hereinbelow, and administered to the patient. The vector-containing liposomes may be prepared so as to target a particular cell type suspected or known to contain a frameshift mutation in a particular gene, and the vector will be introduced into that cell type and result in correction of the frameshift mutation, i.e., by virtue of the presence of the encoded DNA repair enzyme or by substitution of the mutant gene sequence with the corresponding wild-type sequence. Should the frameshift mutation result from a splicing defect, the presence of an appropriate ribozyme is expected to result in correction of the splicing defect, and thus of the frameshift mutation.

EXAMPLE 6

Preparation of DNA Repair Enzymes

DNA repair enzymes may be prepared and purified for use in the invention as follows. A general review of purification methods for DNA repair enzymes can be found in DNA REPAIR: A Laboratory Manual of Research Procedures, edited by E. Friedberg and P. C. Hanawalt, published by Marcel Dekker, New York.

With regard to purification of repair enzymes useful according to the invention, the first step of the purification process, molecular sieving, serves to separate the DNA repair enzymes from the vast majority of proteins with larger sizes based on relative rates of migration of the DNA repair enzymes and the contaminating proteins through the molecular sieve matrix.

Molecular sieving can be accomplished by many methods, including gel filtration and electrophoresis. In gel filtration proteins flow around and through pores in beads made from dextran, polyacrylamide, agarose, agarose and acrylamide composites, or other material. The size of the bead pores include or exclude proteins based on size. In electrophoresis, proteins move in an applied electric field through a sizing matrix.

The preferred molecular sieving method for use with the present invention is gel filtration because the enzyme can be easily recovered and because the method is independent of such factors as net protein charge. The pore size of the beads used with this method are selected to maximize separation of DNA repair enzymes from the bulk of other proteins. A general guideline for selecting the gel filtration matrix is that the gel should have an exclusion limit greater than about twice the molecular weight or Stokes' radius of the DNA repair enzyme and less than about 60,000 daltons or 35 Angstroms.

A wide variety of elution buffers may be used to elute the DNA repair enzyme from the gel filtration column. The selected buffer should satisfy the following criteria: 1) the buffer should not denature or inactivate the DNA repair enzyme, 2) the buffer should not permit ionic adsorption of the DNA repair enzyme to the gel filtration media, and 3) the buffer should be compatible with loading of the eluate onto the nucleic acid affinity column, that is, the elution buffer should be chosen so that complexes will form between the DNA repair enzyme and the immobilized nucleic acids of the affinity column.

The second step of the purification process-nucleic acid binding-separates the DNA repair enzymes from the remaining protein impurities by the ability of DNA repair enzymes to reversibly bind to nucleic acids. Separation by nucleic acid binding can be accomplished by various methods, including nucleic acid affinity chromatography. In this method, nucleic acids are immobilized on an inter matrix, such as agarose, polyacrylamide beads, cellulose or other media. Depending on the DNA repair enzyme which is being purified, the immobilized nucleic acids may be double- or single-stranded DNA, double- or single-stranded RNA, or other types, lengths, structures or combination of nucleic acids, such as tRNA, Z-DNA, supercoiled DNA, ultraviolet-irradiated DNA or DNA modified by other agents. Single-stranded DNA is preferred.

The nucleic acids may be attached to the solid phase matrix by a variety of methods, including covalent attachment of the nucleic acid through primary amines or by absorbing the nucleic acids to a matrix such as cellulose, which releases nucleic acids slowly. The preferred immobilization method is use in a cyanogen-bromide activated Sepharose and to bind the nucleic acids to the activated Sepharose covalently. Alternatively, single-stranded DNA covalently bound to agarose can be purchased commercially from Bethesda Research Labs. Gaithersburg, Md. (Catalog No. 5906SA).

The DNA repair enzymes are applied to the nucleic acids in a solution which should satisfy the following criteria: 1) the solution should permit reversible binding of the DNA repair enzyme to the nucleic acids, 2) the solution should reduce nonspecific binding of contaminating proteins to the nucleic acids, and 3) the solution should not cause damage to the nucleic acids. In general, a neutral buffered solution with physiological saline and 1 mM EDTA will satisfy these criteria. As discussed above, in accordance with the invention, the nucleic acid affinity column. Accordingly, the elution buffer used with the molecular sieve column should be chosen to satisfy the foregoing criteria.

The bound DNA repair enzymes are eluted from the nucleic acid affinity column with a gradient which removes the enzyme from the nucleic acid at a characteristic condition and concentrates the enzyme by the focusing effect of the gradient. The elution system, however, should not denature the enzyme or introduce contaminants into the final product. A gradient of NaCl up to 1.0M will in general be sufficient to reverse binding of most DNA repair enzymes to nucleic acids. In appropriate cases, the gradient may be one of another salt, increasing or decreasing pH, temperature, voltage or detergent, or, if desired, a competing ligand may be introduced to replace the nucleic acid binding.

EXAMPLE 7

Liposomal Delivery According to the Invention

Substances may be administered according to the invention using any delivery means known in the art. Described below is liposomal delivery. Liposomes which are used to administer the DNA repair enzymes, ribozymes, a wild-type version of a hybrid wild-type/nonsense protein, or nucleic acid sequences encoding enzymes, ribozymes or a wild-type protein, antibodies specific for a hybrid wild-type/nonsense protein or oligonucleotides can be of various types and can have various compositions. The primary restrictions are that the liposomes should not be toxic to the living cells and that they should deliver their contents into the interior of the cells being treated.

The use of pH sensitive liposomes to mediate the cytoplasmic delivery of calcein and FITC dextran has been described (see Straubinger et al., Cell 32:1069–1079, 1983; and Straubinger et al., FEBS Letters 179:148–154, 1985. Other discussions of pH sensitive liposomes can be found in chapter 11 of the book CELL FUSION, edited by A. E. Sowers, entitled "Fusion of Phospholipid Vesicles Induced by Divalent Cations and Protons" by Nejat Duzgunes et al., Plenum Press, N.Y., 1987, 241–267. See also Ellens et al., Biochemistry, 23:1532–1538, 1984, and Bentz et al., Biochemistry 26:2105–2116, 1987.

The liposomes may be of various sizes and may have either one or several membrane layers separating the internal and external compartments. The most important elements in liposome structure are that a sufficient amount of enzyme or nucleic acid be sequestered so that only one or a few liposomes are required to enter each cell for delivery of the substance, and that the liposome be resistant to disruption. Liposome structures include small unilamellar vesicles (SUVs, less than 250 angstroms in diameter), large unilamellar vesicles (LUVs, greater than 500 angstroms in diameter), and multilamellar vesicles (MLs). In the example presented below, although SUVs are used to administer DNA repair enzymes, the methods are applicable to administration of ribozymes or sequences encoding repair enzymes, ribozymes, antibodies specific for hybrid wild-type/nonsense proteins, or wild-type genes or their encoded proteins, or oligonucleotides.

SUVs can be isolated from other liposomes and unincorporated enzyme by molecular weight can be isolated from other liposomes and unincorporated enzyme by molecular sieve chromatography, which is precise but time consuming and dilutes the liposomes, or differential centrifugation, which is rapid but produces a wider range of liposome sizes.

The liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

The liposomes useful according to the invention may be prepared, for example, as described in U.S. Pat. No. 5,296,231, which describes preparation of liposomes containing a DNA repair enzyme, although it should be borne in mind that liposomes useful according to the invention may contain any one of the substances as herein described. Briefly, by combining a phospholipid component with an aqueous component containing the DNA repair enzyme (or desired substance) under conditions which will result in vesicle formation. The phospholipid concentration must be sufficient to form lamellar structures, and the aqueous component must be compatible with biological stability of the enzyme. Methods for combining the phospholipids onto glass and then vesicles will form include: drying the phospholipids onto glass and then dispersing them in the aqueous component; injecting phospholipids dissolved in a vaporizing or non-vaporizing organic solvent into the aqueous component which has previously been heated; and dissolving phospholipids in the aqueous phase with detergents and then removing the detergent by dialysis. The concentration of the DNA repair enzyme in the aqueous component can be increased by lyophilizing the enzyme onto dried phospholipids and then rehydrating the mixture with a reduced volume of aqueous buffer. SUV's can be produced from the foregoing mixtures either by sonication or by dispersing the mixture through either small bore tubing or through the small orifice of a French Press.

DNA repair enzymes incorporated into liposomes can be administered to living cells internally or topically. Internal administration to animals or humans requires that the liposomes be pyrogen-free and sterile. To eliminate pyrogens, pyrogen-free raw materials, including all chemicals, enzymes, and water, are used to form the liposomes. Sterilization can be performed by filtration of the liposomes through 0.2 micron filters. For injection, the liposomes are suspended in a sterile, pyrogen-free buffer at a physiologically effective concentration. Topical administration also requires that the liposome preparation be pyrogen-free, and sterility is desirable. In this case, a physiologically effective concentration of liposomes can be suspended in a buffered polymeric glycol gel for even application to the skin. In general, the gel should not include non-ionic detergents which can disrupt liposome membranes. Other vehicles can also be used to topically administer the liposomes.

The concentration of the substance in the final preparation can vary over a wide range, a typical concentration being on the order of 50 ug/ml. In the case of pH sensitive liposomes, lower concentrations of the substance can be used, e.g., on the order of 0.01 to 1.0 ug/ml for liposomes administered to cells internally. In case of topical application, higher liposome concentrations used, e.g., ten or more times higher.

EXAMPLE 8

Adminstration Across the Blood-Brain Barrier

Where it is desired according to the invention to administer a DNA repair enzyme, a ribozyme, or their nucleic acid coding sequences, a wild-type version of a hybrid wild-type/ nonsense protein that is associated with the disease, or its coding sequence, or oligonucleotides or their coding sequences, or liposomes containing such substances, to an individual such that the administered material crosses the blood-brain barrier, several methods are known in the art.

For example, a substance to be administered, whether it be protein or nucleic acid or liposome, may be co-administered with a polypeptide, for example a lipophilic polypeptide that increases permeability at the blood-brain barrier. Examples of such polypeptides include but are not limited to bradykinin and receptor mediated permeabilizers, such as A-7 or its conformational analogues, as described in U.S. Pat. Nos. 5,112,596 and 5,268,164. The permeabilizing polypeptide allows the co-administered repair enzyme, ribozyme, coding sequence or liposome to penetrate the blood-brain barrier and arrive in the cerebrospinal fluid compartment of the brain, where the repair enzyme, ribozyme, or coding sequence may then reach and enter a target neuronal cell. Alternatively, the substance to be administered may be coupled to a steroidal estrogel or androgel to increase binding to steroid receptors and thus access to the brain.

Another exemplary method for administering a substance such as a DNA repair enzyme, ribozyme, antibody, nucleic acids, or liposomes containing such molecules, according to the invention includes forming a complex between the substance to be administered and an antibody that is reactive with a transferrin receptor, as described in U.S. Pat. No. 5,182,107. The complex may include a cleavable or non-cleavable linker and is administered under conditions whereby binding of the antibody to a transferrin receptor on a brain capillary endothelial cell occurs and the substance is transferred across the blood-brain barrier in active form.

Other Dosages and Modes of Administration

A patient that is subject to a disease state which is associated with a frameshift mutation may be treated in accordance with the invention, as described above, via in vivo, ex vivo or in vitro methods. For example in in vivo treatments, a nucleic acid vector encoding a repair enzyme, ribozyme, wild-type version of a hybrid wild-type/nonsense protein, or oligonucleotide that corresponds in sequence (except for the inserted or deleted nucleotide(s)) to the frameshifted region of the hybrid wild-type/nonsense protein coding region can be administered to the patient, preferably in a pharmaceutically acceptable delivery vehicle and a biologically compatible solution, by ingestion, injection, inhalation or any number of other methods. The dosages administered will vary from patient to patient; an "effective dose" will be determined by the level of enhancement of function of the transferred genetic material balanced against any risk of deleterious side effects. Monitoring gene expression and/or the presence or levels of the encoded mutant protein or its corresponding "sense" protein will assist in selecting and adjusting the dosages administered. Generally, a composition including a vector will be administered in a single dose in the range of 10 ng–100 ug/kg body weight, preferably in the range of 100 ng–10 ug/kg body weight, such that at least one copy of the sequence is delivered to each target cell. A composition including a protein, e.g., a DNA repair enzyme or a wild-type version of a hybrid wild-type/nonsense protein, will be administered in single or multiple doses, as determined by the physician, in the range of 10 ug–1 mg, or within the range of 100 ug–50 ug. A composition including a nucleoprotein such as a ribozyme will be administered in single or multiple doses, as determined by the physician, in the range of 50 ug–1 mg, or within the range of 100 ug–500 ug. A composition including an oligonucleotide will be administered in a single dose in the range of 5 ng–10 ug, or within the range of 100 ng–500 ng. Any of the above dosages may be administered according to the body weight of the patient, as determined by the physician. Ex vivo transduction is also contemplated within the present invention. Cell populations can be removed from the patient or otherwise provided, transduced with a vector in accordance with the invention, then reintroduced into the patient. The number of cells reintroduced into the patient will depend upon the efficiency of vector transfer, and will generally be in the range of $10^4$–$10^6$ transduced cells/ patient.

The cells targeted for ex vivo gene transfer in accordance with the invention include any cells to which the delivery of the vector is desired, for example, neuronal cells or stem cells. Protein, nucleic acid, or cells administered according to the invention is preferably administered in admixture with a pharmaceutically acceptable carrier substance, e.g., magnesium carbonate, lactose, or a phospholipid to form a micelle, the carrier and protein, nucleic acid or cell together can form a therapeutic composition, e.g., a pill, tablet, capsule or liquid for oral administration to the mammal. Other forms of compositions are also envisioned, e.g., a liquid capable of being administered nasally as drops or spray, or a liquid capable of intravenous, parenteral, subcutaneous, or intraperitoneal administration. The substance administered may be in the form of a biodegradable sustained release formulation for intramuscular administration. For maximum efficacy, where zero order release is desirable, e.g., an implantable or external pump, e.g., an Infusaid™ pump (Infusaid Corp, Mass.), may be used.

Kits Useful According to the Invention

The invention encompasses kits for diagnosis or treatment of diseases according to the invention, a kit including suitable packaging materials and one or more of the following reagents: a nucleic acid probe is as defined hereinabove, and optionally means for detecting the probe when bound to its complementary sequences. For example, the nucleic acid probe may be labeled, e.g., radiolabeled, fluorescently labeled, etc., or may be detected via indirect labeling techniques, e.g., using a biotin/avidin system, well known in the art.

A diagnostic system, preferably in kit form, comprises yet another embodiment of this invention. This system is useful for assaying the presence of a hybrid wild-type/nonsense protein or its derivative in cells by the formation of an immune complex. This system includes at least one package that contains an antibody of this invention. Optionally, a kit also may include a positive tissue sample control.

Antibodies are also utilized along with an "indicating group" also sometimes referred to as a "label". The indicating group or label is utilized in conjunction with the antibody as a means for determining whether an immune reaction has taken place, and in some instances for determining the extent of such a reaction.

The terms "indicating group" or "label" are used herein to include single atoms and molecules that are linked to the antibody or used separately, and whether those atoms or molecules are used alone or in conjunction with additional reagents. Such indicating groups or labels are themselves well-known in immunochemistry and constitute a part of this invention only insofar as they are utilized with otherwise novel antibodies, methods and/or systems.

For example, an antigen-specific antibody or antibody fragment is detectably labeled by linking the same to an enzyme and use it in an EIA, or enzyme-linked immunosorbent assay (ELISA). This enzyme, in turn, when later exposed to a substrate in such a manner as to produce a chemical moiety which can be detected, for example, by spectrophotometric, flourometric or, most preferably, by visual means. The substrate may be a chromogenic substrate which generates a reaction product visible to the naked eye.

Enzymes which can be used to detectably label the binding protein which is specific for the desired detectable mutant protein, include, but are not limited to, alkaline phosphatase, horseradish peroxidase, glucose-6-phosphate dehydrogenase, staphylococcal nuclease, delta-V-steroid isomerase, yeast alcohol dehydrogenase, alpha-glycerophosphate dehydrogenase, triose phosphate isomerase, asparaginase, ribonuclease, urease, catalase, glucose-6-phosphate dehydrogenase, glucoamylase and acetylcholinesterase.

By radioactively labeling the binding protein, for example, the antibody, it is possible to detect the antigen bound to a solid support through the use of a radioimmunoassay (RIA). The radioactive isotope can be detected by such means as the use of a gamma counter or a scintillation counter or by autoradiography. Isotopes which are particularly useful for the purpose of the present invention are: $^{3}H$, $^{131}I$, $^{14}C$, and preferably $^{125}I$.

It is also possible to label the first or second binding protein with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The first or second binding protein also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the first or second binding protein. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The invention also includes diagnostic reagents for use in the present invention, such as nucleic acid sequences, probes and antibody molecules, and/or positive tissue controls, as described above, and kits including such reagents for use in diagnosing or treating a disease.

An indicating group or label is preferably supplied along with the antibody and may be packaged therewith or packaged separately. Additional reagents such as hydrogen peroxide and diaminobenzideine, and nickel ammonium sulfate may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Other Embodiments

It will be understood that the invention is described by way of illustration only. Many other embodiments of the present invention in addition to those herein described will be apparent to those skilled in the art from the description herein given without departing from the scope of the present invention as defined in the appended claims.

TABLE 1

Estimated percentages of early (<60 years)
and late (>60 years) Alzheimer's disease (AD) onset.
60% non-familial/40% familial
(Van Broeckhoven, 1995, Eur. Neurol. 35, 8–19)

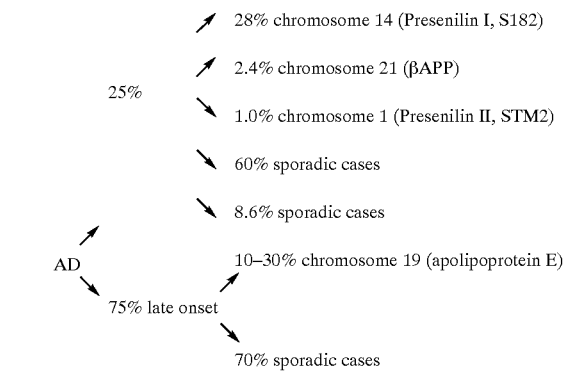

According to Ott et al. (Br. Med. J. 310, 970–973, 1995) the prevalence of dementia increases exponentially with age. In a case finding study in a general population of subjects of 65 years of age and older, 34% of the subjects aged 85 and older had dementia. Of all cases of dementia, 72% were cases of Alzheimer's disease.

TABLE 2

Immunoreactivities within the frontal lobe of the human frontal cortex for various neuronal proteins of which the mRNA is expressed in the +1 reading frame. Tissues were obtained from controls and neuropathologically confirmed Alzheimer cases.

| autopsy no. | age (years) | sex (m/f) | AMY$^{+1}$ | Tau$^{+1}$ | Ubi$^{+1}$ | NF-H$^{+1}$ | MAP2$^{+1}$ |
|---|---|---|---|---|---|---|---|
| controls | | | | | | | |
| 89004 | 34 | m | − | − | − | − | − |
| 81267 | 43 | m | − | − | − | − | − |
| 88149 | 58 | m | − | − | − | − | − |
| 90183 | 65 | f | − | − | − | − | − |
| 90202 | 72 | m | − | − | − | − | − |
| 91090 | 80 | f | − | − | − | + | + |
| 91126 | 82 | f | − | − | − | − | − |
| 90203 | 85 | m | − | − | − | − | − |
| 88109 | 85 | f | − | − | − | − | − |
| 81033 | 90 | f | − | − | − | − | + |
| 90206 | 90 | f | − | − | − | − | − |
| % pos. staining | | | 0% | 0% | 0% | 9% | 18% |

TABLE 2-continued

Immunoreactivities within the frontal lobe of the human frontal cortex for various neuronal proteins of which the mRNA is expressed in the +1 reading frame. Tissues were obtained from controls and neuropathologically confirmed Alzheimer cases.

| autopsy no. | age (years) | sex (m/f) | AMY$^{+1}$ | Tau$^{+1}$ | Ubi$^{+1}$ | NF-H$^{+1}$ | MAP2$^{+1}$ |
|---|---|---|---|---|---|---|---|
| Alzheimer's cases | | | | | | | |
| 89166 | 40 | m | − | − | + | − | − |
| 863645 | 45 | m | +$^1$ | +$^1$ | − | + | + |
| 90262 | 49 | m | + | − | + | − | + |
| 91092 | 54 | f | − | − | + | − | − |
| 850050 | 56 | f | − | − | + | + | + |
| 92140 | 62 | m | − | − | + | + | + |
| 88252 | 66 | f | − | − | − | − | − |
| 83170 | 70 | f | + | − | + | +$^1$ | + |
| 93104 | 70 | m | + | − | + | + | + |
| 91118 | 73 | f | − | − | + | − | − |
| 90349 | 77 | m | − | − | + | + | − |
| 93099 | 77 | m | − | − | − | + | + |
| 93225 | 81 | m | − | − | − | + | + |
| 93101 | 83 | f | − | − | − | + | + |
| 91045 | 85 | f | − | − | + | + | − |
| 90345 | 86 | m | − | − | + | − | + |
| 91061 | 88 | m | + | − | − | − | + |
| 86004 | 90 | f | − | − | − | + | + |
| 93105 | 92 | f | − | − | + | + | + |
| % pos. standing | | | 26% | 5% | 63% | 63% | 68% |

$^1$also in glia (possible gliosis)

TABLE 3

Immunoreactivities in the human hippocampus for various neuronal proteins of which the mRNA is expressed in the +1 reading frame. Tissues were obtained from controls and neuropathologically confirmed Alzheimer and Down syndrome cases.

| autopsy no. | age (years) | sex (m/f) | neuropathological state* plaques | tangles | βAPP$^{+1}$ | Tau$^{+1}$ | Ubi-B$^{+1}$ |
|---|---|---|---|---|---|---|---|
| non-demented controls | | | | | | | |
| 89004 | 34 | m | − | − | − | − | − |
| 81267 | 43 | m | − | − | − | + | − |
| 88149 | 58 | m | − | +$^a$ | − | − | − |
| 90183 | 65 | f | − | − | − | − | − |
| 90202 | 72 | m | +$^b$ | +$^c$ | − | − | + |
| 91090 | 80 | f | +$^b$ | +$^c$ | − | − | + |
| 91126 | 82 | f | − | +$^c$ | − | − | + |
| 90203 | 85 | m | +$^b$ | +$^b$ | − | + | + |
| 81033 | 90 | f | +$^b$ | +$^b$ | − | − | + |
| 90206 | 90 | f | − | +$^a$ | − | − | + |
| % pos. staining | | | | | 0% | 20% | 60% |
| Alzheimer's cases | | | | | | | |
| 89166 | 40 | m | +$^a$ | +$^c$ | − | + | + |
| 863645 | 45 | m | +$^b$ | +$^c$ | − | + | + |
| 90262 | 49 | m | +$^b$ | +$^c$ | − | + | + |
| 91092 | 54 | f | +$^b$ | +$^c$ | + | + | + |
| 850050 | 56 | f | +$^b$ | +$^a$ | − | − | + |
| 92140 | 61 | m | +$^b$ | +$^c$ | + | + | + |
| 88252 | 66 | f | +$^c$ | +$^c$ | − | − | + |
| 83170 | 70 | f | +$^c$ | +$^c$ | + | + | + |
| 93104 | 70 | m | +$^c$ | +$^c$ | + | + | − |
| 91118 | 73 | f | +$^b$ | +$^c$ | − | + | + |
| 90349 | 77 | m | +$^b$ | +$^c$ | + | + | + |
| 93099 | 77 | m | +$^b$ | +$^c$ | + | + | + |
| 93225 | 81 | m | +$^b$ | +$^c$ | + | + | + |
| 93101 | 83 | f | +$^b$ | +$^c$ | − | + | + |
| 88109 | 85 | f | +$^a$ | +$^b$ | − | + | + |
| 91045 | 85 | f | +$^b$ | +$^c$ | − | + | + |
| 90345 | 86 | m | +$^b$ | +$^c$ | + | − | + |
| 91061 | 88 | m | +$^b$ | +$^c$ | + | + | + |
| 86004 | 90 | f | +$^c$ | +$^c$ | − | + | + |
| 93105 | 92 | f | +$^a$ | +$^c$ | + | + | + |
| % pos. staining | | | | | 50% | 85% | 95% |
| Down's syndrome | | | | | | | |
| 25002 | 54 | f | +$^b$ | +$^c$ | + | + | + |
| 92272 | 58 | f | +$^c$ | +$^c$ | + | + | + |
| 89154 | 59 | f | +$^b$ | +$^c$ | + | + | + |
| 25001 | 62 | f | +$^a$ | +$^c$ | + | + | + |
| 95325 | 63 | f | − | − | − | + | − |
| 94146 | 64 | m | +$^b$ | +$^c$ | + | + | + |
| 93048 | 67 | f | +$^c$ | +$^c$ | − | + | + |
| % positive staining | | | | | 71% | 100% | 86% |

*number of plaques (all types) and tangles as revealed by Congo and Bodian silver staining:
a) few,
b) moderate,
c) many.

TABLE 4

SUMMARY OF RESULTS

| | Frontal cortex (area 11) | | | Temporal cortex (area 38) | | | Hippocampus | | |
|---|---|---|---|---|---|---|---|---|---|
| | Amy$^{+1}$ | Tau$^{+1}$ | Ubi$^{+1}$ | Amy$^{+1}$ | Tau$^{+1}$ | Ubi$^{+1}$ | Amy$^{+1}$ | Tau$^{+1}$ | Ubi$^{+1}$ |
| non dementing controls (n = 10) | 0 | 20 | 0 | 0 | 20 | 10* | 0 | 20 | 60* |
| Alzheimer's disease (n = 20) | 15 | 80 | 80 | 40 | 100 | 95 | 50 | 85 | 95 |
| Down syndrome (n = 7) | 86 | 100 | 86 | 86 | 100 | 86 | 71 | 100 | 86 |

Controls were sex- and age-matched.
*in old non-demented patients with some age related neuropathology (tangles, plaques)

TABLE 4-continued

SUMMARY OF RESULTS

|  | Frontal cortex (area 11) | | | Temporal cortex (area 38) | | | Hippocampus | | |
|---|---|---|---|---|---|---|---|---|---|
|  | Amy$^{+1}$ | Tau$^{+1}$ | Ubi$^{+1}$ | Amy$^{+1}$ | Tau$^{+1}$ | Ubi$^{+1}$ | Amy$^{+1}$ | Tau$^{+1}$ | Ubi$^{+1}$ |

One Down syndrome patient (#953251, age 63 years) does not show important neuropathology (no neurofibrillary tangles!). In this patient no Amy$^{+1}$, Ubi$^{+1}$ and ALZ-50 (marker for early Alzheimer changes) immunoreactivity can be seen. Tau$^{+1}$ immunoreactivity is present in cells resembling microglia. This case may be a Down patient with incomplete trisomy chromosome 21.
Amy$^{+1}$ and Ubi$^{+1}$ immunoreactivity are absent in the substantia nigra and striatum of 11 Parkinson patients, except for the striatum of one case (#90047) who also shows signs of Alzheimer's disease (tangles, plaques).
Amy$^{+1}$ and Ubi$^{+1}$ are absent from 1 patient (#93201) with frontal lobe dementia (Pick's disease), whereas Tau$^{+1}$ immunoreactivity is present in microglia. Tau$^{+1}$ immunoreactivity is not Alzheimer specific, since it also occurs in Parkinsons patients and even in the substantia nigra and stiatum of age-matched controls. It is possibly a good marker for microglia.
Amy$^{+1}$ and Ubi$^{+1}$ immunoreactivity coexist in tangles and are both present in ALZ-50 positive neuropathological structures (e.g. tangles).
Ubi$^{+1}$ immunoreactivity coexists in a subpopulation of wild-type Ubiquitin immunoreactive cells.
Ubi$^{+1}$ immunoreactivity shows an age-dependant expression in the hippocampus of the control group (from 72 years onwards).

TABLE 5

|  | BASE PAIRS (CODING SEQUENCE OF LONGEST FORM) | GAGAG MOTIFS | |
|---|---|---|---|
|  |  | EXPECTED NUMBER (1:1024) | ACTUAL NUMBER |
| βAPP | 2234 | 2.2 | 7 |
| TAU | 1096 | 1.1 | — |
| UBIQUITIN | 687 | 0.7 | 2 |
| APOLIPOPROTEIN E4 | 953 | 0.9 | — |
| MAP2 | 5475 | 5.3 | 11 |
| NF-LOW (68K) | 582 | 0.6 | 3 |
| NF-MEDIUM (145K) | 2748 | 2.7 | 3 |
| NF-HIGH (200K) | 3063 | 3.1 | 2 |

TABLE 6

|  | CHROMO-SOME | EXON NO. | MOL. WEIGHT (kDa) LONGEST FORM | BASE PAIRS CODING SEQ. LONGEST FORM (total genomic seq.-kb) | GAGAG MOTIFS | | EXON(S) FROM WHICH +1 PEPTIDE IS DERIVED | PRE-DICTED MOL. WEIGHT OF +1 PEPTIDE | +1 PEPTIDE (C-terminus) |
|---|---|---|---|---|---|---|---|---|---|
|  |  |  |  |  | EXPECTED NUMBER (1:1024) | ACTUAL NUMBER |  |  |  |
| βAPP[1] | 21q21.3–q22.05 | 18 | 135 | 2234 (170) | 2.2 | 7 | 9/10 | 38 | RGRTSSKELA SEQ ID NO: 1 |
| TAU[2] | 17q21 | 15 | 67 | 1096 (100) | 1.1 | — | 13 | 36 | HGRLAPARHAS SEQ ID NO: 2 |
| UBIQUITIN[3] | 17p11.1–p12 | 2 | 26 | 687 (1.8) | 0.7 | 2 | 2 | 11 | YADLRRDPDRQ SEQ ID NO: 3 RQDHHPGSGAQ SEQ ID NO: 4 |

References:
1. Yoshikai et al., Gene 87, 257, 1990; Selkoe et al., Proc. Natl. Acad. Sci USA 85, 7341, 1988;
2. Neve et al., J. Mol. Brain Res. 1, 271, 1986; Andreadis et al., Biochemistry, 31, 10626, 1992, in exon 4A of big Tau five GAGAG motifs are present;
3. Baker and Board, Nucl. Acids Res. 15, 443, 1987, Webb et al., Am. J. Hum. Genet. 46, 308, 1990.

We claim:

1. A method for the diagnosis of a neurodegenerative disease selected from the group consisting of Alzheimer's Disease (AD) and Downs' Syndrome (DS) caused by or associated with a somatic mutation within a GAGAX sequence in a gene wherein X is one of G, A, T or C and encoding a frameshift mutation, said method comprising:

i. providing a biological sample comprising genomic DNA or protein from a patient suspected of having or developing said neurodegenerative disease; and ii. detecting in said sample a said somatic mutation in a said gene or a protein encoded thereby, wherein detection of said somatic mutation in said gene or said protein encoded thereby is indicative of said neurodegenerative disease.

2. The method of claim 1, wherein the frameshift mutation comprises a deletion or an insertion of a nucleotide.

3. The method of claim 2, wherein said somatic mutation comprises a dinucleotide mutation.

4. The method of claim 2, wherein said GAGAX sequence comprises GAGAG or GAGAC.

5. The method of claim 1 wherein the gene having a frameshift mutation encodes the β amyloid precursor protein, the Tau protein, ubiquitin, apolipoprotein-$E_4$ (Apo-$E_4$), microtubule associated protein II (MAP 2) or the neurofilament proteins.

6. The method of claim 1 wherein the biological sample comprises body fluid or tissue.

7. The method of claim 6 wherein said body fluid comprises cerebral spinal fluid or blood.

8. The method of claim 6, wherein the tissue comprises skin or nose epithelium.

9. The method of claim 1, wherein the mutant gene is detected by formation of a nucleic acid duplex wherein a first strand of said duplex comprises a nucleic acid probe having a sequence complementary to part of the mutant gene encompassing the mutation giving rise to the frameshift mutation, and the second strand of said duplex comprises a nucleic acid sequence of the mutant gene which is complementary to said probe.

10. The method of claim 1, wherein the mutant gene is detected using PCR to amplify a fragment of the mutant gene encompassing the mutation giving rise to the frameshift, and then probing for the amplified fragment using a nucleic acid probe having a sequence complementary to part of the mutant gene encompassing the mutation giving rise to the frameshift mutation, or by sequencingthe amplified fragment.

11. The method of claim 1, wherein the protein encoded by the mutant gene is detected using an antibody molecule having specificity for the mutant protein and not for the wild-type protein.

12. A method for identifying a neurodegenerative disease caused by or associated with a somatic mutation in a gene encoding a protein selected from the group consisting ofamyloid A4 (APP), Tau, ubiquitin B, ApoE4, MAP2, nerofilament protein low, neurofilament protein medium and neurofilament protein high, wherein said somatic mutation results in a translational frameshift and is within a GAGAX sequence, wherein X is one of G, A, T or C, said method comprising:

i. providing the sequence of a said gene;

ii. identifying the sequence of a mutant protein encoded by a gene sequence 3'-terminal to a said somatic mutation;

iii. preparing a probe to said mutant protein or a fragment thereof; and iv. probing a biological sample from a patient having a neurodegenerative disease and a biological sample from a patient not having said neurodegenerative disease, wherein the presence of said mutant protein in a biological sample from a patient having said neurodegenerative disease and the absence of said mutant protein in a biological sample from a patient not having said neurodegenerative disease indicates that said neurodegenerative disease or susceptibility to said neurodegenerative disease is caused by or associated with said somatic mutation in said gene.

* * * * *